(12) United States Patent
Haaf et al.

(10) Patent No.: US 6,794,336 B2
(45) Date of Patent: Sep. 21, 2004

(54) HERBICIDAL SUBSTITUTED PYRIDINES, THEIR PREPARATION, AND THEIR USE AS HERBICIDES AND PLANT GROWTH REGULATORS

(75) Inventors: Klaus Haaf, Kelkheim (DE); Lothar Willms, Hofheim (DE); Thomas Auler, Bad Soden (DE); Hubert Menne, Hofheim (DE); Hermann Bieringer, Eppstein (DE)

(73) Assignee: Aventis Crop Science GmbH, Frankfurt (DE)

( * ) Notice: Subject to any disclaimer, the term of this patent is extended or adjusted under 35 U.S.C. 154(b) by 0 days.

(21) Appl. No.: 10/177,526

(22) Filed: Jun. 21, 2002

(65) Prior Publication Data

US 2003/0229125 A1 Dec. 11, 2003

(30) Foreign Application Priority Data

Jun. 23, 2001 (DE) ......................................... 101 30 397

(51) Int. Cl.$^7$ ........................ A01N 43/40; A01N 43/72; A01N 43/56; C07D 213/64; C07D 401/14
(52) U.S. Cl. ...................... 504/250; 504/225; 504/251; 504/252; 504/253; 504/257; 504/244; 504/230; 504/235; 504/238; 504/242; 504/247; 504/248; 546/276.1; 546/300; 546/280.4; 546/284.4; 546/261; 546/279.1; 546/153; 546/175; 546/176; 544/124; 544/180; 544/238; 544/298; 544/405
(58) Field of Search ............................. 546/276.1, 300, 546/280.4, 284.4, 261, 279.1; 544/124; 504/225, 250, 251, 252, 253, 257, 244

(56) References Cited

U.S. PATENT DOCUMENTS

| 4,030,910 | A | | 6/1977 | Johnston | |
|---|---|---|---|---|---|
| 5,705,453 | A | * | 1/1998 | Kyomura et al. | ........... 504/117 |
| 5,707,932 | A | | 1/1998 | Kleemann et al. | |
| 5,807,804 | A | | 9/1998 | Kleemann et al. | |
| 5,869,426 | A | | 2/1999 | Karp et al. | |
| 6,080,861 | A | | 6/2000 | Karp et al. | |

FOREIGN PATENT DOCUMENTS

| EP | 0 196 184 A2 | 10/1986 |
|---|---|---|
| EP | 0 447 004 A2 | 9/1991 |
| EP | 0 488 474 A1 | 6/1992 |
| EP | 0 537 816 A1 | 4/1993 |

(List continued on next page.)

OTHER PUBLICATIONS

English language abstract for WO 00/75112 (Dec. 14, 2000).
English language abstract for WO 01/00580 (Jan. 4, 2001).

Primary Examiner—Evelyn Mei Huang
(74) Attorney, Agent, or Firm—Connolly Bove Lodge and Hutz LLP

(57) ABSTRACT

The present invention relates to a compound of the formula (I) or salt thereof formula (I)

in which $R^1$ is identical or different at each occurrence and is H, halogen, CN, nitro, $SF_5$, $(C_1–C_8)$alkyl, $(C_2–C_8)$alkenyl, $(C_2–C_8)$alkynyl, $(C_1–C_8)$alkoxy, $[(C_1–C_8)$alkyl]-carbonyl or $(C_1–C_8)$alkylsulfonyl, each of the radicals being unsubstituted or substituted,
or is $S(O)_p$—$R^7$, where
p=0, 1 or 2 and
$R^7$ is $(C_1–C_8)$alkyl, $(C_1–C_8)$haloalkyl or $NR^8R^9$, where $R^8$ and $R^9$ independently of one another are identical or different and are H, $(C_1–C_8)$alkyl, $(C_2–C_8)$alkenyl, $(C_7–C_{10})$arylalkyl, $(C_7–C_{10})$alkylaryl or $(C_6–C_{10})$aryl, each of the last-mentioned five radicals being unsubstituted or substituted,
or is a group of the formula where $R^{10}$ is $(C_1–C_8)$alkyl which is unsubstituted or substituted, and
W=O or S,
A is optionally substituted aryl or an optionally substituted heterocyclic radical,
X is O or S,
$R^2, R^3, R^4$, and $R^5$ are identical or different and are H, halogen, CN, $(C_1–C_8)$alkoxy or $(C_1–C_8)$alkyl, each of the two last-mentioned radicals being unsubstituted or substituted,
m is 0 or 1,
$R^6$ is H, $(C_1–C_8)$alkyl, $(C_1–C_8)$alkoxy, $(C_2–C_8)$alkenyl or $(C_2–C_8)$alkynyl, each of the four last-mentioned radicals being unsubstituted or substituted, or is hydroxyl or an acyl radical, and
B is an acyl radical,
or B and $R^6$ together form a 4- or 5-membered chain,
with the exception of N-hydroxy-N-[(6-phenoxy-2-pyridyl) methyl]-acetamide and its salts.

The compounds of the invention are suitable, for example, as herbicides and growth regulators.

26 Claims, No Drawings

FOREIGN PATENT DOCUMENTS

| | | |
|---|---|---|
| EP | 0 955 292 A1 | 11/1999 |
| EP | 0 955 300 A2 | 11/1999 |
| EP | 0 955 300 A3 | 11/1999 |
| GB | 2 277 930 A1 | 11/1994 |
| JP | WO 00/75112 A1 | 12/2000 |
| JP | WO 01/00580 A1 | 1/2001 |
| WO | WO 90/01929 * | 3/1990 |
| WO | WO 98/04550 | 2/1998 |
| WO | WO 99/24427 | 5/1999 |
| WO | WO 99/28301 | 6/1999 |
| WO | WO 99/50262 * | 10/1999 |

* cited by examiner

HERBICIDAL SUBSTITUTED PYRIDINES, THEIR PREPARATION, AND THEIR USE AS HERBICIDES AND PLANT GROWTH REGULATORS

It is known that substituted pyridines may possess herbicidal and plant growth regulating properties (cf., e.g., EP-A-0955300, WO 98/04550, EP-A-0955292, WO 00/75112, WO 01/00580, and WO 99/28301). In some cases, however, in the course of their use, these compounds have disadvantages, such as high persistency or inadequate selectivity in important crops, for example. Furthermore, EP-A-0196184 describes substituted pyridines.

Special 2,6-substituted pyridines have now been found which can be used with advantages as herbicides and plant growth regulators.

The present invention accordingly provides compounds of the formula (I) and/or salts thereof

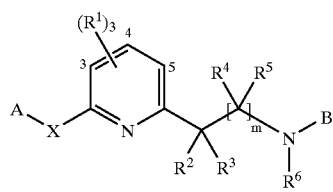

formula (I)

in which $R^1$ is identical or different at each occurrence and is H, halogen, CN, nitro, $SF_5$, $(C_1-C_8)$alkyl which is unsubstituted or substituted, for example, by one or more radicals from the group consisting of halogen, $(C_1-C_8)$alkoxy, $(C_1-C_8)$alkylthio, $(C_1-C_8)$alkylsulfinyl, $(C_1-C_8)$alkylsulfonyl, [$(C_1-C_8)$alkoxy]-carbonyl, and CN, or is $(C_2-C_8)$alkenyl or $(C_2-C_8)$alkynyl which are unsubstituted or substituted, for example, by one or more radicals from the group consisting of halogen, CN, $(C_1-C_8)$alkoxy, and $(C_1-C_8)$alkylthio, or is $(C_1-C_8)$alkoxy, [$(C_1-C_8)$alkyl]-carbonyl or $(C_1-C_8)$alkylsulfonyl, each of the radicals being unsubstituted or substituted, for example, by one or more radicals from the group consisting of halogen, CN, $(C_1-C_8)$alkoxy, and $(C_1-C_8)$alkylthio, or is $S(O)_p$—$R^7$, where p=0, 1 or 2 and $R^7$ is $(C_1-C_8)$alkyl, $(C_1-C_8)$haloalkyl or $NR^8R^9$, where $R^8$ and $R^9$ independently of one another are identical or different and are H, $(C_1-C_8)$alkyl, $(C_2-C_8)$alkenyl, $(C_7-C_{10})$arylalkyl, $(C_7-C_{10})$alkylaryl or $(C_6-C_{10})$aryl, each of the last-mentioned five radicals being unsubstituted or substituted, for example, by one or more radicals from the group consisting of halogen, CN, $(C_1-C_8)$alkoxy, and $(C_1-C_8)$alkylthio, or is a group of the formula

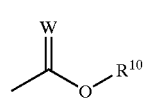

where $R^{10}$ is $(C_1-C_8)$alkyl which is unsubstituted or substituted, for example, by one or more radicals from the group consisting of halogen, CN, $(C_1-C_8)$alkoxy, and $(C_1-C_8)$alkylthio, and W=O or S, A is optionally substituted aryl, e.g., an optionally substituted phenyl radical, or is an optionally substituted heterocyclic radical, e.g., an optionally substituted heteroaromatic radical, such as optionally substituted pyridyl, pyrazolyl or thienyl, X is O or S, $R^2, R^3, R^4$, and $R^5$ are identical or different and are H, halogen, CN, $(C_1-C_8)$alkoxy or $(C_1-C_8)$alkyl, each of the two last-mentioned radicals being unsubstituted or substituted, for example, by one or more radicals from the group consisting of halogen, CN, $(C_1-C_8)$alkoxy, and $(C_1-C_8)$alkylthio, m is 0 or 1, $R^6$ is H, $(C_1-C_8)$alkyl or $(C_1-C_8)$alkoxy, each of the two last-mentioned radicals being unsubstituted or substituted, for example, by one or more radicals from the group consisting of halogen, $(C_1-C_8)$alkoxy, $(C_1-C_8)$alkylthio, $(C_1-C_8)$alkylsulfinyl, $(C_1-C_8)$alkylsulfonyl, [$(C_1-C_8)$alkoxy]-carbonyl, and CN, or is $(C_2-C_8)$alkenyl or $(C_2-C_8)$alkynyl, which are unsubstituted or substituted, for example, by one or more radicals from the group consisting of halogen, CN, $(C_1-C_8)$alkoxy, and $(C_1-C_8)$alkylthio, or is hydroxyl or an acyl radical such as formyl, [$(C_1-C_8)$alkyl]-carbonyl, [$(C_2-C_8)$alkenyl]-carbonyl, [$(C_2-C_8)$alkynyl]-carbonyl, $(C_1-C_8)$alkylsulfonyl, $(C_2-C_8)$alkenylsulfonyl or $(C_2-C_8)$alkynylsulfonyl, each of the last-mentioned six radicals being unsubstituted or substituted, for example, by one or more radicals from the group consisting of halogen, CN, $(C_1-C_8)$alkoxy, and $(C_1-C_8)$alkylthio, or is phenylcarbonyl or phenylsulfonyl, the phenyl radical in each of the two last-mentioned radicals being unsubstituted or substituted, for example, by one or more radicals from the group consisting of halogen, CN, $NO_2$, $(C_1-C_8)$alkyl, $(C_1-C_8)$haloalkyl, and $(C_1-C_8)$alkoxy, $R^6$ preferably being other than hydroxyl, and B is an acyl radical, e.g., [$(C_1-C_8)$alkyl]-carbonyl such as linear or branched [$(C_1-C_8)$-alkyl]-carbonyl or [$(C_3-C_6)$cycloalkyl]-carbonyl, each of the radicals being unsubstituted or substituted, for example, by one or more radicals from the group consisting of halogen, $(C_1-C_8)$alkoxy, $(C_1-C_8)$alkylthio, $(C_1-C_8)$alkylsulfinyl, $(C_1-C_8)$alkylsulfonyl, [$(C_1-C_8)$alkyl]-carbonyl, [$(C_1-C_8)$alkoxy]-carbonyl, and CN, or is [$(C_2-C_8)$alkenyl]-carbonyl or [$(C_2-C_8)$alkynyl]-carbonyl, each of the last-mentioned two radicals being unsubstituted or substituted, for example, by one or more radicals from the group consisting of halogen, CN, $(C_1-C_8)$alkoxy, and $(C_1-C_8)$alkylthio, or is $(C_1-C_8)$alkylsulfonyl, such as linear or branched $C_1-C_8$-alkylsulfonyl or $(C_3-C_8)$cycloalkylsulfonyl, or is $(C_2-C_8)$alkenylsulfonyl or $(C_2-C_8)$alkynylsulfonyl, each of the radicals being unsubstituted or substituted, for example, by one or more radicals from the group consisting of halogen, CN, $(C_1-C_8)$alkoxy, and $(C_1-C_8)$alkylthio, or is phenylcarbonyl or phenylsulfonyl, the phenyl radical in each of the two last-mentioned radicals being unsubstituted or substituted, for example, by one or more radicals from the group consisting of halogen, CN, $NO_2$, $(C_1-C_8)$alkyl, $(C_1-C_8)$haloalkyl, and $(C_1-C_8)$alkoxy, or is mono- or di-[$(C_1-C_8)$alkyl]-aminosulfonyl, formyl or a group of the formula —CO—CO—R' in which R'=H, OH, $(C_1-C_8)$-alkoxy or $(C_1-C_8)$alkyl, each of the last-mentioned two radicals being unsubstituted or substituted, for example, by one or more radicals from the group consisting of halogen, CN, $(C_1-C_8)$alkoxy, and $(C_1-C_8)$alkylthio, or is a group of the formula

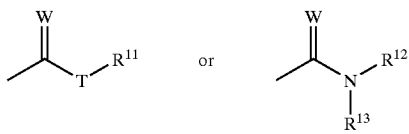

in which

W is an oxygen or sulfur atom (i.e., O or S),

T is O or S, $R^{11}$ is $(C_1-C_8)$alkyl, $(C_2-C_8)$alkenyl or $(C_2-C_8)$alkynyl, each of the three last-mentioned radicals being unsubstituted or substituted, for example, by one or more radicals from the group consisting of halogen, CN, $(C_1-C_8)$alkoxy, $(C_1-C_8)$alkylthio, [$(C_1-C_8)$alkyl]-carbonyl, and [$(C_1-C_8)$alkoxy]-carbonyl, $R^{12}$ and $R^{13}$ are identical or different and are H, $(C_1-C_8)$alkyl, $(C_2-C_8)$alkenyl or $(C_2-C_8)$alkynyl, each of the three last-mentioned radicals being unsubstituted or substituted, for example, by one or more radicals from the group consisting of halogen, CN, $(C_1-C_8)$alkoxy, $(C_1-C_8)$alkylthio, [$(C_1-C_8)$alkyl]-carbonyl, and [$(C_1-C_8)$alkoxy]-carbonyl, and the radicals $R^{12}$ and $R^{13}$ may together with the nitrogen atom form a heterocyclic radical which has 5 or 6 ring members, may contain further heteroatoms from the group consisting of N, O and S, and is unsubstituted or substituted, for example, by $(C_1-C_8)$alkyl or an oxo group, or B and $R^6$ together form a 4- or 5-membered chain, e.g. of the formula $(-CH_2)_m$—D— or —$D^1$—$(CH_2)_{m1}$—D—, the chain being unsubstituted or substituted, for example, by one or more, preferably from one to four, $(C_1-C_4)$alkyl radicals, D and $D^1$ independently of one another being $SO_2$ or CO, and m=3 or 4 and $m^1$=2 or 3, with the exception of N-hydroxy-N-[(6-phenoxy-2-pyridyl) methyl]-acetamide and its salts.

In the formula (I) and below, the carbon-containing radicals such as alkyl, alkoxy, haloalkyl, alkylamino and alkylthio radicals and also the corresponding unsaturated and/or substituted radical may in each case be straight-chain or branched in the carbon framework or, for carbon numbers of 3 or more, may also be cyclic. Unless indicated specifically, for these radicals the lower carbon frameworks, e.g., those having from 1 to 6 carbon atoms or, in the case of unsaturated groups, those having from 2 to 6 carbon atoms, are preferred. Alkyl radicals, both per se and in composite definitions such as alkoxy, haloalkyl, etc. are, for example, methyl, ethyl, n-, i- or cyclo-propyl, n-, i-, t-, 2- or cyclo-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the definition of the possible unsaturated radicals corresponding to the alkyl radicals; alkenyl is, for example, allyl, 1-methylprop-2-en-1-yl, 2-methyl-prop-2-en-1-yl, but-2-en-1-yl, But-3-en-1-yl, 1-methyl-but-3-en-1-yl and 1-methyl-but-2-en-1-yl; alkynyl is, for example, propargyl, but-2-yn-1-yl, but-3-yn-1-yl, 1-methyl-but-3-yn-1-yl.

Halogen is for example fluorine, chlorine, bromine or iodine. Haloalkyl, haloalkenyl and haloalkynyl are alkyl, alkenyl or alkynyl, respectively, which are partly or fully substituted by halogen, preferably by fluorine, chlorine and/or bromine, especially by fluorine or chlorine, examples being $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

A hydrocarbon-containing radical is a straight-chain, branched or cyclic and saturated or unsaturated aliphatic or aromatic radical which contains hydrocarbon units, e.g., alkyl, alkenyl, alkynyl, cycloalkyl, cycloalkenyl or aryl; aryl here is a mono-, bi- or polycyclic aromatic system, such as phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms, or phenyl.

Aryl is preferably phenyl substituted by one or more, preferably 1, 2 or 3, radicals from the group consisting of halogen, such as F, Cl, Br, and I, preferably F, Cl, and Br, and also alkyl, haloalkyl, alkoxy, haloalkoxy, hydroxyl, amino, nitro, cyano, alkoxycarbonyl, alkylcarbonyl, formyl, carbamoyl, mono- and dialkylaminocarbonyl, mono- and dialkylamino, alkylsulfinyl, and alkylsulfonyl, and in the case of the radicals with carbon atoms preference is given to those having from 1 to 4 carbon atoms, especially 1 or 2. Preference is generally given to substituents from the group consisting of halogen, e.g., fluorine and chlorine, $C_1-C_4$-alkyl, preferably methyl or ethyl, $C_1-C_4$-haloalkyl, preferably trifluoromethyl, $C_1-C_4$-alkoxy, preferably methoxy or ethoxy, $C_1-C_4$-haloalkoxy, nitro, and cyano.

A heterocyclic radial or ring (heterocyclyl) can be saturated, unsaturated or heteroaromatic and unsubstituted or substituted, and can also be fused on; it contains preferably one or more heteroatoms in the ring, preferably from the group N, O, and S; it is preferably an aliphatic heterocyclyl radical having from 3 to 7 ring atoms or a heteroaromatic radical having 5 or 6 ring atoms, and contains 1, 2 or 3 heteroatoms. The heterocyclic radical may, for example, be a heteroaromatic radical or ring (heteroaryl), such as a mono-, bi- or polycyclic aromatic system in which at least 1 ring contains one or more heteroatoms, or is a partially or fully hydrogenated radical, e.g., pyrrolidyl, piperidyl, pyrazolyl, morpholinyl, indolyl, quinolinyl, pyrimidinyl, triazolyl, oxazolyl, pyridyl, pyrimidinyl, pyridazinyl, pyrazinyl, thiazolyl, thienyl, pyrrolyl, oxazolinyl, isoxazolinyl, isoxazolyl, imidazolyl, and benzoxazolyl. Suitable substituents for a substituted heterocyclic radical include the substituents specified later on below, and also oxo. The oxo group may also occur on the ring heteroatoms, which may exist in different oxidation states, in the case of N and S, for example.

Substituted radicals, such as substituted hydrocarbon-containing radicals, e.g., substituted alkyl, alkenyl, alkynyl, aryl, phenyl, and benzyl, or substituted heterocyclyl or heteroaryl, are for example a substituted radical derived from the unsubstituted parent structure, the substituents being, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, alkyl and haloalkyl as well, and also unsaturated aliphatic radicals corresponding to the saturated hydrocarbon-containing radicals mentioned, such as alkenyl, alkynyl, alkenyloxy, alkynyloxy etc. In the case of radicals with carbon atoms, preference is given to those having from 1 to 4 carbon atoms, especially 1 or 2 carbon atoms. Preference is generally given to substituents from the group consisting of halogen, e.g. fluorine and chlorine, $(C_1–C_4)$alkyl, preferably methyl or ethyl, $(C_1–C_4)$haloalkyl, preferably trifluoromethyl, $(C_1–C_4)$ alkoxy, preferably methoxy or ethoxy, $(C_1–C_4)$haloalkoxy, nitro, and cyano. Particularly preferred substituents among these are methyl, methoxy, cyano and chlorine.

Unsubstituted or substituted phenyl is preferably phenyl which is unsubstituted or substituted one or more times, preferably up to three times, by identical or different radicals from the group consisting of halogen, $(C_1–C_4)$alkyl, $(C_1–C_4)$alkoxy, $(C_1–C_4)$haloalkyl, $(C_1–C_4)$haloalkoxy, cyano, and nitro, examples being o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, and o-, m- and p-cyanophenyl.

An acyl radical is a radical of an organic acid formed formally by eliminating an OH group from the organic acid, e.g., the radical of a carboxylic acid and radicals of acids derived therefrom such as the thiocarboxylic acid, unsubstituted or N-substituted iminocarboxylic acids or the radicals of carbonic monoesters, unsubstituted or N-substituted carbamic acids, sulfonic acids, sulfinic acids, phosphonic acids, and phosphinic acids.

An acyl radical is preferably formyl or aliphatic acyl from the group consisting of CO—$R^x$, CS—$R^x$, CO—O$R^x$, CO—CO—$R^x$, CS—O$R^x$, CS—S$R^x$, SO$R^Y$ or SO$_2R^Y$, $R^x$ and $R^Y$ each being a $C_1$–$C_{10}$ hydrocarbon radical which is unsubstituted or substituted, or aminocarbonyl or aminosulfonyl, the two last-mentioned radicals being unsubstituted, N-monosubstituted or N,N-disubstituted. Acyl is for example formyl, haloalkylcarbonyl, alkylcarbonyl such as $(C_1–C_4)$alkylcarbonyl, phenylcarbonyl, it being possible for the phenyl ring to be substituted, as indicated above for phenyl, for example, or alkyloxycarbonyl, phenyloxycarbonyl, benzyloxycarbonyl, alkylsulfonyl, alkylsulfinyl, N-alkyl-1-iminoalkyl, and other radicals of organic acids.

The invention provides all stereoisomers embraced by formula (I), and mixtures thereof. Such compounds of the formula (I) contain one or more asymmetric carbon atoms or else double bonds, which are not indicated specifically in the general formulae (I). The possible stereoisomers defined by their specific three-dimensional form, such as enantiomers, diastereomers, Z-isomers and E-isomers, are all embraced by the formula (I) and may be obtained by standard methods from mixtures of the stereoisomers or else may be prepared by stereoselective reactions in combination with the use of stereochemically pure starting materials.

The compounds of the formula (I) may form salts—for example those where the nitrogen atom of the pyridine or, where appropriate, a further heteroatom is in protonated form. These salts are, for example, salts of mineral acids such as hydrochloric acid, hydrobromic acid, and sulfuric acid, or else salts of organic acids such as formic acid, acetic acid, oxalic acid, citric acid or aromatic carboxylic acids such as benzoic acids.

Preference is given to compounds of the formula (I) and/or salts thereof in which $R^1$ is identical or different at each occurrence and is H, halogen, CN, $(C_1–C_8)$alkyl or $(C_1–C_8)$alkoxy, each of the last-mentioned two radicals being unsubstituted or substituted by one or more radicals from the group consisting of halogen, CN, $(C_1–C_8)$alkoxy, and $(C_1–C_8)$alkylthio, A is a phenyl radical or a 5- or 6-membered heterocyclic radical such as a 5- or 6-membered N- or S-containing heteroaromatic radical, the radicals being unsubstituted or substituted by one or more radicals from the group consisting of halogen, CN, $(C_1–C_8)$alkyl, $(C_1–C_8)$alkoxy halo$(C_1–C_8)$alkyl. halo$(C_1–C_8)$alkyloxy, halo$(C_1–C_8)$ alkylthio, and $(C_1–C_8)$alkoxy-$(C_1–C_8)$alkoxy, X is O or S, $R^2$ and $R^3$ are identical or different and are H or $(C_1–C_8)$ alkyl, the alkyl radical being unsubstituted or substituted by one or more radicals from the group consisting of halogen, CN, $(C_1–C_8)$alkoxy, and $(C_1–C_8)$alkylthio, m is 0, $R^6$ is H, formyl, $(C_1–C_8)$alkyl, $(C_3–C_8)$alkenyl, $(C_3–C_8)$ alkynyl, $(C_1–C_8)$-alkoxy or $[(C_1–C_8)$alkyl$]$-carbonyl, each of the last-mentioned five radicals being unsubstituted or substituted by one or more radicals from the group consisting of halogen, CN, $(C_1–C_8)$alkoxy, and $(C_1–C_8)$alkylthio, and B is an acyl radical such as $[(C_1–C_8)$alkyl$]$-carbonyl such as linear or branched $[(C_1–C_8)$-alkyl$]$-carbonyl or $[(C_3–C_6)$ cycloalkyl$]$-carbonyl, each of the radicals being unsubstituted or substituted, for example, by one or more radicals from the group consisting of halogen, $(C_1–C_8)$alkoxy, $(C_1–C_8)$alkylthio, $(C_1–C_8)$alkylsulfinyl, $(C_1–C_8)$ alkylsulfonyl, $[(C_1–C_8)$alkyl$]$-carbonyl, $[(C_1–C_8)$ alkoxy$]$-carbonyl, and CN, or is $[(C_2–C_8)$alkenyl$]$-carbonyl or $[(C_2–C_8)$alkynyl$]$-carbonyl, each of the radicals being unsubstituted or substituted, for example, by one or more radicals from the group consisting of halogen, CN, $(C_1–C_8)$ alkoxy, and $(C_1–C_8)$alkylthio, $(C_1–C_8)$alkylsulfonyl, such as linear or branched $C_1$–$C_8$-alkylsulfonyl or $(C_3–C_8)$cycloalkylsulfonyl, or $(C_2–C_8)$ alkenylsulfonyl or $(C_2–C_8)$alkynylsulfonyl, each of the radicals being unsubstituted or substituted, for example, by one or more radicals from the group consisting of halogen, CN, $(C_1–C_8)$alkoxy, and $(C_1–C_8)$alkylthio.

Particular preference is given to compounds of the formula (I) and/or salts thereof in which $R^1$ in position 3 and in position 5 of the pyridine ring, identical or different at each occurrence, is H or halogen, preferably fluorine or chlorine, and $R^1$ in position 4 of the pyridine ring is H, halogen, preferably fluorine or chlorine, CN, $(C_1–C_8)$alkyl or $(C_1–C_8)$alkoxy, each of the last-mentioned two radicals being unsubstituted or substituted by one or more radicals from the group consisting of halogen, CN, $(C_1–C_8)$alkoxy, and $(C_1–C_8)$alkylthio, A is a group of the formula (A')

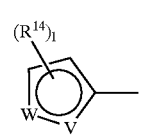

(A')

in which $R^{14}$ is identical or different at each occurrence and is halogen, CN, $(C_1–C_8)$alkyl, $(C_1–C_8)$alkoxy or $(C_1–C_8)$alkylthio, each of the last-mentioned three radicals being unsubstituted or substituted by one or more radicals from the group consisting of halogen, CN, $(C_1–C_8)$alkoxy, and $(C_1–C_8)$alkylthio, e.g., $(C_1–C_8)$ haloalkyl, $(C_1–C_8)$haloalkyloxy, $(C_1–C_8)$haloalkylthio or $(C_1–C_8)$alkoxy$(C_1–C_8)$alkyloxy, I is 1 or 2, V is CH, C(R$^{14}$) or N(C$_1$–C$_8$-alkyl) such as N(CH$_3$), W is N, S, N—CH, N—C(R$^{14}$), CH—CH, CH—C(R$^{14}$) or C(R$^{14}$)—C(R$^{14}$), R$^2$ and R$^3$ are identical or different and are H or (C$_1$–C$_8$) alkyl which is unsubstituted or substituted by one or more radicals from the group consisting of halogen, CN, (C$_1$–C$_8$)alkoxy, and (C$_1$–C$_8$)alkylthio, m is 0, R$^6$ is H or (C$_1$–C$_4$)alkyl which is unsubstituted or substituted by one or more radicals from the group consisting of halogen, CN, (C$_1$–C$_8$)alkoxy, and (C$_1$–C$_8$)alkylthio, and B is an acyl radical such as [(C$_1$–C$_8$)alkyl]-carbonyl such as linear or branched [(C$_1$–C$_8$)-alkyl]-carbonyl or [(C$_3$–C$_6$) cycloalkyl]-carbonyl, each of the radicals being unsubstituted or substituted, for example, by one or more radicals from the group consisting of halogen, (C$_1$–C$_8$)alkoxy, (C$_1$–C$_8$)alkylthio, (C$_1$–C$_8$)alkylsulfinyl, (C$_1$–C$_8$) alkylsulfonyl, [(C$_1$–C$_8$)alkyl]-carbonyl, [(C$_1$–C$_8$) alkoxy]-carbonyl, and CN, or is [(C$_2$–C$_8$)alkenyl]-carbonyl or [(C$_2$–C$_8$)alkynyl]carbonyl, each of the radicals being unsubstituted or substituted, for example, by one or more radicals from the group consisting of halogen, CN, (C$_1$–C$_8$) alkoxy, and (C$_1$–C$_8$)alkylthio, (C$_1$–C$_8$)alkylsulfonyl, such as linear or branched C$_1$–C$_8$-alkylsulfonyl or (C$_3$–C$_8$)cycloalkylsulfonyl, or (C$_2$–C$_8$) alkenylsulfonyl or (C$_2$–C$_8$)alkynylsulfonyl, each of the radicals being unsubstituted or substituted, for example, by one or more radicals from the group consisting of halogen, CN, (C$_1$–C$_8$)alkoxy, and (C$_1$–C$_8$)alkylthio.

Of particular interest are inventive compounds of the formula (I) and/or salts thereof in which A is a phenyl, pyridyl, pyrazolyl or thienyl radical which is attached to X via a carbon atom and is unsubstituted or substituted by one or more radicals from the group consisting of halogen, CN, (C$_1$–C$_8$)alkyl, (C$_1$–C$_8$)alkoxy, (C$_1$–C$_8$)haloalkyl, (C$_1$–C$_8$)haloalkylthio, (C$_1$–C$_8$) haloalkyloxy, and (C$_1$–C$_8$)alkoxyalkyloxy. Preferred radicals A are those in which a substituted R$^{14}$ is present in position 3 of the radical A, relative to the carbon atom which is attached to the group X in the formula (I).

Particularly preferred compounds of the formula (I) and/or salts thereof are those in which A is a substituted phenyl, pyridyl, thienyl or pyrazolyl radical of the following formula

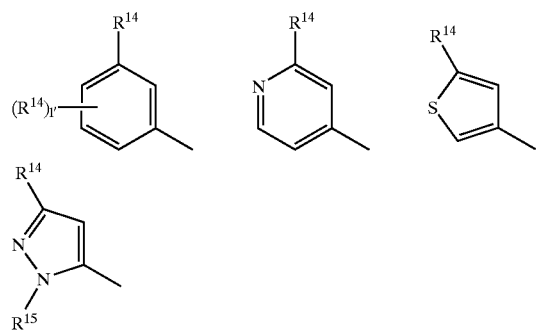

in which

R$^{14}$ is identical or different at each occurrence and is halogen, cyano or an optionally substituted (C$_1$–C$_8$)alkyl group, such as (C$_1$–C$_8$)haloalkyl, preferably CF$_3$ or cyano, R$^{15}$ is a (C$_1$–C$_8$)alkyl group, preferably methyl, and I' is an integer from 0 to 4, preferably 0 or 1; preferably, A is

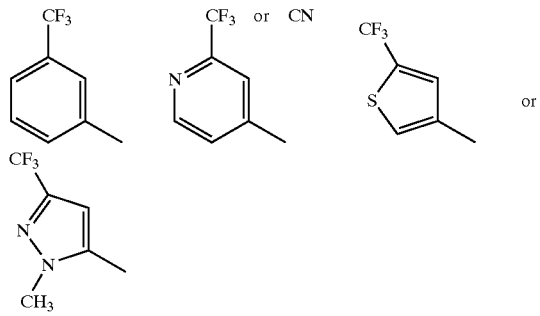

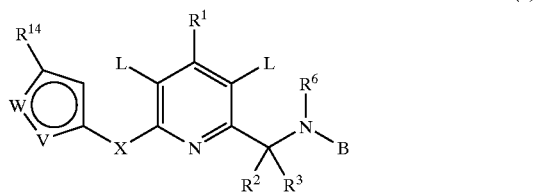

Very particular preference is given to compounds of the formula (I') and/or salts thereof $$(I')$$

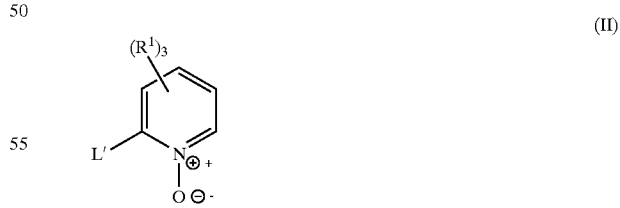

in which R$^1$, R$^2$, R$^3$, R$^6$, R$^{14}$, and X are as defined in formula (I), including the ranges of preference indicated above, L is identical or different at each occurrence and is H or halogen such as fluorine or chlorine, W-V together are N—CH—CH, S—CH, CH—CH—CH or N—N(CH$_3$), and B is an acyl radical such as [(C$_1$–C$_8$)alkyl]-carbonyl such as linear or branched [(C$_1$–C$_8$)-alkyl]-carbonyl or [(C$_3$–C$_6$) cycloalkyl]-carbonyl, or (C$_1$–C$_8$)alkylsulfonyl, such as linear or branched C$_1$–C$_8$-alkylsulfonyl or (C$_3$–C$_8$) cycloalkylsulfonyl, each of the radicals being unsubstituted or substituted by one or more radicals from the group consisting of halogen, especially fluorine or chlorine, CN, (C$_1$–C$_8$)-alkoxy, and (C$_1$–C$_8$)alkylthio.

The inventive compounds of the formula (I) can be prepared by known methods. The following are examples of syntheses that are of particular interest.

Starting from compounds of the formula (II)

$$(II)$$

in which the radicals R$^1$ are as defined for formula (I) and L' is a leaving group such as halogen or pseudohalogen or a group of the formula A—X—, where A and X are as defined for formula (I), it is possible, by a route known from the literature, first to alkylate the oxygen of the N-oxide and then react the product with cyanides to give nitriles of the formula (III) (see, for example, W. R. Fife and E. F. V. Seriven, Heterocycles 22, 2375 (1984) and literature cited therein),

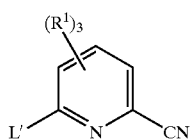

(III)

in which R¹ and L' are as defined for formula (II).

Pyridine N-oxides of the formula (II) can be prepared by various processes from suitably substituted pyridines. General synthesis methods are described, for example, in A. Albini and S. Pietra, Heterocyclic N-Oxides, CRS-Press, Inc., Boca Raton, USA, 1991.

As alkylating agents for compounds of the formula (II) it is possible with preference to use alkylhalogens or alkylpseudohalogens such as dimethyl sulfate or methyl iodide; examples of cyanides used are alkali metal or alkaline earth metal cyanides or cyanides of organic bases such as quaternary ammonium salts (see, for example, Ellman, Tetrahedron 41 (1985) 4941–4948).

Compounds of the formula (III) in which L' is a leaving group such as halogen or pseudohalogen can be reacted with compounds of the formula (IV) or salts thereof

A—X—H (IV)

where A and X are as defined for formula (I) to give compounds of the formula (III) (see, for example, U.S. Pat. Nos. 6,080,861, 6,130,188, and WO 94/22833 and literature cited therein) in which L' is a group of the formula A—X—. The compounds of the formula (III) in which L' is a group A—X— in which A, X, and R¹ are as defined for formula (I) can be converted by suitable reduction methods into the amino compounds of the formula (V).

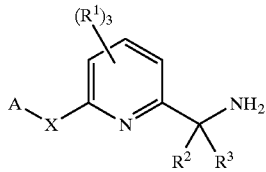

(V)

The reduction of nitriles to amines is diversely described in the literature (see, for example, Eugen Müller, Methoden der organischen Chemie (Houben-Weyl) volume XI/1, Nitrogen compounds II, p. 343 ff., Georg Thieme Verlag, Stuttgart 1957). Suitable hydrogenations include those catalyzed by noble metals, with palladium- and platinum-catalyzed reactions being of particular interest but reductions with Raney nickel also being possible.

Compounds of the formula (V) can be reacted with acylating reagents such as acid halides, isocyanates, carbamoyl chlorides, chloroformic esters, sulfonyl chlorides, sulfamoyl chlorides, sulfenyl chlorides or isothiocyanates to give compounds of the formula (I) in which R⁶=H, m=0 and A, X, R¹, R², R³, and B are as defined for formula (I). An entry point to general and specific chemical methods of acylation can be found, for example, in: Jerry March, Advanced Organic Chemistry (Reaction, Mechanisms and Structure 4$^{th}$ Edition, John Wiley & Sons, New York, 1992).

The compounds of the formula (I) in which R⁶ is, for example, an unsubstituted or substituted alkyl group are obtainable starting from compounds of the formula (V), which are alkylated with corresponding aldehydes, by reductive alkylation, to give compounds of the formula (VI) (ref.: Rylander Hydrogenation Methods, Academic Press, New York, 1985 pp. 92–93).

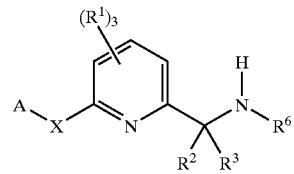

(VI)

Compounds of the formula (VI) are also obtainable by reducing the corresponding amides (see, for example, Example 3a) (see, for example, Gaylord, Reduction with Complex Metal Hydrides, Wiley, N.Y. 1956, pp. 322–373). Suitable for this purpose are, for example, borane complexes such as borane-tetrahydrofuran complexes or borane-dimethyl sulfide complexes (see, for example, Brown G. R, A. J. Foubister, J. Chem. Soc. Perk. T. 1 (8), 1401–1403 (1989)). The compounds of the formula (VI) can then be acylated, by known methods. Compounds of the formula (VI) where R⁶=optionally substituted alkenyl or alkynyl are available by reductive amination from compounds of the formula (III). The compounds of the formula (VI) can then be acylated by known methods to give compounds of the formula (I). Compounds of the formula (I) where R⁶=acyl are obtainable, for example, by known methods, by appropriate N-acylation of compounds of the formula (VI) where R⁶=H.

Compounds of the formula (I) where R⁶=hydroxyl and alkoxy are obtainable, for example, in accordance with the following reaction scheme:

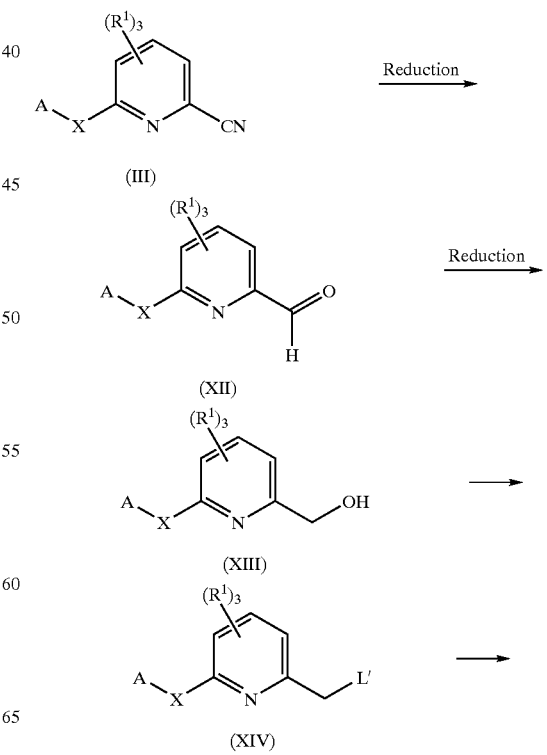

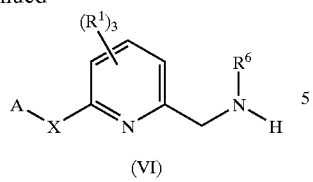

(VI)

Nitriles of the formula (III) can be converted reductively into aldehydes of the formula (XII) (see, for example, Miller, Biss, Schwartzmann; J. Org. Chem. 1970, 35, 858; or Jerry March. Advanced Organic Chemistry (Reaction, Mechanisms and Structure) $4^{th}$ Edition, John Wiley & Sons, New York, 1992, pp. 919, 920). The aldehydes of the formula (XII) can be reduced by known methods to the corresponding alcohols of the formula (XIII) (see, for example, Hudlicky, Reductions in Organic Chemistry; Ellis Horwood; Chichester 1984, pp. 96–129. For list of possible reagents see Larock; Comprehensive Organic Transformations VCH: New York, 1989, p. 993). The hydroxyl groups of the alcohols of the formula (XIII) can then be converted into leaving groups L'. As a leaving group it is possible, for example, to introduce halogens such as chlorine or bromine (see, for example, Wiley, Hershkowitz, Rein Chung, J. Am. Chem. Soc 1964, 86, 964 Schaefer, Weinberg J. Org. Chem. 1965, 30, 2635) or sulfonic ester groups such as tosylates or mesylates (see, for example, Crossland, Wells, Shiner; J. Am. Chem. Soc. 1971, 93, 4217). The compounds of the formula (XIV) can then be reacted with hydroxylamines or with O-alkylated hydroxylamines to give compounds of the formula (VI) in which $R^6$=hydroxyl or alkoxy. These reactions are preferably conducted in the presence of organic or inorganic bases in an inert solvent. The compounds of the formula (VI) where $R^6$ is other than H, and m=0 can then be acylated as indicated above for compounds of the formula (V) by known methods to give compounds of the formula (I).

Compounds of the formula (I) where m is 1 can be prepared, for example, as described below:

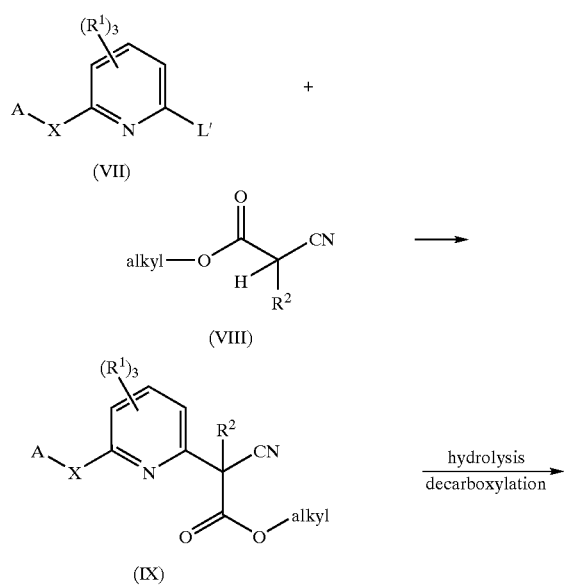

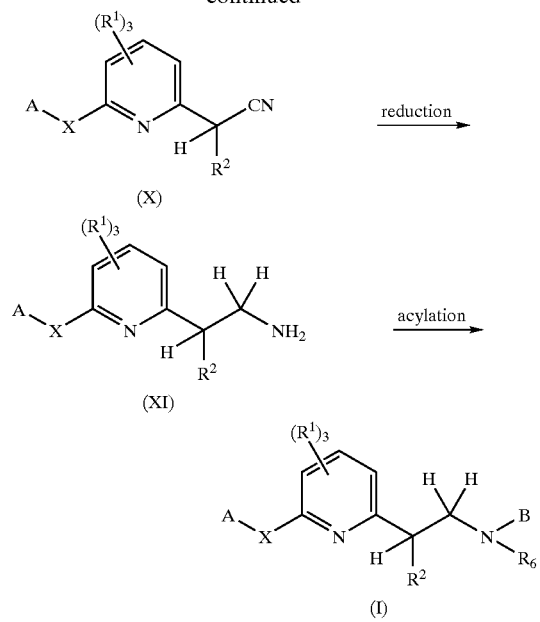

Compounds of the formula (VII) where A, X, and $R^1$ are as defined for formula (I) and L' is a leaving group such as halogen or pseudohalogen or is a substitutable heteroaryloxy group A—X can be reacted with unsubstituted or substituted alkyl cyanoacetates of the formula (VIII), $R^2$ as being defined for formula (I), preferably using $(C_1–C_6)$alkyl esters (ref.: N. Desideri F. Manna, J. Heterocycl. Chem., 25 (1), 333–335, 1988).

The ester groups of the compounds of the formula (IX) can then be converted into the free carboxylic acids. This can be done, for example, by basic hydrolysis of the alkyl esters or else may be carried out under acidic, hydrolysis conditions, with the carboxylic acid groups subsequently being decarboxylated under, for example, acidic conditions to give compounds of the formula (X) (ref.: N. Desideri; F. Manna, J. Heterocycl. Chem., 25 (1), 333–335, 1988). In formula (X) A, X, $R^1$, and $R^2$ have the definition indicated for formula (I).

The cyano compounds of the formula (X) that are obtainable in this way can be converted into the corresponding amino compounds of the formula (X) by means of suitable reduction methods, as already described for the preparation of the amines of the formula (V) from the nitrites of the formula (III). The amines of the formula (XI) that are obtainable in this way can be reacted in analogy to the amines of the formula (V) to give compounds of the formula (I) in which A, X, $R^1$, $R^2$, $R^6$, and B are as defined for formula (I).

Banks of compounds of the formula (I) and salts thereof which can be synthesized in accordance with the schemes indicated above may also be prepared in a parallelized way, which can be implemented manually, with partial automation or with full automation. It is possible, for example, to automate the implementation of the reaction, the workup, or the purification of the products and/or intermediates. By an automated synthesis of this kind is meant, overall, a procedure such as is described, for example, by S. H. DeWitt in "Annual Reports in Combinatorial Chemistry and Molecular Diversity: Automated Synthesis", volume 1, Escom 1997, pages 69 to 77.

For parallelized reaction implementation and workup it is possible to use a range of commercially available instruments, such as those offered, for example, by Stem Corporation, Woodrolfe Road, Tollesbury, Essex, England, H+P Labortechnik GmbH, Bruckmannring 28, 85764 Oberschleißheim, Germany or Radleys, Shire Hill, Saffron Walden, Essex, CB 11 :3AZ, England. For the parallelized purification of compounds of the formula (I) and salts thereof and/or of intermediates resulting during the production, chromatography apparatus, inter alia, is available, for example, from ISCO Inc., 4700 Superior Street, Lincoln, Nebr. 68504, USA. The apparatus listed leads to a modular procedure in which the individual worksteps are automated although it is necessary to carry out manual operations between the worksteps. This can be avoided by using partly or fully integrated automation systems where the respective automation modules are operated, for example, by robots. Automation systems of this kind can be purchased, for example, from Zymark Corporation, Zymark Center, Hopkinton, Mass. 01748, USA.

In addition to the methods described here, compounds of the formula (I) and salts thereof can be prepared completely or partly by means of solid-phase-aided methods. For this purpose, some or all of the synthesis intermediates or the intermediates of a synthesis adapted to suit the procedure in question are bound to a synthetic resin. Solid-phase-aided synthesis methods are described extensively in the specialist literature, for example, by Barry A. Bunin in "The Combinatorial Index", Academic Press, 1998.

The use of solid-phase-aided synthesis methods allows a series of protocols known from the literature, which in turn can be carried out manually or in automated fashion. For example, the teabag method (Houghten, U.S. Pat. No. 4,631, 211; Houghten et al., Proc. Natl. Acad. Sci, 1985, 82, 5131–5135) can be partly automated with products from IRORI 11149 North Torrey Pines Road. La Jolla. Calif. 92037. USA. Solid-phase-aided parallel syntheses are successfully automated, for example, by means of apparatus from Argonaut Technologies Inc., 887 Industrial Road, San Carlos, Calif. 94070, USA or MultiSynTech GmbH, Wullener Feld 4, 58454 Witten, Germany. Preparation in accordance with the processes described herein provides compounds of the formula (I) and salts thereof in the form of banks of substances which are referred to as libraries. The present invention further provides libraries comprising at least two compounds of the formula (I) and salts thereof.

The inventive compounds of the formula (I) and their salts, referred to collectively below as compounds of the formula (I) (of the invention), exhibit an excellent herbicidal activity against a broad spectrum of economically important monocotyledonous and dicotyledonous weed plants. Even perennial weeds which are difficult to control and which produce shoots from rhizomes, rootstocks or other perennial organs are effectively controlled by the compounds of the invention. The compounds of the invention can be applied, for example, pre-sowing, pre-emergence or post-emergence. Specific examples may be given of some representatives of the monocot and dicot weed flora which can be controlled by the compounds of the invention, without such naming being intended to represent any restriction to specific species.

On the side of the monocot weed species, for example, Avena, Lolium, Alopecurus, Phalaris, Echinochloa, Digitaria, Setaria, and also Bromus species and Cyperus species, from the annual group, and Agropyron, Cynodon, Imperata, and Sorghum, and also perennial Cyperus species, on the side of the perennial species, are effectively controlled.

In the case of dicot weed species, the activity spectrum extends to species such as, for example, Galium, Viola, Veronica, Lamium, Stellaria, Amaranthus, Sinapis, Ipomoea, Matricaria, Abutilon, and Sida, on the annual side, and also Convolvulus, Cirsium, Rumex and Artemisia among the perennial weeds. Weed plants which occur under the specific growing conditions in rice, such as Echinochloa, Sagittaria, Alisma, Eleocharis, Scirpus, and Cyperus, for example, are likewise controlled to outstanding effect by the compounds of the invention.

Where the compounds of the invention are applied to the soil surface prior to germination, then either the weed seedlings are prevented completely from emerging or else the weeds grow until they reach the cotyledon stage but then their growth stops and eventually, after three to four weeks have elapsed, they die off completely.

Where the compounds of the invention are applied post-emergence to the green parts of the plants, growth also stops sharply a very short time after treatment, and the weed plants remain at the developmental stage they were in at the time of application, or they die off completely after a certain time, so that weed competition, which is harmful for the crop plants, is eliminated sustainedly and at a very early stage.

Although the compounds of the invention exhibit an excellent herbicidal activity against monocot and dicot weeds, there is negligible if any damage to plants of economically important crops, examples including dicotyledonous crops such as soya, cotton, oilseed rape, sugar beet, especially soya, or gramineous crops such as wheat, barley, rye, rice or corn. For these reasons, the present compounds are highly suitable for selectively controlling unwanted plant growth in plantings of agricultural crops or decorative plants.

In addition, the compounds of the invention have outstanding growth-regulating properties in crop plants. They engage in the plant metabolism in a regulating manner and can thus be employed for the targeted control of plant constituents and for facilitating harvesting, such as for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced thereby or prevented completely. Owing to their herbicidal and plant growth regulatory properties, the active compounds can also be employed for controlling harmful plants in crops of known or still to be developed genetically engineered plants. The transgenic plants generally have particular advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage stability, composition and to specific ingredients of the harvested product. Thus, transgenic plants having an increased starch content or a modified quality of the starch or those having a different fatty acid composition of the harvested product are known.

The use of the compounds of the formula (I) according to the invention or their salts in economically important transgenic crops of useful and ornamental plants, for example of cereals, such as wheat, barley, rye, oats, millet, rice, manioc and corn, or else in crops of sugar beet, cotton, soy, oilseed rape, potato, tomato, pea and other vegetable species is preferred.

The compounds of the formula (I) can preferably be used as herbicides in crops of useful plants which are resistant or which have been made resistant by genetic engineering toward the phytotoxic effects of the herbicides.

Conventional ways of preparing novel plants which have modified properties compared to known plants comprise, for example, traditional breeding methods and the generation of mutants. Alternatively, novel plants having modified properties can be produced with the aid of genetic engineering methods (see, for example, EP-A-0221044, EP-A-0131624). For example, there have been described several cases of genetically engineered changes in crop plants in order to modify the starch synthesized in the plants (for example WO 92/11376, WO 92/14827 and WO 91/19806), transgenic crop plants which are resistant to certain herbicides of the glufosinate type (cf., for example, EP-A-0242236, EP-A-0242246) or glyphosate type (WO 92/00377), or of the sulfonylurea type (EP-A-0257993, U.S. Pat. No. 5013659), transgenic crop plants, for example cotton, having the ability to produce Bacillus thuringiensis toxins (Bt toxins) which impart resistance to certain pests to the plants (EP-A-0142924, EP-A-0193259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423–431).

In order to carry out such genetic engineering manipulations, it is possible to introduce nucleic acid molecules into plasmids which allow a mutagenesis or a change in the sequence to, occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end, it is possible to employ both DNA molecules which comprise the entire coding sequence of a gene product, including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cell. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated to whole plants using known techniques. The transgenic plants can in principle be plants of any desired plant species, i.e. both monocotyledonous and dicotyledonous plants.

In this manner, it is possible to obtain transgenic plants which have modified properties by overexpression, suppression or inhibition of homologous (=natural) genes or gene sequences or by expression of heterologous (=foreign) genes or gene sequences.

The compounds (I) according to the invention can preferably be used in transgenic crops which are resistant to herbicides selected from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crop is resistant, and an effect on the growth and the yield of the transgenic crop plants.

The invention therefore also provides for the use of the compounds (I) according to the invention as herbicides for controlling weed plants in transgenic crop plants.

The compounds according to the invention can be applied in the customary formulations in the form of wettable powders, emulsifiable concentrates, sprayable solutions, dusts or granules. The invention therefore also provides herbicidal and plant-growth-regulating compositions comprising compounds of the formula (I).

The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes.

These individual formulation types are known in principle and are described, for example, in Winnacker-Küchler, "Chemische Technologie" [Chemical Technology], Volume 7, C. Hauser Verlag Munich, 4th edition 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and other additives, are likewise known and are described, for example, in: Watkins, "Handbook of Insecticide Dust Diluents and Carriers", 2nd ed., Darland Books, Caldwell N. J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents". Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th edition 1986.

Based on these formulations it is also possible to produce combinations with other pesticidally active substances, for example insecticides, acaricides, herbicides and fungicides, and also with safeners, fertilizers and/,or growth regulators, for example in the form of a ready-mix or tank mix.

Wettable powders are preparations which are uniformly dispersible in water and which, in addition to the active compound and as well as a diluent or inert substance, also contain surfactants of ionic and/or nonionic type (wetting agents, dispersants), for example polyethoxylated alkyl phenols, polyethoxylated fatty alcohols, polyethoxylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are finely ground, for example in customary apparatuses such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th ed., McGraw-Hill, New York 1973. pp. 8–57.

For further details on the formulation of crop protection products, see for example G. C. Klingman, "Weed Control as a Science", John Wiley and Sons., Inc., New York, 1961, pages 81–96 and J. D. Freyer, S. A. Evans, "Weed Control Handbook", 5th ed., Blackwell Scientific Publications, Oxford, 1968, pages 101–103.

The agrochemical formulations generally contain from 0.1 to 99% by weight, in particular from 0.1 to 95% by weight, of active compound of the formula (I) and/or salts thereof.

In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules, the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Suitable active compounds which can be combined with the active compounds according to the invention in mixed formulations or in a tank mix are, for example, known active compounds such as herbicides, insecticides, fungicides or safeners, as described, for example, in Weed Research 26, 441–445 (1986), or in "The Pesticide Manual", 11th edition, The British Crop Protection Council and the Royal Soc. of Chemistry, 1997, and in the literature cited therein. For example, the following active compounds may be mentioned as herbicides which are known and which can be combined with the compounds of the formula (I) (Note: the compounds are either referred to by the "common name" in accordance with the International Organization for Standardization (ISO) or by the chemical names, if appropriate together with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]-amino]-oxy]-acetic acid and its methyl ester; alachlor; alloxydim; ametryn; amidosulfuron; amitrol; AMS, i.e. ammonium sulfamate; anilofos; asulam; atrazine; azafenidin; azimsulfuron (DPX-A8947); aziprotryn; barban; BAS 516 H. i.e. 5-fluoro-2-phenyl-4H-3,1-benzoxazin-4-one; BAS 620 H; BAS 65400H; BAY FOE 5043; benazolin; benfluralin; benfuresate; bensulfuron-methyl; bensulide; bentazone; benzofenap; benzofluor; benzoylprop-ethyl; benzthiazuron; bialaphos; bifenox; bispyribac-Na; bromacil; bromobutide; bromofenoxim; bromoxynil; bromuron; buminafos; busoxinone; butachlor; butamifos; butenachlor; buthidazole; butralin; butroxydim; butylate; cafenstrole (CH-900); caloxydim; carbetamide; cafentrazone-ethyl; CDAA, i.e. 2-chloro-N,N-di-2-propenylacetamide; CDEC, i.e. 2-chloroallyl diethyidithiocarbamate; chlomethoxyfen; chloramben; chlorazifop-butyl; chlorbromuron; chlorbufam; chlorfenac; chlorflurecol-methyl; chloridazon; chlorimuronethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cloransulammethyl; cumyluron (JC 940); cyanazine; cycloate; cyclosulfamuron (AC 104); cycloxydim; cycluron; cyhalofop and its ester derivatives (for example butyl-ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diclosulam, i.e., N-(2,6-dichlorophenyl)-5-ethoxy-7-fluoro-[1,2,4]triazolo [1,5-c]pyrimidine-2-sulfonamide; diethatyl; difenoxuron; difenzoquat; diflufenican; diflufenzopyr (BAS 654 00H); dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC4243); flupyrsulfuron-methyl-sodium fluridone; flurochloridone; fluroxypyr; flurtamone; fluthiacet-methyl; fomesafen; foramsulfuron and its salts; fosamine; furyloxyfen; glufosinate; glyphosate; halosafen; halosulfuron and its esters (for example the methyl ester, NC-319); haloxyfop and its esters; haloxyfop-P (=R-haloxyfop) and its esters; hexazinone; imazamethabenz-methyl; imizamox; imazapyr; imazaquin and salts such as the ammonium salt; imazamethapyr; imazethapyr; imazosulfuron; indanofan (MK-243), iodosulfuron and its salts and esters, such as iodosulfuron-methyl-sodium; ioxynil; isocarbamid; isopropalin; isoproturon; isouron; isoxaben; isoxaflutole; isoxapyrifop; karbutilate; lactofen; lenacil; linuron; MCPA; MCPB; mecoprop; mefenacet; mefluidid; mesosulfuron and its salts and esters, such as mesosulfuron-methyl; metamitron; metazachlor; methabenzthiazuron; metham; methazole; methoxyphenone; methyl-dymron; metabenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methyipentanamide; naproanilide; napropamide; naptalam; NC 310, i.e, 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazone; oxasulfuron; oxaziclomefone (MY-100); oxyfluorfen; paraquat; pebulate; pendimethalin; pentoxazone (KPP-314) perfluidone: p henisopham; phenmedipham; picloram: piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyroflufen-ethyl; pyrazolinate; pyrazon; pyrazosulfuron-ethyl; pyrazoxyfen; pyribenzoxim (LGC-40836); pyributicarb; pyridate; pyriminobac-methyl; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazon (FMC-97285, F-6285); sulfazuron; sulfometuron-methyl; sulfosate (ICI-A0224); sulfosulfuron; TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thifensulfuron-methyl; thiobencarb; tiocarbazil; tralkoxydim; tri-allate; triasulfuron; triaziflam; triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)phenyl]-1H-tetrazole; JTC-101; UBH-509; D-489; LS 82–556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

The active compounds of the invention can also be used in combination with safeners. For use, the formulations which are present in commercially available form are, if appropriate, diluted in the customary manner, for example using water in the case of wettable powders, emulsifiable concentrates, dispersions and water-dispersible granules. Preparations in the form of dusts, granules for soil application or broadcasting and sprayable solutions are usually not further diluted with other inert substances prior to use.

The required application rate of the compounds of the formula (I) varies with the external conditions, such as temperature, humidity, the nature of the herbicide used and the like. It can vary within wide limits, for example between 0.001 and 10.0 kg/ha or more of active substance, but it is preferably between 0.005 and 5 kg/ha.

A. Chemical Examples

Abbreviations:
The % ages and proportions are by weight unless specified otherwise.
in vacuo=under reduced pressure
h=hours(s)

EXAMPLE 1

2-(1-Methyl-3-trifluoromethylpyrazol-5-yloxy)-6-(but-2-enoyl-aminomethyl)-pyridine 1a) 2-(1-Methyl-3-trifluoromethylpyrazol-5-yloxy)-6-cyanopyridine 4.00 g (240 mmol) of 1-methyl-3-(trifluoromethyl)-2-pyrazol-2-one were introduced into 40 ml of sulfolane under a nitrogen atmosphere and at room temperature 2.70 g (24.0 mmol) of potassium tert-butoxide were added in portions to this initial charge. Then 2.56 g (18.5 mmol) of 2-chloro-6-cyanopyridine were added and the solution was heated at 130° C. for 3 h, cooled to room temperatured and poured into ice-water. The precipitate was filtered off, washed repeatedly with water and then dried.

Yield 4.26 g (86%); melting point 87° C.

1b) 2-(1-Methyl-3-trifluoromethylpyrazol-5-yloxy)-6-(aminomethyl)-pyridine 7.00 g (26.1 mmol) of 2-(1-methyl-3-trifluoromethylpyrazol-5-yloxy)-6-cyanopyridine were dissolved in 150 ml of glacial acetic acid, admixed with 1.40 g of Pd(OH)$_2$, 20% on charcoal, and hydrogenated under a hydrogen overpressure of 17 bar. After 2 h, the catalyst was removed by filtration and the filtrate was concentrated by evaporation. The residue was taken up in water, admixed with 20 ml of 2 N HCl and subjected to multiple extraction with ethyl acetate. The aqueous phase was subsequently adjusted to a pH of 10 using 2 N NaOH and then subjected to multiple extraction with ethyl acetate. The combined organic extracts were then dried using MgSO$_4$, filtered and concentrated.

Yield 2.58 g (34%); melting point: 44° C.

1c) 2-(1-Methyl-3-trifluoromethylpyrazol-5-yloxy)-6-(but-2-enoyl-aminomethyl)-pyridine 0.100 g (0.368 mmol) of 2-(1-methyl-3-trifluoromethylpyrazol-5-yloxy)-6-(aminomethyl)-pyridine was introduced in 5 ml of methylene chloride together with 71.1 mg (0.55 mmol) of diisopropylethylamine, at room temperature 46.1 mg (0.44 mmol) of but-2-enoyl chloride were added and the mixture was stirred at room temperature for 3 h. The crude product was concentrated, subjected to extraction with 1 N HCl and ethyl acetate and then filtered over a silica gel bed. The filtrate was concentrated. The residue was crystalline.

Yield 0.059 g (47%); melting point 75° C.

EXAMPLE 2

2-(1-Methyl-3-trifluoromethylpyrazol-5-yloxy)-6-(formylaminomethyl)-pyridine 0.100 g (0.368 mmol) of 2-(1-methyl-3-trifluoromethyl-pyrazol-5-yloxy)-6-(aminomethyl)-pyridine in 5 ml of ethyl formate was heated at reflux for 3 h. The solution was then filtered through a cartridge packed with 3 g of silica gel and this cartridge was rinsed out with ethyl acetate. The filtrate was concentrated.

Yield 0.101 g (91%); melting point 84° C. NMR shows the expected signals:

1H NMR (CDCl$_3$/TMS): δ (ppm)=3.80 (s, 3H, N—CH$_3$), 4.57 (d, 2H, J=7 Hz, N—CH$_2$—), 6.26 (s, 1H, C—H pyrazole), 6.30 (s, br,1H, N—H), 6.95 (d, 1H, J=8 Hz, pyridine C—H), 7.15 (d, 1H, J=8 Hz, pyridine C—H), 7.78 (t, 1H, J=8 Hz, pyridine C—H), 8.27 (s, 1H, H—CO).

EXAMPLE 3

3a) 2-(1-Methyl-3-trifluoromethylpyrazol-5-yloxy)-6-(methylaminomethyl)-pyridine 4.40 g (14.7 mmol) of 2-(1-methyl-3-trifluoromethylpyrazol-5-yloxy)-6-(formylaminomethyl)-pyridine were dissolvej in 45 ml of anhydrous THF under an inert gas atmosphere and at 0° C. 4.17 ml (44.0 mmol) of borane dimethylsulfide complex were added to the solution. The mixture was heated at 50° C. for 2.5 h. After cooling to room temperature, the reaction solution was admixed with 100 ml of 2 N HCl, stirred for 1 h and then extracted with ethyl acetate. The aqueous phase was rendered alkaline with 2 N NaOH and subjected to repeated extraction with ethyl acetate. The extracts were dried over MgSO$_4$ and concentrated to dryness.

Yield 2.22 g of oil; NMR showed the expected signals:

1H NMR (DMSO-d6/TMS): δ (ppm)=2.25 (s, 3H, N—CH$_3$ pyrazole 3.3 (s br., 1H, N—H (together with H$_2$O)), 3.63 (s, 2H, CH$_2$—N) 3.75 (s, 3H, CH$_3$—N), 6.60 (s, 1H, C—H pyrazole), 7.08 (d, 1H, J=8 Hz, C—H pyridine), 7.30 (d, 1H, J=8 Hz, C—H pyridine), 7.93 (t, 1H, J=8 Hz, C—H pyridine).

3b) 2-(1-Methyl-3-trifluoromethylpyrazol-5-yloxy)-6-[(N-isopropylcarbonyl-N-methyl)-aminomethyl]-pyridine 0.100 g (0.349 mmol) of 2-(1-methyl-3-trifluoromethyl-pyrazol-5-yloxy)-6-(methylaminomethyl)-pyridine was introduced in 4.0 ml of methylene chloride together with 68 mg (0.53 mmol) of diisopropylethylamine, and 45 mg (0.42 mmol) of isobutyryl chloride were added. After stirring at room temperature for 45 minutes the reaction solution was introduced into 1 N HCl and subjected to extraction with methylene chloride. The organic phase was concentrated to give an oil.

Yield 0.096 g (77%); NMR showed the expected signals:

The spectrum shows two conformers, which are described as A (75%) and B (25%):

Conformer A: 1H NMR (CDCl$_3$/TMS) δ (ppm)=1.11 (d, 6H, J=8 Hz, (CH$_3$)$_2$—CH), 2.82 (sept, 1H, J=8 Hz, (CH$_3$)$_2$—CH), 3.06 (s, 3H, CO—N—CH$_3$), 3.75 (s, 3H, N—CH$_3$ pyrazole), 4.53 (s, 2H, CH$_2$—N), 6.28 (s, 1H, C—H pyrazole), 6.90 (d, 1H, J=8 Hz, C—H pyridine), 7.07 (d, 1H, J=8 Hz, C—H pyridine), 7.73 (t, 1H, J=8 Hz, C—H pyridine).

Conformer B: 1H NMR (CDCl$_3$/TMS) δ (ppm)=1.07 (d, 6H, J=8 Hz, (CH$_3$)$_2$CH), 2.75 (sept. 1H, J=8 Hz, (CH$_3$)$_2$—CH), 2.96 (s, 3H, CO—N—CH$_3$), 3.81 (s, 3H, N—CH$_3$ pyrazole), 4.53 (s, 2H, CH$_2$—N), 6.33 (s, 1H, C—H pyrazole), 6.97 (d, 1H, J=8 Hz, C—H pyridine), 6.99 (d,1H, J=8 Hz, C—H pyridine), 7.80 (t, 1H, J=8 Hz, C—H pyridine).

EXAMPLE 4

2-(1-Methyl-3-trifluoromethylpyrazol-5-yloxy)-6-[(N-methylsulfonyl-N-ethyl)-aminomethyl]-pyridine 0.080 g (0.28 mmol) of 2-(1-methyl-3-trifluoromethylpyrazol-5-yloxy)-6-(methylaminomethyl)-pyridine was introduced in 5 ml of methylene chloride together with 0.108 g (0.837 mmol) of diisopropylethylamine, and 0.096 g (0.837 mmol) of methanesulfonyl chloride was added. After stirring at room temperature for 4 hours the mixture was extracted with 2 N NaOH and the organic phase was washed until neutral and then dried over Na$_2$SO$_4$ and concentrated by evaporation. Chromatographic purification (silica gel/ethyl acetate) gave an oil.

Yield 0.088 g (82%); NMR showed the expected signals:

1H NMR (CDCl$_3$/TMS) δ (ppm)=2.74 (s, 3H, CH$_3$—N—SO$_2$), 2.83 (s, 3H, SO$_2$—CH$_3$), 3.78 (s, 3H, N—CH$_3$ pyrazole), 4.39 (s, 2H, CH$_2$—N), 6.30 (s, 1H C—H pyrazole), 7.00 (d, 1H, J=8 Hz, CH pyridine), 7.26 (d,1H, J=8 Hz, CH pyridine), 7.80 (t, 1H, CH pyridine).

EXAMPLE 5

5a) 2-(3-Trifluoromethylphenyloxy)-6-cyanopyridine 4.00 g (28.9 mmol) of 2-chloro-6-cyanopyridine were introduced together with 9.57 g (69.3 mmol) of potassium /carbonate in 20 ml of anhydrous DMF, and 5.62 g (34.6 mmol) of 3-hydroxybenzotrifluoride were added. After 10 h of stirring at 90° C., $H_2O$ was added and the mixture was subjected to repeated extraction with ethyl acetate. The organic phase was then washed twice with water, dried over $MgSO_4$ and concentrated.

Yield (oil): 6.24 g (82%); NMR showed the expected signals:

1H NMR ($CDCl_3$/TMS) δ (ppm)=7.20 (d, 1H, J=8 Hz, aromatic H), 7.38 (mc, 1H, aromatic H), 7.4–7.6 (m, 4H, aromatic H), 7.83 (t, 1H, J=8 Hz, CH pyridine).

5b) 2-(3-Trifluoromethylphenyloxy)-6-(aminomethyl)-pyridine 3.00 g (11.4 mmol) of 2-(3-trifluoromethylphenyloxy)-6-cyanopyridine were dissolved in 120 ml of acetic acid, 300 mg of Pd $(OH)_2$, 20% on charcoal, were added, and the mixture was hydrogenated at a hydrogen pressure of 17 bar for 3 h at room temperature. The catalyst was then removed by filtration, the organic phase was concentrated and the residue was taken up in water. This solution was washed with ethyl acetate, then adjusted to a pH of 10 using 2 N NaOH, and subjected to repeated extraction with ethyl acetate. The combined organic extracts were dried over $MgSO_4$ and then evaporated to dryness.

Yield 1.02 g (67%); NMR showed the expected signals:

1H NMR ($CDCl_3$/TMS) δ (ppm)=1.7 (s, br, 2H, $NH_2$), 3,83 (s, 2H, $CH_2$—N), 6.78 (d, 1H, J=8 Hz, CH pyridine), 7.02 (d, 1H, J=8 Hz, CH pyridine), 7.35 (m, 1H, C—H-phenyl) 7.4–7.55 (m, 3H phenyl-H) 7.67 (t; 1H J=8 Hz, CH pyridine).

5c) 2-(3-Trifluorophenyloxy)-6-(dichloroacetyl-aminomethyl)-pyridine 0.100 g (0.373 mmol) of 2-(3-trifluorophenyloxy)-6-(aminomethyl)pyridine was introduced in 4.0 ml of methylene chloride together with 0.072 g (0.56 mmol) of diisopropylethylamine, and 0.066 g (0.450 mmol) of dichloroacetyl chloride was added. After stirring at room temperature for 3 hours the mixture was extracted with 1 N HCl and the organic phase was dried and concentrated by evaporation. The residue was crystalline.

Yield 0.70 g (50%); melting point 70.8° C.

The compounds of the formula (I″) and (I‴) listed in tables 1 and 2 below can be obtained in analogy to examples 1–5.

TABLE 1

(I″)

| Example | A | B | $R^1$ | $R^6$ | Melting point [° C.] |
|---|---|---|---|---|---|
| 6 | 1-$CH_3$-3-$CF_3$-pyrazol-5-yl | $CH_3$—CHCl—CO | H | H | 96 |
| 7 | 1-$CH_3$-3-$CF_3$-pyrazol-5-yl | structure 1 | " | " | oil |
| 8 | 1-$CH_3$-3-$CF_3$-pyrazol-5-yl | 3-$NO_2$-4-Cl-benzyl | " | " | oil |
| 9 | 1-$CH_3$-3-$CF_3$-pyrazol-5-yl | 4-tert-butylbenzoyl | " | " | oil |
| 10 | 1-$CH_3$-3-$CF_3$-pyrazol-5-yl | 2,4,6-trifluorobenzoyl | " | " | 144 |
| 11 | 1-$CH_3$-3-$CF_3$-pyrazol-5-yl | 3,4-difluorobenzoyl | " | " | |
| 12 | 1-$CH_3$-3-$CF_3$-pyrazol-5-yl | 3-trifluoromethylbenzoyl | " | " | |
| 13 | 1-$CH_3$-3-$CF_3$-pyrazol-5-yl | 3,4-dichlorobenzoyl | " | " | 132.5 |
| 14 | 1-$CH_3$-3-$CF_3$-pyrazol-5-yl | $C_2H_5$—O—CO—$(CH_2)_3$—CO | " | " | 59 |
| 15 | 1-$CH_3$-3-$CF_3$-pyrazol-5-yl | $CH_3$—$(CH_2)_7$—CO | " | " | 89 |
| 16 | 1-$CH_3$-3-$CF_3$-pyrazol-5-yl | phenyl-CH=CH—CO | " | " | 130 |
| 17 | 1-$CH_3$-3-$CF_3$-pyrazol-5-yl | Cl—$(CH_2)_4$—CO | " | " | 101 |
| 18 | 1-$CH_3$-3-$CF_3$-pyrazol-5-yl | Cl—$(CH_2)_3$—CO | " | " | 81 |
| 19 | 1-$CH_3$-3-$CF_3$-pyrazol-5-yl | $CH_3$—$CH_2$—CO | " | " | 85 |
| 20 | 1-$CH_3$-3-$CF_3$-pyrazol-5-yl | $(CH_3)_2$C=CH—CO | " | " | 75.8 |

TABLE 1-continued (structure shown: pyridine with A-O at position 2, R¹ at position 4, and CH₂-N(R⁶)-B at position 6) (I'')

| Example | A | B | R¹ | R⁶ | Melting point [° C.] |
|---|---|---|---|---|---|
| 21 | 1-CH₃-3-CF₃-pyrazol-5-yl | CH₂=CH—CO | " | " | 117.1 |
| 22 | 1-CH₃-3-CF₃-pyrazol-5-yl | ClH₂C—CO | " | " | 86.2 |
| 23 | 1-CH₃-3-CF₃-pyrazol-5-yl | CH₃—CO | " | " | 97.4 |
| 24 | 1-CH₃-3-CF₃-pyrazol-5-yl | (CH₃)₂CH—CO | " | " | 71 |
| 25 | 1-CH₃-3-CF₃-pyrazol-5-yl | CH₃—O—CH₂—CO | " | " | 94 |
| 26 | 1-CH₃-3-CF₃-pyrazol-5-yl | (CH₃)₂CF—CO | " | " | 93.4 |
| 27 | 1-CH₃-3-CF₃-pyrazol-5-yl | Cl₂HC—CO | " | " | 111.5 |
| 28 | 1-CH₃-3-CF₃-pyrazol-5-yl | CH₃—CHF—CO | " | " | 83.9 |
| 29 | 1-CH₃-3-CF₃-pyrazol-5-yl | CF₃—CO | " | " | 111.9 |
| 30 | 1-CH₃-3-CF₃-pyrazol-5-yl | cyclopropyl-CO | " | " | 108 |
| 31 | 1-CH₃-3-CF₃-pyrazol-5-yl | cyclobutyl-CO | " | " | 102.7 |
| 32 | 1-CH₃-3-CF₃-pyrazol-5-yl | 2-furan-CO | " | " | 128.2 |
| 33 | 1-CH₃-3-CF₃-pyrazol-5-yl | 2-thienyl-CO | " | " | 126.5 |
| 34 | 1-CH₃-3-CF₃-pyrazol-5-yl | CF₃—CH₂—CO | " | " | 129.5 |
| 35 | 1-CH₃-3-CF₃-pyrazol-5-yl | (CF₃)₂CH—CO | " | " | |
| 36 | 1-CH₃-3-CF₃-pyrazol-5-yl | tert-butyl-CO | " | " | oil |
| 37 | 1-CH₃-3-CF₃-pyrazol-5-yl | 3-cyanobenzoyl | " | " | |
| 38 | 1-CH₃-3-CF₃-pyrazol-5-yl | (CH₃)₂CH—CH₂—CO | " | " | |
| 39 | 1-CH₃-3-CF₃-pyrazol-5-yl | tert-butyl-CH₂—CO | " | " | |
| 40 | 1-CH₃-3-CF₃-pyrazol-5-yl | (C₂H₅)₂CH—CO | " | " | |
| 41 | 1-CH₃-3-CF₃-pyrazol-5-yl | CH₃—CO—O—CH₂—CO | " | " | |
| 42 | 1-CH₃-3-CF₃-pyrazol-5-yl | CH₃—O—CO—CH₂—CO | " | " | |
| 43 | 1-CH₃-3-CF₃-pyrazol-5-yl | benzyl-CO | " | " | |
| 44 | 1-CH₃-3-CF₃-pyrazol-5-yl | CL—CH₂—(CH₃)₂C—CO | " | " | |
| 45 | 1-CH₃-3-CF₃-pyrazol-5-yl | 4-fluorobenzoyl | " | " | |
| 46 | 1-CH₃-3-CF₃-pyrazol-5-yl | 2-methoxybenzoyl | " | " | |
| 47 | 1-CH₃-3-CF₃-pyrazol-5-yl | 4-methoxybenzoyl | " | " | |
| 48 | 1-CH₃-3-CF₃-pyrazol-5-yl | 4-fluorobenzyl-CO | " | " | |
| 49 | 1-CH₃-3-CF₃-pyrazol-5-yl | 6-Cl-pyridine-3-CO | " | " | |
| 50 | 1-CH₃-3-CF₃-pyrazol-5-yl | pyridine-4-CO | " | " | |
| 51 | 1-CH₃-3-CF₃-pyrazol-5-yl | CH₃—O—CO—(CH₂)₄—CO | " | " | |
| 52 | 1-CH₃-3-CF₃-pyrazol-5-yl | 2,4,6-trimethylbenzoyl | " | " | |
| 53 | 1-CH₃-3-CF₃-pyrazol-5-yl | 4-nitrobenzoyl | " | " | |

TABLE 1-continued (I'')

| Example | A | B | R$^1$ | R$^6$ | Melting point [° C.] |
|---|---|---|---|---|---|
| 54 | 1-CH$_3$-3-CF$_3$-pyrazol-5-yl | 2,2-dichlorocyclopropyl-CO | " | " | oil |
| 55 | 1-CH$_3$-3-CF$_3$-pyrazol-5-yl | 2,2-difluorocyclopropyl-CO | " | " | |
| 56 | 1-CH$_3$-3-CF$_3$-pyrazol-5-yl | 2-methylcyclopropyl-CO | " | " | |
| 57 | 1-CH$_3$-3-CF$_3$-pyrazol-5-yl | 1-methylcyclopropyl-CO | " | " | oil |
| 58 | 1-CH$_3$-3-CF$_3$-pyrazol-5-yl | 3-(CF$_3$—O)-benzoyl | " | " | |
| 59 | 1-CH$_3$-3-CF$_3$-pyrazol-5-yl | 2,5-DiCF$_3$-benzoyl | " | " | |
| 60 | 1-CH$_3$-3-CF$_3$-pyrazol-5-yl | 2-Br-5-methoxybenzoyl | " | " | |
| 61 | 1-CH$_3$-3-CF$_3$-pyrazol-5-yl | 1-CH$_3$-2,2-dichlorocyclopropyl-CO | " | " | |
| 62 | 1-CH$_3$-3-CF$_3$-pyrazol-5-yl | 2,2,3,3-tetramethyl-cyclopropyl-CO | " | " | oil |
| 63 | 1-CH$_3$-3-CF$_3$-pyrazol-5-yl | 2,3,4,5,6-pentafluorobenzoyl | " | " | |
| 64 | 1-CH$_3$-3-CF$_3$-pyrazol-5-yl | structure 2 | " | " | |
| 65 | 1-CH$_3$-3-CF$_3$-pyrazol-5-yl | C$_2$H$_5$—O—CO—CO | " | " | 59.7 |
| 66 | 1-CH$_3$-3-CF$_3$-pyrazol-5-yl | CH$_3$—O—CO | " | " | 81 |
| 67 | 1-CH$_3$-3-CF$_3$-pyrazol-5-yl | CH$_3$—CH$_2$—O—CO | " | " | 81.1 |
| 68 | 1-CH$_3$-3-CF$_3$-pyrazol-5-yl | benzyl-O—CO | " | " | 87.4 |
| 69 | 1-CH$_3$-3-CF$_3$-pyrazol-5-yl | C$_4$H$_9$—O—CO | " | " | |
| 70 | 1-CH$_3$-3-CF$_3$-pyrazol-5-yl | (CH$_3$)$_2$CH—CH$_2$—O—CO | " | " | 75.1 |
| 71 | 1-CH$_3$-3-CF$_3$-pyrazol-5-yl | (CH$_3$)$_2$CH—O—CO | " | " | 101.7 |
| 72 | 1-CH$_3$-3-CF$_3$-pyrazol-5-yl | (CH$_3$)$_2$C—O—CO | " | " | |
| 73 | 1-CH$_3$-3-CF$_3$-pyrazol-5-yl | C$_3$H$_7$—O—CO | " | " | oil |
| 74 | 1-CH$_3$-3-CF$_3$-pyrazol-5-yl | 4-NO$_2$-benzyl-O—CO | " | " | |
| 75 | 1-CH$_3$-3-CF$_3$-pyrazol-5-yl | CH$_2$=CH—CH$_2$—O—CO | " | " | |
| 76 | 1-CH$_3$-3-CF$_3$-pyrazol-5-yl | cyclopentyl-O—CO | " | " | |
| 77 | 1-CH$_3$-3-CF$_3$-pyrazol-5-yl | CF$_3$—CH$_2$—O—CO | " | " | |
| 78 | 1-CH$_3$-3-CF$_3$-pyrazol-5-yl | (CH$_3$)$_2$N—CO | " | " | 92 |
| 79 | 1-CH$_3$-3-CF$_3$-pyrazol-5-yl | C$_2$H$_5$—NH—CO | " | " | 142 |
| 80 | 1-CH$_3$-3-CF$_3$-pyrazol-5-yl | 2,4-difluorophenyl-NH—CO | " | " | 168 |
| 81 | 1-CH$_3$-3-CF$_3$-pyrazol-5-yl | 3-fluorophenyl-NH—CO | " | " | 180 |
| 82 | 1-CH$_3$-3-CF$_3$-pyrazol-5-yl | H$_3$C—NH—CO | " | " | |
| 83 | 1-CH$_3$-3-CF$_3$-pyrazol-5-yl | CH$_2$=CH—CH$_2$—NH—CO | " | " | |
| 84 | 1-CH$_3$-3-CF$_3$-pyrazol-5-yl | (CH$_3$)$_2$CH—NH—CO | " | " | |
| 85 | 1-CH$_3$-3-CF$_3$-pyrazol-5-yl | (CH$_3$)$_2$C—NH—CO | " | " | |
| 86 | 1-CH$_3$-3-CF$_3$-pyrazol-5-yl | (CH$_3$)$_2$CH—CH$_2$—NH—CO | " | " | |

TABLE 1-continued (I")

| Example | A | B | R¹ | R⁶ | Melting point [° C.] |
|---|---|---|---|---|---|
| 87 | 1-CH₃-3-CF₃-pyrazol-5-yl | Cl—(CH₂)₃—NH—CO | " | " | |
| 88 | 1-CH₃-3-CF₃-pyrazol-5-yl | cyclohexyl-NH—CO | " | " | |
| 89 | 1-CH₃-3-CF₃-pyrazol-5-yl | C₂H₅—O—CO—CH₂—NH—CO | " | " | |
| 90 | 1-CH₃-3-CF₃-pyrazol-5-yl | benzyl-NH—CO | " | " | |
| 91 | 1-CH₃-3-CF₃-pyrazol-5-yl | C₂H₅—O—CO—(CH₂)₂—NH—CO | " | " | |
| 92 | 1-CH₃-3-CF₃-pyrazol-5-yl | 4-methylbenzyl-NH—CO | " | " | |
| 93 | 1-CH₃-3-CF₃-pyrazol-5-yl | [(CF₃)₂Cl]C—NH—CO | " | " | |
| 94 | 1-CH₃-3-CF₃-pyrazol-5-yl | CF₃—(CF₂)₅—NH—CO | " | " | |
| 95 | 1-CH₃-3-CF₃-pyrazol-5-yl | phenyl-N(CH₃)—CO | " | " | |
| 96 | 1-CH₃-3-CF₃-pyrazol-5-yl | [(CH₃)₂CH—CH₂]₂N—CO | " | " | |
| 97 | 1-CH₃-3-CF₃-pyrazol-5-yl | [(CH₃)₂CH]₂N—CO | " | " | |
| 98 | 1-CH₃-3-CF₃-pyrazol-5-yl | N-pyrrolidinyl-CO | " | " | |
| 99 | 1-CH₃-3-CF₃-pyrazol-5-yl | N-morpholinyl-CO | " | " | |
| 100 | 1-CH₃-3-CF₃-pyrazol-5-yl | cyclopropyl-SO₂ | " | " | |
| 101 | 1-CH₃-3-CF₃-pyrazol-5-yl | H₂C=CH—SO₂ | " | " | |
| 102 | 1-CH₃-3-CF₃-pyrazol-5-yl | CF₃—CH₂—SO₂ | " | " | |
| 103 | 1-CH₃-3-CF₃-pyrazol-5-yl | (CH₃)₂CH—SO₂ | " | " | |
| 104 | 1-CH₃-3-CF₃-pyrazol-5-yl | C₂H₅—SO₂ | " | " | |
| 105 | 1-CH₃-3-CF₃-pyrazol-5-yl | CF₃—SO₂ | " | " | |
| 106 | 1-CH₃-3-CF₃-pyrazol-5-yl | CH₃—SO₂ | " | " | oil |
| 107 | 1-CH₃-3-CF₃-pyrazol-5-yl | CF₃—SO₂ | " | CF₃—SO₂ | oil |
| 108 | 1-CH₃-3-CF₃-pyrazol-5-yl | (CH₃)₂N—SO₂ | " | H | oil |
| 109 | 1-CH₃-3-CF₃-pyrazol-5-yl | Cl₃C—SO₂ | " | " | |
| 110 | 1-CH₃-3-CF₃-pyrazol-5-yl | CH₃—NH—SO₂ | " | " | |
| 111 | 1-CH₃-3-CF₃-pyrazol-5-yl | 2,4,5-trichlorophenyl-SO₂ | " | " | |
| 112 | 1-CH₃-3-CF₃-pyrazol-5-yl | 4-iodophenyl-SO₂ | " | " | |
| 113 | 1-CH₃-3-CF₃-pyrazol-5-yl | benzyl-SO₂ | " | " | |
| 114 | 1-CH₃-3-CF₃-pyrazol-5-yl | 4-nitrophenyl-SO₂ | " | " | |
| 115 | 1-CH₃-3-CF₃-pyrazol-5-yl | 2-CF₃-phenyl-SO₂ | " | " | |
| 116 | 1-CH₃-3-CF₃-pyrazol-5-yl | 4-tert-butyl-phenyl-SO₂ | " | " | |
| 117 | 1-CH₃-3-CF₃-pyrazol-5-yl | Cl₂CH—SO₂ | " | " | |
| 118 | 1-CH₃-3-CF₃-pyrazol-5-yl | C₃H₇—SO₂ | " | " | |
| 119 | 1-CH₃-3-CF₃-pyrazol-5-yl | 4-chlorophenyl-SO₂ | " | " | |

TABLE 1-continued $$\text{A}-\text{O}-\underset{\underset{\text{N}}{\|}}{\overset{R^1}{\diagdown}}-\text{CH}_2-\underset{\underset{R^6}{|}}{\text{N}}-\text{B}$$ (I'')

| Example | A | B | R¹ | R⁶ | Melting point [° C.] |
|---|---|---|---|---|---|
| 120 | 1-CH₃-3-CF₃-pyrazol-5-yl | 3-nitrophenyl-SO₂ | " | " | |
| 121 | 1-CH₃-3-CF₃-pyrazol-5-yl | phenyl-SO₂ | " | " | |
| 122 | 1-CH₃-3-CF₃-pyrazol-5-yl | CH₃—(CH₂)₃—NH—CS | " | " | |
| 123 | 1-CH₃-3-CF₃-pyrazol-5-yl | C₂H₅—NH—CS | " | " | |
| 124 | 1-CH₃-3-CF₃-pyrazol-5-yl | Phenyl-CH₂—CH₂—NH—CS | " | " | |
| 125 | 1-CH₃-3-CF₃-pyrazol-5-yl | tert-butyl-NH—CS | " | " | |
| 126 | 1-CH₃-3-CF₃-pyrazol-5-yl | 2-CF₃-phenyl-NH—CS | " | " | |
| 127 | 1-CH₃-3-CF₃-pyrazol-5-yl | 4-CF₃-phenyl-NH—CS | " | " | |
| 128 | 1-CH₃-3-CF₃-pyrazol-5-yl | phenyl-NH—CS | " | " | |
| 129 | 1-CH₃-3-CF₃-pyrazol-5-yl | cyclohexyl-NH—CS | " | " | oil |
| 130 | 1-CH₃-3-CF₃-pyrazol-5-yl | (CH₃)₂CH—NH—CS | " | " | |
| 131 | 1-CH₃-3-CF₃-pyrazol-5-yl | CH₃—(CH₂)₇—NH—CS | " | " | |
| 132 | 1-CH₃-3-CF₃-pyrazol-5-yl | CH₃—O—CH₂—CH₂—NH—CS | " | " | |
| 133 | 1-CH₃-3-CF₃-pyrazol-5-yl | benzyl-NH—CS | " | " | |
| 133a | 1-CH₃-3-CF₃-pyrazol-5-yl | 4-Cl-phenyl-O—CS | H | H | oil |
| 133b | 1-CH₃-3-CF₃-pyrazol-5-yl | CH₃CH₂—O—CS | " | " | oil |
| 133c | 1-CH₃-3-CF₃-pyrazol-5-yl | (CH₃)₂CH—O—CS | " | " | oil |
| 133d | 1-CH₃-3-CF₃-pyrazol-5-yl | Cl—CH₂—CH₂—O—CO | " | " | oil |
| 134 | 1-CH₃-3-CF₃-pyrazol-5-yl | CH₃—CHCl—CO | H | CH₃ | oil |
| 135 | 1-CH₃-3-CF₃-pyrazol-5-yl | structure 1 | " | " | oil |
| 136 | 1-CH₃-3-CF₃-pyrazol-5-yl | 3-NO₂-4-Cl-benzoyl | " | " | 131 |
| 137 | 1-CH₃-3-CF₃-pyrazol-5-yl | 4-tert-butylbenzoyl | " | " | oil |
| 138 | 1-CH₃-3-CF₃-pyrazol-5-yl | 2,4,6-trifluorobenzoyl | " | " | oil |
| 139 | 1-CH₃-3-CF₃-pyrazol-5-yl | 3,4-difluorobenzoyl | " | " | |
| 140 | 1-CH₃-3-CF₃-pyrazol-5-yl | 3-trifluoromethylbenzoyl | " | " | |
| 141 | 1-CH₃-3-CF₃-pyrazol-5-yl | 3,4-dichlorobenzoyl | " | " | 103.3 |
| 142 | 1-CH₃-3-CF₃-pyrazol-5-yl | C₂H₅—O—CO—(CH₂)₃—CO | " | " | oil |
| 143 | 1-CH₃-3-CF₃-pyrazol-5-yl | CH₃—(CH₂)₇—CO | " | " | oil |
| 144 | 1-CH₃-3-CF₃-pyrazol-5-yl | phenyl-CH=CH—CO | " | " | wax |
| 145 | 1-CH₃-3-CF₃-pyrazol-5-yl | Cl—(CH₂)₄—CO | " | " | Oil |
| 146 | 1-CH₃-3-CF₃-pyrazol-5-yl | Cl—(CH₂)₃—CO | " | " | Oil |
| 147 | 1-CH₃-3-CF₃-pyrazol-5-yl | CH₃—CH=CH—CO | " | " | Oil |
| 148 | 1-CH₃-3-CF₃-pyrazol-5-yl | CH₃—CH₂—CO | " | " | 64 |

TABLE 1-continued (I")

| Example | A | B | R¹ | R⁶ | Melting point [° C.] |
|---|---|---|---|---|---|
| 149 | 1-CH₃-3-CF₃-pyrazol-5-yl | (CH₃)₂C=CH—CO | " | " | Oil |
| 150 | 1-CH₃-3-CF₃-pyrazol-5-yl | CH₂=CH—CO | " | " | Oil |
| 151 | 1-CH₃-3-CF₃-pyrazol-5-yl | H—CO | " | " | Oil |
| 152 | 1-CH₃-3-CF₃-pyrazol-5-yl | ClH₂C—CO | " | " | 84.3 |
| 153 | 1-CH₃-3-CF₃-pyrazol-5-yl | CH₃—CO | " | " | Oil |
| 154 | 1-CH₃-3-CF₃-pyrazol-5-yl | CH₃—O—CH₂—CO | " | " | 69.1 |
| 155 | 1-CH₃-3-CF₃-pyrazol-5-yl | (CH₃)₂CF—CO | " | " | Oil |
| 156 | 1-CH₃-3-CF₃-pyrazol-5-yl | Cl₂HC—CO | " | " | 67.7 |
| 157 | 1-CH₃-3-CF₃-pyrazol-5-yl | CH₃—CHF—CO | " | " |  |
| 158 | 1-CH₃-3-CF₃-pyrazol-5-yl | CF₃—CO | " | " | Oil |
| 159 | 1-CH₃-3-CF₃-pyrazol-5-yl | cyclopropyl-CO | " | " | 58.9 |
| 160 | 1-CH₃-3-CF₃-pyrazol-5-yl | cyclobutyl-CO | " | " | 67.1 |
| 161 | 1-CH₃-3-CF₃-pyrazol-5-yl | 2-furan-CO | " | " | 80 |
| 162 | 1-CH₃-3-CF₃-pyrazol-5-yl | 2-thienyl-CO | " | " | 99.6 |
| 163 | 1-CH₃-3-CF₃-pyrazol-5-yl | CF₃—CH₂—CO | " | " |  |
| 164 | 1-CH₃-3-CF₃-pyrazol-5-yl | (CF₃)₂CH—CO | " | " |  |
| 165 | 1-CH₃-3-CF₃-pyrazol-5-yl | tert-butyl-CO | " | " |  |
| 166 | 1-CH₃-3-CF₃-pyrazol-5-yl | 3-cyanobenzoyl | " | " |  |
| 167 | 1-CH₃-3-CF₃-pyrazol-5-yl | (CH₃)₂CH—CH₂—CO | " | " |  |
| 168 | 1-CH₃-3-CF₃-pyrazol-5-yl | tert-butyl-CH₂—CO | " | " |  |
| 169 | 1-CH₃-3-CF₃-pyrazol-5-yl | (C₂H₅)₂CH—CO | " | " |  |
| 170 | 1-CH₃-3-CF₃-pyrazol-5-yl | CH₃—CO—O—CH₂—CO | " | " |  |
| 171 | 1-CH₃-3-CF₃-pyrazol-5-yl | CH₃—O—CO—CH₂—CO | " | " |  |
| 172 | 1-CH₃-3-CF₃-pyrazol-5-yl | benzyl-CO | " | " |  |
| 173 | 1-CH₃-3-CF₃-pyrazol-5-yl | CL—CH₂—(CH₃)₂C—CO | " | " |  |
| 174 | 1-CH₃-3-CF₃-pyrazol-5-yl | 4-fluorobenzoyl | " | " |  |
| 175 | 1-CH₃-3-CF₃-pyrazol-5-yl | 2-methoxybenzoyl | " | " |  |
| 176 | 1-CH₃-3-CF₃-pyrazol-5-yl | 4-methoxybenzoyl | " | " |  |
| 177 | 1-CH₃-3-CF₃-pyrazol-5-yl | 4-fluorobenzyl-CO | " | " |  |
| 178 | 1-CH₃-3-CF₃-pyrazol-5-yl | 6-Cl-pyridine-3-CO | " | " |  |
| 179 | 1-CH₃-3-CF₃-pyrazol-5-yl | pyridine-4-CO | " | " |  |
| 180 | 1-CH₃-3-CF₃-pyrazol-5-yl | CH₃—O—CO—(CH₂)₄—CO | " | " |  |
| 181 | 1-CH₃-3-CF₃-pyrazol-5-yl | 2,4,6-trimethoxybenzoyl | " | " |  |

TABLE 1-continued (I")

| Example | A | B | R¹ | R⁶ | Melting point [° C.] |
|---|---|---|---|---|---|
| 182 | 1-CH₃-3-CF₃-pyrazol-5-yl | 4-nitrobenzoyl | " | " | |
| 183 | 1-CH₃-3-CF₃-pyrazol-5-yl | 2,2-dichlorocyclopropyl-CO | " | " | |
| 184 | 1-CH₃-3-CF₃-pyrazol-5-yl | 2,2-difluorocyclopropyl-CO | " | " | |
| 185 | 1-CH₃-3-CF₃-pyrazol-5-yl | 2-methylcyclopropyl-CO | " | " | |
| 186 | 1-CH₃-3-CF₃-pyrazol-5-yl | 1-methylcyclopropyl-CO | " | " | |
| 187 | 1-CH₃-3-CF₃-pyrazol-5-yl | 3-(CF₃—O)-benzoyl | " | " | |
| 188 | 1-CH₃-3-CF₃-pyrazol-5-yl | 2,5-DiCF₃-benzoyl | " | " | |
| 189 | 1-CH₃-3-CF₃-pyrazol-5-yl | 2-Br-5-methoxybenzoyl | " | " | |
| 190 | 1-CH₃-3-CF₃-pyrazol-5-yl | 1-CH₃-2,2-dichlorocyclopropyl-CO | " | " | |
| 191 | 1-CH₃-3-CF₃-pyrazol-5-yl | 2,2,3,3-tetramethyl-cyclo-proypl-CO | " | " | |
| 192 | 1-CH₃-3-CF₃-pyrazol-5-yl | 2,3,4,5,6-pentafluorobenzoyl | " | " | |
| 193 | 1-CH₃-3-CF₃-pyrazol-5-yl | structure 2 | " | " | |
| 194 | 1-CH₃-3-CF₃-pyrazol-5-yl | C₂H₅—O—CO—CO | " | " | oil |
| 195 | 1-CH₃-3-CF₃-pyrazol-5-yl | CH₃—O—CO | " | " | |
| 196 | 1-CH₃-3-CF₃-pyrazol-5-yl | CH₃—CH₂—O—CO | " | " | |
| 197 | 1-CH₃-3-CF₃-pyrazol-5-yl | benzyl-O—CO | " | " | |
| 198 | 1-CH₃-3-CF₃-pyrazol-5-yl | C₄H₉—O—CO | " | " | |
| 199 | 1-CH₃-3-CF₃-pyrazol-5-yl | (CH₃)₂CH—CH₂—O—CO | " | " | |
| 200 | 1-CH₃-3-CF₃-pyrazol-5-yl | (CH₃)₂CH—O—CO | " | " | |
| 201 | 1-CH₃-3-CF₃-pyrazol-5-yl | (CH₃)₃C—O—CO | " | " | |
| 202 | 1-CH₃-3-CF₃-pyrazol-5-yl | C₃H₇—O—CO | " | " | |
| 203 | 1-CH₃-3-CF₃-pyrazol-5-yl | 4-NO₂-benzyl-O—CO | " | " | |
| 204 | 1-CH₃-3-CF₃-pyrazol-5-yl | CH₂=CH—CH₂—O—CO | " | " | |
| 205 | 1-CH₃-3-CF₃-pyrazol-5-yl | cyclopentyl-O—CO | " | " | |
| 206 | 1-CH₃-3-CF₃-pyrazol-5-yl | CF₃—CH₂—O—CO | " | " | |
| 207 | 1-CH₃-3-CF₃-pyrazol-5-yl | (CH₃)₂N—CO | " | " | |
| 208 | 1-CH₃-3-CF₃-pyrazol-5-yl | C₂H₅—NH—CO | " | " | |
| 209 | 1-CH₃-3-CF₃-pyrazol-5-yl | 2,4-difluorophenyl-NH—CO | " | " | |
| 210 | 1-CH₃-3-CF₃-pyrazol-5-yl | 3-fluorophenyl-NH—CO | " | " | |
| 211 | 1-CH₃-3-CF₃-pyrazol-5-yl | H₃C—NH—CO | " | " | |
| 212 | 1-CH₃-3-CF₃-pyrazol-5-yl | CH₂=CH—CH₂—NH—CO | " | " | |
| 213 | 1-CH₃-3-CF₃-pyrazol-5-yl | (CH₃)₂CH—NH—CO | " | " | |
| 214 | 1-CH₃-3-CF₃-pyrazol-5-yl | (CH₃)₂C—NH—CO | " | " | |

TABLE 1-continued

Structure (I"): A-O-[pyridine with R¹ at 4-position, N in ring]-CH₂-N(R⁶)-B

| Example | A | B | R¹ | R⁶ | Melting point [° C.] |
|---|---|---|---|---|---|
| 215 | 1-CH₃-3-CF₃-pyrazol-5-yl | (CH₃)₂CH—CH₂—NH—CO | " | " | |
| 216 | 1-CH₃-3-CF₃-pyrazol-5-yl | Cl—(CH2)3-NH—CO | " | " | |
| 217 | 1-CH₃-3-CF₃-pyrazol-5-yl | cyclohexyl-NH—CO | " | " | |
| 218 | 1-CH₃-3-CF₃-pyrazol-5-yl | C₂H₅—O—CO—CH₂—NH—CO | " | " | |
| 219 | 1-CH₃-3-CF₃-pyrazol-5-yl | benzyl-NH—CO | " | " | |
| 220 | 1-CH₃-3-CF₃-pyrazol-5-yl | C₂H₅—O—CO—(CH₂)₂—NH—CO | " | " | |
| 221 | 1-CH₃-3-CF₃-pyrazol-5-yl | 4-methylbenzyl-NH—CO | " | " | |
| 222 | 1-CH₃-3-CF₃-pyrazol-5-yl | [(CF₃)₂Cl]C—NH—CO | " | " | |
| 223 | 1-CH₃-3-CF₃-pyrazol-5-yl | CF₃—(CF₂)₅—NH—CO | " | " | |
| 224 | 1-CH₃-3-CF₃-pyrazol-5-yl | phenyl-N(CH₃)—CO | " | " | |
| 225 | 1-CH₃-3-CF₃-pyrazol-5-yl | [(CH₃)₂CH—CH₂]₂N—CO | " | " | |
| 226 | 1-CH₃-3-CF₃-pyrazol-5-yl | [(CH₃)₂CH₂]₂N—CO | " | " | |
| 227 | 1-CH₃-3-CF₃-pyrazol-5-yl | N-pyrrolidinyl-CO | " | " | |
| 228 | 1-CH₃-3-CF₃-pyrazol-5-yl | N-morpholinyl-CO | " | " | |
| 229 | 1-CH₃-3-CF₃-pyrazol-5-yl | cyclopropyl-SO₂ | " | " | |
| 230 | 1-CH₃-3-CF₃-pyrazol-5-yl | H₂C=CH—SO₂ | " | " | |
| 231 | 1-CH₃-3-CF₃-pyrazol-5-yl | CF₃—CH₂—SO₂ | " | " | |
| 232 | 1-CH₃-3-CF₃-pyrazol-5-yl | (CH₃)₂CH—SO₂ | " | " | |
| 233 | 1-CH₃-3-CF₃-pyrazol-5-yl | C₂H₅—SO₂ | " | " | |
| 234 | 1-CH₃-3-CF₃-pyrazol-5-yl | CF₃—SO₂ | " | " | |
| 235 | 1-CH₃-3-CF₃-pyrazol-5-yl | (CH₃)₂N—SO₂ | " | " | |
| 236 | 1-CH₃-3-CF₃-pyrazol-5-yl | Cl₃C—SO₂ | " | " | |
| 237 | 1-CH₃-3-CF₃-pyrazol-5-yl | CH₃—NH—SO₂ | " | " | |
| 238 | 1-CH₃-3-CF₃-pyrazol-5-yl | 2,4,5-trichlorophenyl-SO₂ | " | " | |
| 239 | 1-CH₃-3-CF₃-pyrazol-5-yl | 4-iodophenyl-SO₂ | " | " | |
| 240 | 1-CH₃-3-CF₃-pyrazol-5-yl | benzyl-SO₂ | " | " | |
| 241 | 1-CH₃-3-CF₃-pyrazol-5-yl | 4-bitrophenyl-SO₂ | " | " | |
| 242 | 1-CH₃-3-CF₃-pyrazol-5-yl | 2-CF₃-phenyl-SO₂ | " | " | |
| 243 | 1-CH₃-3-CF₃-pyrazol-5-yl | 4-tert-butyl-phenyl-SO₂ | " | " | |
| 244 | 1-CH₃-3-CF₃-pyrazol-5-yl | Cl₂CH—SO₂ | " | " | |
| 245 | 1-CH₃-3-CF₃-pyrazol-5-yl | C₃H₇—SO₂ | " | " | |
| 246 | 1-CH₃-3-CF₃-pyrazol-5-yl | 4-chlorophenyl-SO₂ | " | " | |
| 247 | 1-CH₃-3-CF₃-pyrazol-5-yl | 3-nitrophenyl-SO₂ | " | " | |

TABLE 1-continued $$\text{(I'')}$$

Structure: A-O-[pyridine with R¹ at 4-position, N in ring]-CH₂-N(R⁶)-B

| Example | A | B | R¹ | R⁶ | Melting point [° C.] |
|---|---|---|---|---|---|
| 248 | 1-CH₃-3-CF₃-pyrazol-5-yl | phenyl-SO₂ | " | " | |
| 249 | 1-CH₃-3-CF₃-pyrazol-5-yl | CH₃—(CH₂)₃—NH—CS | " | " | |
| 250 | 1-CH₃-3-CF₃-pyrazol-5-yl | C₂H₅—NH—CS | " | " | |
| 251 | 1-CH₃-3-CF₃-pyrazol-5-yl | Phenyl-CH₂—CH₂—NH—CS | " | " | |
| 252 | 1-CH₃-3-CF₃-pyrazol-5-yl | tert-butyl-NH—CS | " | " | |
| 253 | 1-CH₃-3-CF₃-pyrazol-5-yl | 2-CF₃-phenyl-NH—CS | " | " | |
| 254 | 1-CH₃-3-CF₃-pyrazol-5-yl | 4-CF₃-phenyl-NH—CS | " | " | |
| 255 | 1-CH₃-3-CF₃-pyrazol-5-yl | phenyl-NH—CS | " | " | |
| 256 | 1-CH₃-3-CF₃-pyrazol-5-yl | cyclohexyl-NH—CS | " | " | |
| 257 | 1-CH₃-3-CF₃-pyrazol-5-yl | (CH₃)₂CH—NH—CS | " | " | |
| 258 | 1-CH₃-3-CF₃-pyrazol-5-yl | CH₃—(CH₂)₇—NH—CS | " | " | |
| 259 | 1-CH₃-3-CF₃-pyrazol-5-yl | CH₃—O—CH₂—CH₂—NH—CS | " | " | |
| 260 | 1-CH₃-3-CF₃-pyrazol-5-yl | benzyl-NH—CS | " | " | |
| 261 | 3-CF₃-phenyl | CH₃—CHCl—CO | H | H | |
| 262 | 1-CH₃-3-CF₃-pyrazol-5-yl | structure 1 | " | " | |
| 263 | 1-CH₃-3-CF₃-pyrazol-5-yl | 3-NO₂-4-Cl-benzoyl | " | " | 98.8 |
| 264 | 1-CH₃-3-CF₃-pyrazol-5-yl | 4-tert-butylbenzoyl | " | " | |
| 265 | 1-CH₃-3-CF₃-pyrazol-5-yl | 2,4,6-trifluorobenzoyl | " | " | 105 |
| 266 | 1-CH₃-3-CF₃-pyrazol-5-yl | 3,4-difluorobenzoyl | " | " | |
| 267 | 1-CH₃-3-CF₃-pyrazol-5-yl | 3-trifluoromethylbenzoyl | " | " | |
| 268 | 1-CH₃-3-CF₃-pyrazol-5-yl | 3,4-dichlorobenzoyl | " | " | |
| 269 | 1-CH₃-3-CF₃-pyrazol-5-yl | C₂H₅—O—CO—(CH₂)₃—CO | " | " | oil |
| 270 | 1-CH₃-3-CF₃-pyrazol-5-yl | CH₃—(CH₂)₇—CO | " | " | oil |
| 271 | 1-CH₃-3-CF₃-pyrazol-5-yl | phenyl-CH=CH—CO | " | " | oil |
| 272 | 1-CH₃-3-CF₃-pyrazol-5-yl | Cl—(CH₂)₄—CO | " | " | oil |
| 273 | 1-CH₃-3-CF₃-pyrazol-5-yl | Cl—(CH₂)₃—CO | " | " | oil |
| 274 | 1-CH₃-3-CF₃-pyrazol-5-yl | CH₃—CH=CH—CO | " | " | |
| 275 | 1-CH₃-3-CF₃-pyrazol-5-yl | CH₃—CH₂—CO | " | " | oil |
| 276 | 1-CH₃-3-CF₃-pyrazol-5-yl | (CH₃)₂C=CH—CO | " | " | 71 |
| 277 | 1-CH₃-3-CF₃-pyrazol-5-yl | CH₂=CH—CO | " | " | |
| 278 | 1-CH₃-3-CF₃-pyrazol-5-yl | H—CO | " | " | |
| 279 | 1-CH₃-3-CF₃-pyrazol-5-yl | ClH₂C—CO | " | " | 57 |
| 280 | 1-CH₃-3-CF₃-pyrazol-5-yl | CH₃—CO | " | " | |

TABLE 1-continued $$\text{structure (I'')}$$

| Example | A | B | R¹ | R⁶ | Melting point [° C.] |
|---|---|---|---|---|---|
| 281 | 1-CH₃-3-CF₃-pyrazol-5-yl | (CH₃)₂CH—CO | " | " | 71 |
| 282 | 1-CH₃-3-CF₃-pyrazol-5-yl | CH₃—O—CH₂—CO | " | " | oil |
| 283 | 1-CH₃-3-CF₃-pyrazol-5-yl | (CH₃)₂CF—CO | " | " | 51 |
| 284 | 1-CH₃-3-CF₃-pyrazol-5-yl | CH₃—CHF—CO | " | " | |
| 285 | 1-CH₃-3-CF₃-pyrazol-5-yl | CF₃—CO | " | " | 55 |
| 286 | 1-CH₃-3-CF₃-pyrazol-5-yl | cyclopropyl-CO | " | " | 98 |
| 287 | 1-CH₃-3-CF₃-pyrazol-5-yl | cyclobutyl-CO | " | " | 78 |
| 288 | 1-CH₃-3-CF₃-pyrazol-5-yl | 2-furan-CO | " | " | |
| 289 | p41 5-yl | 2-thienyl-CO | " | " | |
| 290 | 1-CH₃-3-CF₃-pyrazol-5-yl | CF₃—CH₂—CO | " | " | |
| 291 | 1-CH₃-3-CF₃-pyrazol-5-yl | (CF₃)₂CH—CO | " | " | |
| 292 | 1-CH₃-3-CF₃-pyrazol-5-yl | tert-butyl-CO | " | " | |
| 293 | 1-CH₃-3-CF₃-pyrazol-5-yl | 3-cyanobenzoyl | " | " | |
| 294 | 1-CH₃-3-CF₃-pyrazol-5-yl | (CH₃)₂CH—CH₂—CO | " | " | |
| 295 | 1-CH₃-3-CF₃-pyrazol-5-yl | tert-butyl-CH₂—CO | " | " | |
| 296 | 1-CH₃-3-CF₃-pyrazol-5-yl | (C₂H₅)₂CH—CO | " | " | |
| 297 | 1-CH₃-3-CF₃-pyrazol-5-yl | CH₃—CO—O—CH₂—CO | " | " | |
| 298 | 1-CH₃-3-CF₃-pyrazol-5-yl | CH₃—O—CO—CH₂—CO | " | " | |
| 299 | 1-CH₃-3-CF₃-pyrazol-5-yl | benzyl-CO | " | '1 | |
| 300 | 1-CH₃-3-CF₃-pyrazol-5-yl | CL—CH₂—(CH₃)₂C—CO | " | " | |
| 301 | 1-CH₃-3-CF₃-pyrazol-5-yl | 4-fluorobenzoyl | " | " | |
| 302 | 1-CH₃-3-CF₃-pyrazol-5-yl | 2-methoxybenzoyl | " | " | |
| 303 | 1-CH₃-3-CF₃-pyrazol-5-yl | 4-methoxybenzoyl | " | " | |
| 304 | 1-CH₃-3-CF₃-pyrazol-5-yl | 4-fluorobenzyl-CO | " | " | |
| 305 | 1-CH₃-3-CF₃-pyrazol-5-yl | 6-Cl-pyridine-3-CO | " | " | |
| 306 | 1-CH₃-3-CF₃-pyrazol-5-yl | pyridine-4-CO | " | " | |
| 307 | 1-CH₃-3-CF₃-pyrazol-5-yl | CH₃—O—CO—(CH₂)₄—CO | " | " | |
| 308 | 1-CH₃-3-CF₃-pyrazol-5-yl | 2,4,6-trimethylbenzoyl | " | " | |
| 309 | 1-CH₃-3-CF₃-pyrazol-5-yl | 4-nitrobenzoyl | " | " | |
| 310 | 1-CH₃-3-CF₃-pyrazol-5-yl | 2,2-dichlorocyclopropyl-CO | " | " | |
| 311 | 1-CH₃-3-CF₃-pyrazol-5-yl | 2,2-difluorocyclopropyl-CO | " | " | |
| 312 | 1-CH₃-3-CF₃-pyrazol-5-yl | 2-methylcyclopropyl-CO | " | " | |
| 313 | 1-CH₃-3-CF₃-pyrazol-5-yl | 1-methylcyclopropyl-CO | " | " | |

TABLE 1-continued (I")

| Example | A | B | R¹ | R⁶ | Melting point [° C.] |
|---|---|---|---|---|---|
| 314 | 1-CH₃-3-CF₃-pyrazol-5-yl | 3-(CF₃—O)-benzoyl | " | " | |
| 315 | 1-CH₃-3-CF₃-pyrazol-5-yl | 2,5-DiCF₃-benzoyl | " | " | |
| 316 | 1-CH₃-3-CF₃-pyrazol-5-yl | 2-Br-5-methoxybenzoyl | " | " | |
| 317 | 1-CH₃-3-CF₃-pyrazol-5-yl | 1-CH₃-2,2-dichlorocyclopropyl-CO | " | " | |
| 318 | 1-CH₃-3-CF₃-pyrazol-5-yl | 2,2,3,3-tetramethyl-cyclopropyl-CO | " | " | |
| 319 | 1-CH₃-3-CF₃-pyrazol-5-yl | 2,3,4,5,6-pentafluorobenzoyl | " | " | |
| 320 | 1-CH₃-3-CF₃-pyrazol-5-yl | structure 2 | " | " | |
| 321 | 1-CH₃-3-CF₃-pyrazol-5-yl | C₂H₅—O—CO—CO | " | " | 57 |
| 322 | 1-CH₃-3-CF₃-pyrazol-5-yl | CH₃—O—CO | " | " | |
| 323 | 1-CH₃-3-CF₃-pyrazol-5-yl | CH₃—CH₂—O—CO | " | " | |
| 324 | 1-CH₃-3-CF₃-pyrazol-5-yl | benzyl-O—CO | " | " | |
| 325 | 1-CH₃-3-CF₃-pyrazol-5-yl | C₄H₉—O—CO | " | " | |
| 326 | 1-CH₃-3-CF₃-pyrazol-5-yl | (CH₃)₂CH—CH₂—O—CO | " | " | |
| 327 | 1-CH₃-3-CF₃-pyrazol-5-yl | (CH₃)₂CH—O—CO | " | " | |
| 328 | 1-CH₃-3-CF₃-pyrazol-5-yl | (CH₃)₃C—O—CO | " | " | |
| 329 | 1-CH₃-3-CF₃-pyrazol-5-yl | C₃H₇—O—CO | " | " | |
| 330 | 1-CH₃-3-CF₃-pyrazol-5-yl | 4-NO₂-benzyl-O—CO | " | " | |
| 331 | 1-CH₃-3-CF₃-pyrazol-5-yl | CH₂=CH—CH₂—O—CO | " | " | |
| 332 | 1-CH₃-3-CF₃-pyrazol-5-yl | cyclopentyl-O—CO | " | " | |
| 333 | 1-CH₃-3-CF₃-pyrazol-5-yl | CF₃—CH₂—O—CO | " | " | |
| 334 | 1-CH₃-3-CF₃-pyrazol-5-yl | (CH₃)₂N—CO | " | " | |
| 335 | 1-CH₃-3-CF₃-pyrazol-5-yl | C₂H₅—NH—CO | " | " | |
| 336 | 1-CH₃-3-CF₃-pyrazol-5-yl | 2,4-difluorophenyl-NH—CO | " | " | |
| 337 | 1-CH₃-3-CF₃-pyrazol-5-yl | 3-fluorophenly-NH—CO | " | " | |
| 338 | 1-CH₃-3-CF₃-pyrazol-5-yl | H₃C—NH—CO | " | " | |
| 339 | 1-CH₃-3-CF₃-pyrazol-5-yl | CH₂=CH—CH₂—NH—CO | " | " | |
| 340 | 1-CH₃-3-CF₃-pyrazol-5-yl | (CH₃)₂CH—NH—CO | " | " | |
| 341 | 1-CH₃-3-CF₃-pyrazol-5-yl | (CH₃)₃C—NH—CO | " | " | |
| 342 | 1-CH₃-3-CF₃-pyrazol-5-yl | (CH₃)₂CH—CH₂—NH—CO | " | " | |
| 343 | 1-CH₃-3-CF₃-pyrazol-5-yl | Cl—(CH₂)₃—NH—CO | " | " | |
| 344 | 1-CH₃-3-CF₃-pyrazol-5-yl | cyclohexyl-NH—CO | " | " | |
| 345 | 1-CH₃-3-CF₃-pyrazol-5-yl | C₂H₅—O—CO—CH₂—NH—CO | " | " | |
| 346 | 1-CH₃-3-CF₃-pyrazol-5-yl | benzyl-NH—CO | " | " | |

TABLE 1-continued

Structure (I''): A-O-[pyridine with R¹ at 4-position, N at 1-position]-CH₂-N(R⁶)-B

| Example | A | B | R¹ | R⁶ | Melting point [° C.] |
|---------|---|---|----|----|----------------------|
| 347 | 1-CH₃-3-CF₃-pyrazol-5-yl | C₂H₅—O—CO—(CH₂)₂—NH—CO | " | " | |
| 348 | 1-CH₃-3-CF₃-pyrazol-5-yl | 4-methylbenzyl-NH—CO | " | " | |
| 349 | 1-CH₃-3-CF₃-pyrazol-5-yl | [(CF₃)₂Cl]C—NH—CO | " | " | |
| 350 | 1-CH₃-3-CF₃-pyrazol-5-yl | CF₃—(CF₂)₅—NH—CO | " | " | |
| 351 | 1-CH₃-3-CF₃-pyrazol-5-yl | phenyl-N(CH₃)—CO | " | " | |
| 352 | 1-CH₃-3-CF₃-pyrazol-5-yl | [(CH₃)₂CH—CH₂]₂N—CO | " | " | |
| 353 | 1-CH₃-3-CF₃-pyrazol-5-yl | [(CH₃)₂CH]₂N—CO | " | " | |
| 354 | 1-CH₃-3-CF₃-pyrazol-5-yl | N-pyrrolidinyl-CO | " | " | |
| 355 | 1-CH₃-3-CF₃-pyrazol-5-yl | N-morpholinyl-CO | " | " | |
| 356 | 1-CH₃-3-CF₃-pyrazol-5-yl | cyclopropyl-SO₂ | " | " | |
| 357 | 1-CH₃-3-CF₃-pyrazol-5-yl | H₂C=CH—SO₂ | " | " | |
| 358 | 1-CH₃-3-CF₃-pyrazol-5-yl | CF₃—CH₂—SO₂ | " | " | |
| 359 | 1-CH₃-3-CF₃-pyrazol-5-yl | (CH₃)₂CH—SO₂ | " | " | |
| 360 | 1-CH₃-3-CF₃-pyrazol-5-yl | C₂H₅—SO₂ | " | " | |
| 361 | 1-CH₃-3-CF₃-pyrazol-5-yl | CF₃—SO₂ | " | " | |
| 362 | 1-CH₃-3-CF₃-pyrazol-5-yl | CH₃—SO₂ | " | " | |
| 363 | 1-CH₃-3-CF₃-pyrazol-5-yl | CF₃—SO₂ | " | CF₃—SO₂ | |
| 364 | 1-CH₃-3-CF₃-pyrazol-5-yl | (CH₃)₂N—SO₂ | " | H | |
| 365 | 1-CH₃-3-CF₃-pyrazol-5-yl | Cl₃C—SO₂ | " | " | |
| 366 | 1-CH₃-3-CF₃-pyrazol-5-yl | CH₃—NH—SO₂ | " | " | |
| 367 | 1-CH₃-3-CF₃-pyrazol-5-yl | 2,4,5-trichlorophenyl-SO₂ | " | " | |
| 368 | 1-CH₃-3-CF₃-pyrazol-5-yl | 4-iodophenyl-SO₂ | " | " | |
| 369 | 1-CH₃-3-CF₃-pyrazol-5-yl | benzyl-SO₂ | " | " | |
| 370 | 1-CH₃-3-CF₃-pyrazol-5-yl | 4-nitrophenyl-SO₂ | " | " | |
| 371 | 1-CH₃-3-CF₃-pyrazol-5-yl | 2-CF₃-phenyl-SO₂ | " | " | |
| 372 | 1-CH₃-3-CF₃-pyrazol-5-yl | 4-tert-butyl-phenyl-SO₂ | " | " | |
| 373 | 1-CH₃-3-CF₃-pyrazol-5-yl | Cl₂CH—SO₂ | " | " | |
| 374 | 1-CH₃-3-CF₃-pyrazol-5-yl | C₃H₇—SO₂ | " | " | |
| 375 | 1-CH₃-3-CF₃-pyrazol-5-yl | 4-chlorophenyl-SO₂ | " | " | |
| 376 | 1-CH₃-3-CF₃-pyrazol-5-yl | 3-nitrophenyl-SO₂ | " | " | |
| 377 | 1-CH₃-3-CF₃-pyrazol-5-yl | phenyl-SO₂ | " | " | |
| 378 | 1-CH₃-3-CF₃-pyrazol-5-yl | CH₃—(CH₂)₃—NH—CS | " | " | |
| 379 | 1-CH₃-3-CF₃-pyrazol-5-yl | C₂H₅—NH—CS | " | " | |

TABLE 1-continued $$\text{A}-\text{O}-\underset{\underset{\text{N}}{\|}}{\overset{\overset{R^1}{|}}{\bigcirc}}-\text{CH}_2-\underset{\underset{\text{B}}{|}}{\overset{\overset{R^6}{|}}{\text{N}}} \quad (I'')$$

| Example | A | B | R$^1$ | R$^6$ | Melting point [° C.] |
|---|---|---|---|---|---|
| 380 | 1-CH$_3$-3-CF$_3$-pyrazol-5-yl | Phenyl-CH$_2$—CH$_2$—NH—CS | " | " | |
| 381 | 1-CH$_3$-3-CF$_3$-pyrazol-5-yl | tert-butyl-NH—CS | " | " | |
| 382 | 1-CH$_3$-3-CF$_3$-pyrazol-5-yl | 2-CF$_3$-phenyl-NH—CS | " | " | |
| 383 | 1-CH$_3$-3-CF$_3$-pyrazol-5-yl | 4-CF$_3$-phenyl-NH—CS | " | " | |
| 384 | 1-CH$_3$-3-CF$_3$-pyrazol-5-yl | phenyl-NH—CS | " | " | |
| 385 | 1-CH$_3$-3-CF$_3$-pyrazol-5-yl | cyclohexyl-NH—CS | " | " | |
| 386 | 1-CH$_3$-3-CF$_3$-pyrazol-5-yl | (CH$_3$)$_2$CH—NH—CS | " | " | |
| 387 | 1-CH$_3$-3-CF$_3$-pyrazol-5-yl | CH$_3$—(CH$_2$)$_7$—NH—CS | " | " | |
| 388 | 1-CH$_3$-3-CF$_3$-pyrazol-5-yl | CH$_3$—O—CH$_2$—CH$_2$—NH—CS | " | " | |
| 389 | 1-CH$_3$-3-CF$_3$-pyrazol-5-yl | benzyl-NH—CS | " | " | |
| 390 | 3-CF$_3$-phenyl | CH$_3$—CHCl—CO | H | CH$_3$ | |
| 391 | 1-CH$_3$-3-CF$_3$-pyrazol-5-yl | structure 1 | " | " | |
| 392 | 1-CH$_3$-3-CF$_3$-pyrazol-5-yl | 3-NO$_2$-4-Cl-benzoyl | " | " | |
| 393 | 1-CH$_3$-3-CF$_3$-pyrazol-5-yl | 4-tert-butylbenzoyl | " | " | |
| 394 | 1-CH$_3$-3-CF$_3$-pyrazol-5-yl | 2,4,6-trifluorobenzoyl | " | " | |
| 395 | 1-CH$_3$-3-CF$_3$-pyrazol-5-yl | 3,4-difluorobenzoyl | " | " | |
| 396 | 1-CH$_3$-3-CF$_3$-pyrazol-5-yl | 3-trifluoromethylbenzoyl | " | " | |
| 397 | 1-CH$_3$-3-CF$_3$-pyrazol-5-yl | 3,4-dichlorobenzoyl | " | " | |
| 398 | 1-CH$_3$-3-CF$_3$-pyrazol-5-yl | C$_2$H$_5$—O—CO—(CH$_2$)$_3$—CO | " | " | |
| 399 | 1-CH$_3$-3-CF$_3$-pyrazol-5-yl | CH$_3$—(CH$_2$)$_7$—CO | " | " | |
| 400 | 1-CH$_3$-3-CF$_3$-pyrazol-5-yl | phenyl-CH=CH—CO | " | " | |
| 401 | 1-CH$_3$-3-CF$_3$-pyrazol-5-yl | Cl—(CH$_2$)$_4$—CO | " | " | |
| 402 | 1-CH$_3$-3-CF$_3$-pyrazol-5-yl | Cl—(CH$_2$)$_3$—CO | " | " | |
| 403 | 1-CH$_3$-3-CF$_3$-pyrazol-5-yl | CH$_3$—CH=CH—CO | " | " | |
| 404 | 1-CH$_3$-3-CF$_3$-pyrazol-5-yl | CH$_3$—CH$_2$—CO | " | " | |
| 405 | 1-CH$_3$-3-CF$_3$-pyrazol-5-yl | (CH$_3$)$_2$C=CH—CO | " | " | |
| 406 | 1-CH$_3$-3-CF$_3$-pyrazol-5-yl | CH$_2$=CH—CO | " | " | |
| 407 | 1-CH$_3$-3-CF$_3$-pyrazol-5-yl | H—CO | " | " | |
| 408 | 1-CH$_3$-3-CF$_3$-pyrazol-5-yl | ClH$_2$C—CO | " | " | |
| 409 | 1-CH$_3$-3-CF$_3$-pyrazol-5-yl | CH$_3$—CO | " | " | |
| 410 | 1-CH$_3$-3-CF$_3$-pyrazol-5-yl | (CH$_3$)$_2$CH—CO | " | " | |
| 411 | 1-CH$_3$-3-CF$_3$-pyrazol-5-yl | CH$_3$—O—CH$_2$—CO | " | " | |
| 412 | 1-CH$_3$-3-CF$_3$-pyrazol-5-yl | (CH$_3$)$_2$CF—CO | " | " | |

TABLE 1-continued (I'')

| Example | A | B | R$^1$ | R$^6$ | Melting point [° C.] |
|---|---|---|---|---|---|
| 413 | 1-CH$_3$-3-CF$_3$-pyrazol-5-yl | Cl$_2$HC—CO | " | " | |
| 414 | 1-CH$_3$-3-CF$_3$-pyrazol-5-yl | CH$_3$—CHF—CO | " | " | |
| 415 | 1-CH$_3$-3-CF$_3$-pyrazol-5-yl | CF$_3$—CO | " | " | |
| 416 | 1-CH$_3$-3-CF$_3$-pyrazol-5-yl | cyclopropyl-CO | " | " | |
| 417 | 1-CH$_3$-3-CF$_3$-pyrazol-5-yl | cyclobutyl-CO | " | " | |
| 418 | 1-CH$_3$-3-CF$_3$-pyrazol-5-yl | 2-furan-CO | " | " | |
| 419 | 1-CH$_3$-3-CF$_3$-pyrazol-5-yl | 2-thienyl-CO | " | " | |
| 420 | 1-CH$_3$-3-CF$_3$-pyrazol-5-yl | CF$_3$—CH$_2$—CO | " | " | |
| 421 | 1-CH$_3$-3-CF$_3$-pyrazol-5-yl | (CF$_3$)$_2$CH—CO | " | " | |
| 422 | 1-CH$_3$-3-CF$_3$-pyrazol-5-yl | tert-butyl-CO | " | " | |
| 423 | 1-CH$_3$-3-CF$_3$-pyrazol-5-yl | 3-cyanobenzoyl | " | " | |
| 424 | 1-CH$_3$-3-CF$_3$-pyrazol-5-yl | (CH$_3$)$_2$CH—CH$_2$—CO | " | " | |
| 425 | 1-CH$_3$-3-CF$_3$-pyrazol-5-yl | tert-butyl-CH$_2$—CO | " | " | |
| 426 | 1-CH$_3$-3-CF$_3$-pyrazol-5-yl | (C$_2$H$_5$)$_2$CH—CO | " | " | |
| 427 | 1-CH$_3$-3-CF$_3$-pyrazol-5-yl | CH$_3$—CO—O—CH$_2$—CO | " | " | |
| 428 | 1-CH$_3$-3-CF$_3$-pyrazol-5-yl | CH$_3$—O—CO—CH$_2$—CO | " | " | |
| 429 | 1-CH$_3$-3-CF$_3$-pyrazol-5-yl | benzyl-CO | " | " | |
| 430 | 1-CH$_3$-3-CF$_3$-pyrazol-5-yl | CL—CH$_2$—(CH$_3$)$_2$C—CO | " | " | |
| 431 | 1-CH$_3$-3-CF$_3$-pyrazol-5-yl | 4-fluorobenzoyl | " | " | |
| 432 | 1-CH$_3$-3-CF$_3$-pyrazol-5-yl | 2-methoxybenzoyl | " | " | |
| 433 | 1-CH$_3$-3-CF$_3$-pyrazol-5-yl | 4-methoxybenzoyl | " | " | |
| 434 | 1-CH$_3$-3-CF$_3$-pyrazol-5-yl | 4-fluorobenzoyl-CO | " | " | |
| 435 | 1-CH$_3$-3-CF$_3$-pyrazol-5-yl | 6-Cl-pyridine-3-CO | " | " | |
| 436 | 1-CH$_3$-3-CF$_3$-pyrazol-5-yl | pyridine-4-CO | " | " | |
| 437 | 1-CH$_3$-3-CF$_3$-pyrazol-5-yl | CH$_3$—O—CO—(CH$_2$)$_4$—CO | " | " | |
| 438 | 1-CH$_3$-3-CF$_3$-pyrazol-5-yl | 2,4,6-trimethoxybenzoyl | " | " | |
| 439 | 1-CH$_3$-3-CF$_3$-pyrazol-5-yl | 4-nitrobenzoyl | " | " | |
| 440 | 1-CH$_3$-3-CF$_3$-pyrazol-5-yl | 2,2-dichlorocyclopropyl-CO | " | " | |
| 441 | 1-CH$_3$-3-CF$_3$-pyrazol-5-yl | 2,2-difluorocyclopropyl-CO | " | " | |
| 442 | 1-CH$_3$-3-CF$_3$-pyrazol-5-yl | 2-methylcyclopropyl-CO | " | " | |
| 443 | 1-CH$_3$-3-CF$_3$-pyrazol-5-yl | 1-methylcyclopropyl-CO | " | " | |
| 444 | 1-CH$_3$-3-CF$_3$-pyrazol-5-yl | 3-(CF$_3$—O)-benzoyl | " | " | |
| 445 | 1-CH$_3$-3-CF$_3$-pyrazol-5-yl | 2,5-DiCF$_3$-benzoyl | " | " | |

TABLE 1-continued (I")

| Example | A | B | R¹ | R⁶ | Melting point [° C.] |
|---|---|---|---|---|---|
| 446 | 1-CH₃-3-CF₃-pyrazol-5-yl | 2-Br-5-methoxybenzoyl | " | " | |
| 447 | 1-CH₃-3-CF₃-pyrazol-5-yl | 1-CH₃-2,2-dichlorocyclopropyl-CO | " | " | |
| 448 | 1-CH₃-3-CF₃-pyrazol-5-yl | 2,2,3,3-tetramethyl-cyclo-propyl-CO | " | " | |
| 449 | 1-CH₃-3-CF₃-pyrazol-5-yl | 2,3,4,5,6-pentafluorobenzoyl | " | " | |
| 450 | 1-CH₃-3-CF₃-pyrazol-5-yl | structure 2 | " | " | |
| 451 | 1-CH₃-3-CF₃-pyrazol-5-yl | C₂H₅—O—CO—CO | " | " | |
| 452 | 1-CH₃-3-CF₃-pyrazol-5-yl | CH₃—O—CO | " | " | |
| 453 | 1-CH₃-3-CF₃-pyrazol-5-yl | CH₃—CH₂—O—CO | " | " | |
| 454 | " | benzyl-O—CO | " | " | |
| 455 | 1-CH₃-3-CF₃-pyrazol-5-yl | C₄H₉—O—CO | " | " | |
| 456 | 1-CH₃-3-CF₃-pyrazol-5-yl | (CH₃)₂CH—CH₂—O—CO | " | " | |
| 457 | 1-CH₃-3-CF₃-pyrazol-5-yl | (CH₃)₂CH—O—CO | " | " | |
| 458 | 1-CH₃-3-CF₃-pyrazol-5-yl | (CH₃)₃C—O—CO | " | " | |
| 459 | 1-CH₃-3-CF₃-pyrazol-5-yl | C₃H₇—O—CO | " | " | |
| 460 | 1-CH₃-3-CF₃-pyrazol-5-yl | 4-NO₂-benzyl-O—CO | " | " | |
| 461 | 1-CH₃-3-CF₃-pyrazol-5-yl | CH₂=CH—CH₂—O—CO | " | " | |
| 462 | 1-CH₃-3-CF₃-pyrazol-5-yl | cyclopentyl-O—CO | " | " | |
| 463 | 1-CH₃-3-CF₃-pyrazol-5-yl | CF₃—CH₂—O—CO | " | " | |
| 464 | 1-CH₃-3-CF₃-pyrazol-5-yl | (CH₃)₂N—CO | " | " | |
| 465 | 1-CH₃-3-CF₃-pyrazol-5-yl | C₂H₅—NH—CO | " | " | |
| 466 | 1-CH₃-3-CF₃-pyrazol-5-yl | 2,4-difluorophenyl-NH—CO | " | " | |
| 467 | 1-CH₃-3-CF₃-pyrazol-5-yl | 3-fluorophenyl-NH—CO | " | " | |
| 468 | 1-CH₃-3-CF₃-pyrazol-5-yl | H₃C—NH—CO | " | " | |
| 469 | 1-CH₃-3-CF₃-pyrazol-5-yl | CH₂=CH—CH₂—NH—CO | " | " | |
| 470 | 1-CH₃-3-CF₃-pyrazol-5-yl | (CH₃)₂CH—NH—CO | " | " | |
| 471 | 1-CH₃-3-CF₃-pyrazol-5-yl | (CH₃)₃C—NH—CO | " | " | |
| 472 | 1-CH₃-3-CF₃-pyrazol-5-yl | (CH₃)₂CH—CH₂—NH—CO | " | " | |
| 473 | 1-CH₃-3-CF₃-pyrazol-5-yl | Cl—(CH₂)₃—NH—CO | " | " | |
| 474 | 1-CH₃-3-CF₃-pyrazol-5-yl | cyclohexyl-NH—CO | " | " | |
| 475 | 1-CH₃-3-CF₃-pyrazol-5-yl | C₂H₅—O—CO—CH₂—NH—CO | " | " | |
| 476 | 1-CH₃-3-CF₃-pyrazol-5-yl | benzyl-NH—CO | " | " | |
| 477 | 1-CH₃-3-CF₃-pyrazol-5-yl | C₂H₅—O—CO—(CH₂)₂—NH—CO | " | " | |
| 478 | 1-CH₃-3-CF₃-pyrazol-5-yl | 4-methylbenzyl-NH—CO | " | " | |

TABLE 1-continued (I")

Structure: A-O-[pyridine with R¹ at 4-position, N in ring]-CH₂-N(R⁶)-B

| Example | A | B | R¹ | R⁶ | Melting point [° C.] |
|---|---|---|---|---|---|
| 479 | 1-CH₃-3-CF₃-pyrazol-5-yl | [(CF₃)₂Cl]C—NH—CO | " | " | |
| 480 | 1-CH₃-3-CF₃-pyrazol-5-yl | CF₃—(CF₂)₅—NH—CO | " | " | |
| 481 | 1-CH₃-3-CF₃-pyrazol-5-yl | phenyl-N(CH₃)—CO | " | " | |
| 482 | 1-CH₃-3-CF₃-pyrazol-5-yl | [(CH₃)₂CH—CH₂]₂N—CO | " | " | |
| 483 | 1-CH₃-3-CF₃-pyrazol-5-yl | [(CH₃)₂CH]₂N—CO | " | " | |
| 484 | 1-CH₃-3-CF₃-pyrazol-5-yl | N-pyrrolidinyl-CO | " | " | |
| 485 | 1-CH₃-3-CF₃-pyrazol-5-yl | N-morpholinyl-CO | " | " | |
| 486 | 1-CH₃-3-CF₃-pyrazol-5-yl | cyclopropyl-SO₂ | " | " | |
| 487 | 1-CH₃-3-CF₃-pyrazol-5-yl | H₂C=CH—SO₂ | " | " | |
| 488 | 1-CH₃-3-CF₃-pyrazol-5-yl | CF₃—CH₂—SO₂ | " | " | |
| 489 | 1-CH₃-3-CF₃-pyrazol-5-yl | (CH₃)₂CH—SO₂ | " | " | |
| 490 | 1-CH₃-3-CF₃-pyrazol-5-yl | C₂H₅—SO₂ | " | " | |
| 491 | 1-CH₃-3-CF₃-pyrazol-5-yl | CF₃—SO₂ | " | " | |
| 492 | 1-CH₃-3-CF₃-pyrazol-5-yl | CH₃—SO₂ | " | " | |
| 493 | 1-CH₃-3-CF₃-pyrazol-5-yl | (CH₃)₂N—SO₂ | " | " | |
| 494 | 1-CH₃-3-CF₃-pyrazol-5-yl | Cl₃C—SO₂ | " | " | |
| 495 | 1-CH₃-3-CF₃-pyrazol-5-yl | CH₃—NH—SO₂ | " | " | |
| 496 | 1-CH₃-3-CF₃-pyrazol-5-yl | 2,4,5-trichlorophenyl-SO₂ | " | " | |
| 497 | 1-CH₃-3-CF₃-pyrazol-5-yl | 4-iodophenyl-SO₂ | " | " | |
| 498 | 1-CH₃-3-CF₃-pyrazol-5-yl | benzyl-SO₂ | " | " | |
| 499 | 1-CH₃-3-CF₃-pyrazol-5-yl | 4-nitrophenyl-SO₂ | " | " | |
| 500 | 1-CH₃-3-CF₃-pyrazol-5-yl | 2CF₃-phenyl-SO₂ | " | " | |
| 501 | 1-CH₃-3-CF₃-pyrazol-5-yl | 4-tert-butyl-phenyl-SO₂ | " | " | |
| 502 | 1-CH₃-3-CF₃-pyrazol-5-yl | Cl₂CH—SO₂ | " | " | |
| 503 | 1-CH₃-3-CF₃-pyrazol-5-yl | C₃H₇—SO₂ | " | " | |
| 504 | 1-CH₃-3-CF₃-pyrazol-5-yl | 4-chlorophenyl-SO₂ | " | " | |
| 505 | 1-CH₃-3-CF₃-pyrazol-5-yl | 3-nitrophenyl-SO₂ | " | " | |
| 506 | 1-CH₃-3-CF₃-pyrazol-5-yl | phenyl-SO₂ | " | " | |
| 507 | 1-CH₃-3-CF₃-pyrazol-5-yl | CH₃—(CH₂)₃—NH—CS | " | " | |
| 508 | 1-CH₃-3-CF₃-pyrazol-5-yl | C₂H₅—NH—CS | " | " | |
| 509 | 1-CH₃-3-CF₃-pyrazol-5-yl | Phenyl-CH₂—CH₂—NH—CS | " | " | |
| 510 | 1-CH₃-3-CF₃-pyrazol-5-yl | tert-butyl-NH—CS | " | " | |
| 511 | 1-CH₃-3-CF₃-pyrazol-5-yl | 2-CF₃-phenyl-NH—CS | " | " | |

TABLE 1-continued (I'')

| Example | A | B | R¹ | R⁶ | Melting point [° C.] |
|---|---|---|---|---|---|
| 512 | 1-CH₃-3-CF₃-pyrazol-5-yl | 4-CF₃-phenyl-NH—CS | " | " | |
| 513 | 1-CH₃-3-CF₃-pyrazol-5-yl | phenyl-NH—CS | " | " | |
| 514 | 1-CH₃-3-CF₃-pyrazol-5-yl | cyclohexyl-NH—CS | " | " | |
| 515 | 1-CH₃-3-CF₃-pyrazol-5-yl | (CH₃)₂CH—NH—CS | " | " | |
| 516 | 1-CH₃-3-CF₃-pyrazol-5-yl | CH₃—(CH₂)₇—NH—CS | " | " | |
| 517 | 1-CH₃-3-CF₃-pyrazol-5-yl | CH₃—O—CH₂—CH₂—NH—CS | " | " | |
| 518 | 1-CH₃-3-CF₃-pyrazol-5-yl | benzyl-NH—CS | " | " | |
| 519 | 1-CH₃-3-CF₃-pyrazol-5-yl | CH₃—CHCl—CO | CH₃ | H | |
| 520 | 1-CH₃-3-CF₃-pyrazol-5-yl | structure 1 | " | " | |
| 521 | 1-CH₃-3-CF₃-pyrazol-5-yl | 3-NO₂-4-Cl-benzoyl | " | " | |
| 522 | 1-CH₃-3-CF₃-pyrazol-5-yl | 4-tert-butylbenzoyl | " | " | |
| 523 | 1-CH₃-3-CF₃-pyrazol-5-yl | 2,4,6-trifluorobenzoyl | " | " | 159.0 |
| 524 | 1-CH₃-3-CF₃-pyrazol-5-yl | 3,4-difluorobenzoyl | " | " | |
| 525 | 1-CH₃-3-CF₃-pyrazol-5-yl | 3-trifluoromethylbenzoyl | " | " | |
| 526 | 1-CH₃-3-CF₃-pyrazol-5-yl | 3,4-dichlorobenzoyl | " | " | |
| 527 | 1-CH₃-3-CF₃-pyrazol-5-yl | C₂H₅—O—CO—(CH₂)₃—CO | " | " | |
| 528 | 1-CH₃-3-CF₃-pyrazol-5-yl | CH₃—(CH₂)₇—CO | " | " | |
| 529 | 1-CH₃-3-CF₃-pyrazol-5-yl | phenyl-CH=CH—CO | " | " | |
| 530 | 1-CH₃-3-CF₃-pyrazol-5-yl | Cl—(CH₂)₄—CO | " | " | |
| 531 | 1-CH₃-3-CF₃-pyrazol-5-yl | Cl—(CH₂)₃—CO | " | " | |
| 532 | 1-CH₃-3-CF₃-pyrazol-5-yl | CH₃—CH=CH—CO | " | " | |
| 533 | 1-CH₃-3-CF₃-pyrazol-5-yl | CH₃—CH₂—CO | " | " | 129 |
| 534 | 1-CH₃-3-CF₃-pyrazol-5-yl | (CH₃)₂C=CH—CO | " | " | |
| 535 | 1-CH₃-3-CF₃-pyrazol-5-yl | CH₂=CH—CO | " | " | |
| 536 | 1-CH₃-3-CF₃-pyrazol-5-yl | H—CO | " | " | |
| 537 | 1-CH₃-3-CF₃-pyrazol-5-yl | ClH₂C—CO | " | " | |
| 538 | 1-CH₃-3-CF₃-pyrazol-5-yl | CH₃—CO | " | " | |
| 539 | 1-CH₃-3-CF₃-pyrazol-5-yl | (CH₃)₂CH—CO | " | " | 114 |
| 540 | 1-CH₃-3-CF₃-pyrazol-5-yl | CH₃—O—CH₂—CO | " | " | |
| 541 | 1-CH₃-3-CF₃-pyrazol-5-yl | (CH₃)₂CF—CO | " | " | 81 |
| 542 | 1-CH₃-3-CF₃-pyrazol-5-yl | Cl₂HC—CO | " | " | 142 |
| 543 | 1-CH₃-3-CF₃-pyrazol-5-yl | CH₃—CHF—CO | " | " | 81 |
| 544 | 1-CH₃-3-CF₃-pyrazol-5-yl | CF₃—CO | " | " | 128 |

TABLE 1-continued $$\text{(I'')}$$

| Example | A | B | R$^1$ | R$^6$ | Melting point [° C.] |
|---|---|---|---|---|---|
| 545 | 1-CH$_3$-3-CF$_3$-pyrazol-5-yl | cyclopropyl-CO | " | " | 136 |
| 546 | 1-CH$_3$-3-CF$_3$-pyrazol-5-yl | cyclobutyl-CO | " | " | 127 |
| 547 | 1-CH$_3$-3-CF$_3$-pyrazol-5-yl | 2-furan-CO | " | " | |
| 548 | 1-CH$_3$-3-CF$_3$-pyrazol-5-yl | 2-thienyl-CO | " | " | |
| 549 | 1-CH$_3$-3-CF$_3$-pyrazol-5-yl | CF$_3$—CH$_2$—CO | " | " | 137 |
| 550 | 1-CH$_3$-3-CF$_3$-pyrazol-5-yl | (CF$_3$)$_2$CH—CO | " | " | |
| 551 | 1-CH$_3$-3-CF$_3$-pyrazol-5-yl | tert-butyl-CO | " | " | |
| 552 | 1-CH$_3$-3-CF$_3$-pyrazol-5-yl | 3-cyanobenzoyl | " | " | |
| 553 | 1-CH$_3$-3-CF$_3$-pyrazol-5-yl | (CH$_3$)$_2$CH—CH$_2$—CO | " | " | 86.0 |
| 554 | 1-CH$_3$-3-CF$_3$-pyrazol-5-yl | tert-butyl-CH$_2$—CO | " | " | 93.0 |
| 555 | 1-CH$_3$-3-CF$_3$-pyrazol-5-yl | (C$_2$H$_5$)$_2$CH—CO | " | " | |
| 556 | 1-CH$_3$-3-CF$_3$-pyrazol-5-yl | CH$_3$—CO—O—CH$_2$—CO | " | " | |
| 557 | 1-CH$_3$-3-CF$_3$-pyrazol-5-yl | CH$_3$—O—CO—CH$_2$—CO | " | " | |
| 558 | 1-CH$_3$-3-CF$_3$-pyrazol-5-yl | benzyl-CO | " | " | |
| 559 | 1-CH$_3$-3-CF$_3$-pyrazol-5-yl | CL—CH$_2$—(CH$_3$)$_2$C—CO | " | " | |
| 560 | 1-CH$_3$-3-CF$_3$-pyrazol-5-yl | 4-fluorobenzoyl | " | " | |
| 561 | 1-CH$_3$-3-CF$_3$-pyrazol-5-yl | 2-methoxybenzoyl | " | " | |
| 562 | 1-CH$_3$-3-CF$_3$-pyrazol-5-yl | 4-methoxybenzoyl | " | " | |
| 563 | 1-CH$_3$-3-CF$_3$-pyrazol-5-yl | 4-fluorobenzyl-CO | " | " | |
| 564 | 1-CH$_3$-3-CF$_3$-pyrazol-5-yl | 6-Cl-pyridine-3-CO | " | " | |
| 565 | 1-CH$_3$-3-CF$_3$-pyrazol-5-yl | pyridine-4-CO | " | " | |
| 566 | 1-CH$_3$-3-CF$_3$-pyrazol-5-yl | CH$_3$—O—CO—(CH$_2$)$_4$—CO | " | " | |
| 567 | 1-CH$_3$-3-CF$_3$-pyrazol-5-yl | 2,4,6-trimethylbenzoyl | " | " | |
| 568 | 1-CH$_3$-3-CF$_3$-pyrazol-5-yl | 4-nitrobenzoyl | " | " | |
| 569 | 1-CH$_3$-3-CF$_3$-pyrazol-5-yl | 2,2-dichlorocyclopropyl-CO | " | " | |
| 570 | 1-CH$_3$-3-CF$_3$-pyrazol-5-yl | 2,2-difluorocyclopropyl-CO | " | " | |
| 571 | 1-CH$_3$-3-CF$_3$-pyrazol-5-yl | 2-methylcyclopropyl-CO | " | " | |
| 572 | 1-CH$_3$-3-CF$_3$-pyrazol-5-yl | 1-methylcyclopropyl-CO | " | " | oil |
| 573 | 1-CH$_3$-3-CF$_3$-pyrazol-5-yl | 3-(CF$_3$—O)-benzoyl | " | " | |
| 574 | 1-CH$_3$-3-CF$_3$-pyrazol-5-yl | 2,5-DiCF$_3$-benzoyl | " | " | |
| 575 | 1-CH$_3$-3-CF$_3$-pyrazol-5-yl | 2-Br-5-methoxybenzoyl | " | " | |
| 576 | 1-CH$_3$-3-CF$_3$-pyrazol-5-yl | 1-CH$_3$-2,2-dichlorocyclopropyl-CO | " | " | |
| 577 | 1-CH$_3$-3-CF$_3$-pyrazol-5-yl | 2,2,3,3-tetramethyl-cyclopropyl-CO | " | " | |

TABLE 1-continued (Structure with A-O- attached to pyridine ring, R¹ at position 4, and -CH₂-N(R⁶)-B at position 6) (I'')

| Example | A | B | R¹ | R⁶ | Melting point [° C.] |
|---|---|---|---|---|---|
| 578 | 1-CH₃-3-CF₃-pyrazol-5-yl | 2,3,4,5,6-pentafluorobenzoyl | " | " | |
| 579 | 1-CH₃-3-CF₃-pyrazol-5-yl | structure 2 | " | " | |
| 580 | 1-CH₃-3-CF₃-pyrazol-5-yl | C₂H₅—O—CO—CO | " | " | |
| 581 | 1-CH₃-3-CF₃-pyrazol-5-yl | CH₃—O—CO | " | " | oil |
| 582 | 1-CH₃-3-CF₃-pyrazol-5-yl | CH₃—CH₂—O—CO | " | " | |
| 583 | 1-CH₃-3-CF₃-pyrazol-5-yl | benzyl-O—CO | " | " | |
| 584 | 1-CH₃-3-CF₃-pyrazol-5-yl | C₄H₉—O—CO | " | " | |
| 585 | 1-CH₃-3-CF₃-pyrazol-5-yl | (CH₃)₂CH—CH₂—O—CO | " | " | |
| 586 | 1-CH₃-3-CF₃-pyrazol-5-yl | (CH₃)₂CH—O—CO | " | " | |
| 587 | 1-CH₃-3-CF₃-pyrazol-5-yl | (CH₃)₃C—O—CO | " | " | |
| 588 | 1-CH₃-3-CF₃-pyrazol-5-yl | C₃H₇—O—CO | " | " | |
| 589 | 1-CH₃-3-CF₃-pyrazol-5-yl | 4-NO₂benzyl-O—CO | " | " | |
| 590 | 1-CH₃-3-CF₃-pyrazol-5-yl | CH₂=CH—CH₂—O—CO | " | " | |
| 591 | 1-CH₃-3-CF₃-pyrazol-5-yl | cyclopentyl-O—CO | " | " | |
| 592 | 1-CH₃-3-CF₃-pyrazol-5-yl | CF₃—CH₂—O—CO | " | " | |
| 593 | 1-CH₃-3-CF₃-pyrazol-5-yl | (CH₃)₂N—CO | " | " | |
| 594 | 1-CH₃-3-CF₃-pyrazol-5-yl | C₂H₅—NH—CO | " | " | |
| 595 | 1-CH₃-3-CF₃-pyrazol-5-yl | 2,4-difluorophenyl-NH—CO | " | " | |
| 596 | 1-CH₃-3-CF₃-pyrazol-5-yl | 3-fluorophenyl-NH—CO | " | " | |
| 597 | 1-CH₃-3-CF₃-pyrazol-5-yl | H₃C—NH—CO | " | " | |
| 598 | 1-CH₃-3-CF₃-pyrazol-5-yl | CH₂=CH—CH₂—NH—CO | " | " | |
| 599 | 1-CH₃-3-CF₃-pyrazol-5-yl | (CH₃)₂CH—NH—CO | " | " | |
| 600 | 1-CH₃-3-CF₃-pyrazol-5-yl | (CH₃)₃C—NH—CO | " | " | |
| 601 | 1-CH₃-3-CF₃-pyrazol-5-yl | (CH₃)₂CH—CH₂—NH—CO | " | " | |
| 602 | 1-CH₃-3-CF₃-pyrazol-5-yl | Cl—(CH₂)₃—NH—CO | " | " | |
| 603 | 1-CH₃-3-CF₃-pyrazol-5-yl | cyclohexyl-NH—CO | " | " | |
| 604 | 1-CH₃-3-CF₃-pyrazol-5-yl | C₂H₅—O—CO—CH₂—NH—CO | " | " | |
| 605 | 1-CH₃-3-CF₃-pyrazol-5-yl | benzyl-NH—CO | " | " | |
| 606 | 1-CH₃-3-CF₃-pyrazol-5-yl | C₂H₅—O—CO—(CH₂)₂—NH—CO | " | " | |
| 607 | 1-CH₃-3-CF₃-pyrazol-5-yl | 4-methylbenzyl-NH—CO | " | " | |
| 608 | 1-CH₃-3-CF₃-pyrazol-5-yl | [(CF₃)₂Cl]C—NH—CO | " | " | |
| 609 | 1-CH₃-3-CF₃-pyrazol-5-yl | CF₃—(CF₂)₅—NH—CO | " | " | |
| 610 | 1-CH₃-3-CF₃-pyrazol-5-yl | phenyl-N(CH₃)—CO | " | " | |

TABLE 1-continued (structure with R¹ at pyridine 4-position, A-O at 2-position, and -CH₂-N(R⁶)-B at 6-position) (I")

| Example | A | B | R¹ | R⁶ | Melting point [° C.] |
|---|---|---|---|---|---|
| 611 | 1-CH₃-3-CF₃-pyrazol-5-yl | [(CH₃)₂CH—CH₂]₂N—CO | " | " | |
| 612 | 1-CH₃-3-CF₃-pyrazol-5-yl | [(CH₃)₂CH]₂N—CO | " | " | |
| 613 | 1-CH₃-3-CF₃-pyrazol-5-yl | N-pyrrolidinyl-CO | " | " | |
| 614 | 1-CH₃-3-CF₃-pyrazol-5-yl | N-morpholinyl-CO | " | " | |
| 615 | 1-CH₃-3-CF₃-pyrazol-5-yl | cyclopropyl-SO₂ | " | " | |
| 616 | 1-CH₃-3-CF₃-pyrazol-5-yl | H₂C=CH—SO₂ | " | " | |
| 617 | 1-CH₃-3-CF₃-pyrazol-5-yl | CF₃—CH₂—SO₂ | " | " | |
| 618 | 1-CH₃-3-CF₃-pyrazol-5-yl | (CH₃)₂CH—SO₂ | " | " | |
| 619 | 1-CH₃-3-CF₃-pyrazol-5-yl | C₂H₅—SO₂ | " | " | |
| 620 | 1-CH₃-3-CF₃-pyrazol-5-yl | CF₃—SO₂ | " | " | |
| 621 | 1-CH₃-3-CF₃-pyrazol-5-yl | CH₃—SO₂ | " | " | |
| 622 | 1-CH₃-3-CF₃-pyrazol-5-yl | CF₃—SO₂ | " | CF₃—SO₂ | |
| 623 | 1-CH₃-3-CF₃-pyrazol-5-yl | (CH₃)₂N—SO₂ | " | H | |
| 624 | 1-CH₃-3-CF₃-pyrazol-5-yl | Cl₃C—SO₂ | " | " | |
| 625 | 1-CH₃-3-CF₃-pyrazol-5-yl | CH₃—NH—SO₂ | " | " | |
| 626 | 1-CH₃-3-CF₃-pyrazol-5-yl | 2,4,5-trichlorophenyl-SO₂ | " | " | |
| 627 | 1-CH₃-3-CF₃-pyrazol-5-yl | 4-iodophenyl-SO₂ | " | " | |
| 628 | 1-CH₃-3-CF₃-pyrazol-5-yl | benzyl-SO₂ | " | " | |
| 629 | 1-CH₃-3-CF₃-pyrazol-5-yl | 4-nitrophenyl-SO₂ | " | " | |
| 630 | 1-CH₃-3-CF₃-pyrazol-5-yl | 2-CF₃-phenyl-SO₂ | " | " | |
| 631 | 1-CH₃-3-CF₃-pyrazol-5-yl | 4-tert-butyl-phenyl-SO₂ | " | " | |
| 632 | 1-CH₃-3-CF₃-pyrazol-5-yl | Cl₂CH—SO₂ | " | " | |
| 633 | 1-CH₃-3-CF₃-pyrazol-5-yl | C₃H₇—SO₂ | " | " | |
| 634 | 1-CH₃-3-CF₃-pyrazol-5-yl | 4-chlorophenyl-SO₂ | " | " | |
| 635 | 1-CH₃-3-CF₃-pyrazol-5-yl | 3-nitrophenyl-SO₂ | " | " | |
| 636 | 1-CH₃-3-CF₃-pyrazol-5-yl | phenyl-SO₂ | " | " | |
| 637 | 1-CH₃-3-CF₃-pyrazol-5-yl | CH₃—(CH₂)₃—NH—CS | " | " | |
| 638 | 1-CH₃-3-CF₃-pyrazol-5-yl | C₂H₅—NH—CS | " | " | |
| 639 | 1-CH₃-3-CF₃-pyrazol-5-yl | Phenyl-CH₂—CH₂—NH—CS | " | " | |
| 640 | 1-CH₃-3-CF₃-pyrazol-5-yl | tert-butyl-NH—CS | " | " | |
| 641 | 1-CH₃-3-CF₃-pyrazol-5-yl | 2-CF₃-phenyl-NH—CS | " | " | |
| 642 | 1-CH₃-3-CF₃-pyrazol-5-yl | 4-CF₃-phenyl-NH—CS | " | " | |
| 643 | 1-CH₃-3-CF₃-pyrazol-5-yl | phenyl-NH—CS | " | " | |

TABLE 1-continued

Structure (I"): A–O–[pyridine with R¹ at 4-position, N at 1-position]–CH₂–N(R⁶)–B

| Example | A | B | R¹ | R⁶ | Melting point [° C.] |
|---|---|---|---|---|---|
| 644 | 1-CH₃-3-CF₃-pyrazol-5-yl | cyclohexyl-NH—CS | " | " | |
| 645 | 1-CH₃-3-CF₃-pyrazol-5-yl | (CH₃)₂CH—NH—CS | " | " | |
| 646 | 1-CH₃-3-CF₃-pyrazol-5-yl | CH₃—(CH₂)₇—NH—CS | " | " | |
| 647 | 1-CH₃-3-CF₃-pyrazol-5-yl | CH₃—O—CH₂—CH₂—NH—CS | " | " | |
| 648 | 1-CH₃-3-CF₃-pyrazol-5-yl | benzyl-NH—CS | " | " | |
| 649 | 1-CH₃-3-CF₃-pyrazol-5-yl | CH₃—CHCl—CO | CH₃ | CH₃ | |
| 650 | 1-CH₃-3-CF₃-pyrazol-5-yl | structure 1 | " | " | |
| 651 | 1-CH₃-3-CF₃-pyrazol-5-yl | 3-NO₂-4-Cl-benzoyl | " | " | |
| 652 | 1-CH₃-3-CF₃-pyrazol-5-yl | 4-tert-butylbenzoyl | " | " | |
| 653 | 1-CH₃-3-CF₃-pyrazol-5-yl | 2,4,6-trifluorobenzoyl | " | " | |
| 654 | 1-CH₃-3-CF₃-pyrazol-5-yl | 3,4-difluorobenzoyl | " | " | |
| 655 | 1-CH₃-3-CF₃-pyrazol-5-yl | 3-trifluoromethylbenzoyl | " | " | |
| 656 | 1-CH₃-3-CF₃-pyrazol-5-yl | 3,4-dichlorobenzoyl | " | " | |
| 657 | 1-CH₃-3-CF₃-pyrazol-5-yl | C₂H₅—O—CO—(CH₂)₃—CO | " | " | |
| 658 | 1-CH₃-3-CF₃-pyrazol-5-yl | CH₃—(CH₂)₇—CO | " | " | |
| 659 | 1-CH₃-3-CF₃-pyrazol-5-yl | phenyl-CH=CH—CO | " | " | |
| 660 | 1-CH₃-3-CF₃-pyrazol-5-yl | Cl—(CH₂)₄—CO | " | " | |
| 661 | 1-CH₃-3-CF₃-pyrazol-5-yl | Cl—(CH₂)₃—CO | " | " | |
| 662 | 1-CH₃-3-CF₃-pyrazol-5-yl | CH₃—CH=CH—CO | " | " | |
| 663 | 1-CH₃-3-CF₃-pyrazol-5-yl | CH₃—CH₂—CO | " | " | |
| 664 | 1-CH₃-3-CF₃-pyrazol-5-yl | (CH₃)₂C=CH—CO | " | " | |
| 665 | 1-CH₃-3-CF₃-pyrazol-5-yl | CH₂=CH—CO | " | " | |
| 666 | 1-CH₃-3-CF₃-pyrazol-5-yl | H—CO | " | " | |
| 667 | 1-CH₃-3-CF₃-pyrazol-5-yl | ClH₂C—CO | " | " | |
| 668 | 1-CH₃-3-CF₃-pyrazol-5-yl | CH₃—CO | " | " | |
| 669 | 1-CH₃-3-CF₃-pyrazol-5-yl | (CH₃)₂CH—CO | " | " | |
| 670 | 1-CH₃-3-CF₃-pyrazol-5-yl | CH₃—O—CH₂—CO | " | " | |
| 671 | 1-CH₃-3-CF₃-pyrazol-5-yl | (CH₃)₂CF—CO | " | " | |
| 672 | 1-CH₃-3-CF₃-pyrazol-5-yl | Cl₂HC—CO | " | " | |
| 673 | 1-CH₃-3-CF₃-pyrazol-5-yl | CH₃—CHF—CO | " | " | |
| 674 | 1-CH₃-3-CF₃-pyrazol-5-yl | CF₃—CO | " | " | |
| 675 | 1-CH₃-3-CF₃-pyrazol-5-yl | cyclopropyl-CO | " | " | |
| 676 | 1-CH₃-3-CF₃-pyrazol-5-yl | cyclobutyl-CO | " | " | |

TABLE 1-continued (I'')

Structure: pyridine ring with A-O at position 2, R¹ at position 4, and CH₂-N(R⁶)-B at position 6.

| Example | A | B | R¹ | R⁶ | Melting point [° C.] |
|---|---|---|---|---|---|
| 677 | 1-CH₃-3-CF₃-pyrazol-5-yl | 2-furan-CO | " | " | |
| 678 | 1-CH₃-3-CF₃-pyrazol-5-yl | 2-thienyl-CO | " | " | |
| 679 | 1-CH₃-3-CF₃-pyrazol-5-yl | CF₃—CH₂—CO | " | " | |
| 680 | 1-CH₃-3-CF₃-pyrazol-5-yl | (CF₃)₂CH—CO | " | " | |
| 681 | 1-CH₃-3-CF₃-pyrazol-5-yl | tert-butyl-CO | " | " | |
| 682 | 1-CH₃-3-CF₃-pyrazol-5-yl | 3-cyanobenzoyl | " | " | |
| 683 | 1-CH₃-3-CF₃-pyrazol-5-yl | (CH₃)₂CH—CH₂—CO | " | " | |
| 684 | 1-CH₃-3-CF₃-pyrazol-5-yl | tert-butyl-CH₂—CO | " | " | |
| 685 | 1-CH₃-3-CF₃-pyrazol-5-yl | (C₂H₅)₂CH—CO | " | " | |
| 686 | 1-CH₃-3-CF₃-pyrazol-5-yl | CH₃—CO—O—CH₂—CO | " | " | |
| 687 | 1-CH₃-3-CF₃-pyrazol-5-yl | CH₃—O—CO—CH₂—CO | " | " | |
| 688 | 1-CH₃-3-CF₃-pyrazol-5-yl | benzyl-CO | " | " | |
| 689 | 1-CH₃-3-CF₃-pyrazol-5-yl | CL—CH₂—(CH₃)₂C—CO | " | " | |
| 690 | 1-CH₃-3-CF₃-pyrazol-5-yl | 4-fluorobenzoyl | " | " | |
| 691 | 1-CH₃-3-CF₃-pyrazol-5-yl | 2-methoxybenzoyl | " | " | |
| 692 | 1-CH₃-3-CF₃-pyrazol-5-yl | 4-methoxybenzoyl | " | " | |
| 693 | 1-CH₃-3-CF₃-pyrazol-5-yl | 4-fluorobenzoyl-CO | " | " | |
| 694 | 1-CH₃-3-CF₃-pyrazol-5-yl | 6-Cl-pyridine-3-CO | " | " | |
| 695 | 1-CH₃-3-CF₃-pyrazol-5-yl | pyridine-4-CO | " | " | |
| 696 | 1-CH₃-3-CF₃-pyrazol-5-yl | CH₃—O—CO—(CH₂)₄—CO | " | " | |
| 697 | 1-CH₃-3-CF₃-pyrazol-5-yl | 2,4,6-trimethoxybenzoyl | " | " | |
| 698 | 1-CH₃-3-CF₃-pyrazol-5-yl | 4-nitrobenzoyl | " | " | |
| 699 | 1-CH₃-3-CF₃-pyrazol-5-yl | 2,2-dichlorocyclopropyl-CO | " | " | |
| 700 | 1-CH₃-3-CF₃-pyrazol-5-yl | 2,2-difluorocyclopropyl-CO | " | " | |
| 701 | 1-CH₃-3-CF₃-pyrazol-5-yl | 2-methylcyclopropyl-CO | " | " | |
| 702 | 1-CH₃-3-CF₃-pyrazol-5-yl | 1-methylcyclopropyl-CO | " | " | |
| 703 | 1-CH₃-3-CF₃-pyrazol-5-yl | 3-(CF₃—O)-benzoyl | " | " | |
| 704 | 1-CH₃-3-CF₃-pyrazol-5-yl | 2,5-DiCF₃-benzoyl | " | " | |
| 705 | 1-CH₃-3-CF₃-pyrazol-5-yl | 2-Br-5-methoxybenzoyl | " | " | |
| 706 | 1-CH₃-3-CF₃-pyrazol-5-yl | 1-CH₃-2,2-dichlorocyclopropyl-CO | " | " | |
| 707 | 1-CH₃-3-CF₃-pyrazol-5-yl | 2,2,3,3-tetramethyl-cyclopropyl-CO | " | " | |
| 708 | 1-CH₃-3-CF₃-pyrazol-5-yl | 2,3,4,5,6-pentafluorobenzoyl | " | " | |
| 709 | 1-CH₃-3-CF₃-pyrazol-5-yl | structure 2 | " | " | |

TABLE 1-continued (I")

| Example | A | B | R¹ | R⁶ | Melting point [° C.] |
|---|---|---|---|---|---|
| 710 | 1-CH$_3$-3-CF$_3$-pyrazol-5-yl | C$_2$H$_5$—O—CO—CO | " | " | |
| 711 | 1-CH$_3$-3-CF$_3$-pyrazol-5-yl | CH$_3$—O—CO | " | " | |
| 712 | 1-CH$_3$-3-CF$_3$-pyrazol-5-yl | CH$_3$—CH$_2$—O—CO | " | " | |
| 713 | 1-CH$_3$-3-CF$_3$-pyrazol-5-yl | benzyl-O—CO | " | " | |
| 714 | 1-CH$_3$-3-CF$_3$-pyrazol-5-yl | C$_4$H$_9$—O—CO | " | " | |
| 715 | 1-CH$_3$-3-CF$_3$-pyrazol-5-yl | (CH$_3$)$_2$CH—CH$_2$—O—CO | " | " | |
| 716 | 1-CH$_3$-3-CF$_3$-pyrazol-5-yl | (CH$_3$)$_2$CH—O—CO | " | " | |
| 717 | 1-CH$_3$-3-CF$_3$-pyrazol-5-yl | (CH$_3$)$_3$C—O—CO | " | " | |
| 718 | 1-CH$_3$-3-CF$_3$-pyrazol-5-yl | C$_3$H$_7$—O—CO | " | " | |
| 719 | 1-CH$_3$-3-CF$_3$-pyrazol-5-yl | 4-NO$_2$benzyl-CO—CO | " | " | |
| 720 | 1-CH$_3$-3-CF$_3$-pyrazol-5-yl | CH$_2$=CH—CH$_2$—O—CO | " | " | |
| 721 | 1-CH$_3$-3-CF$_3$-pyrazol-5-yl | cyclopentyl-O—CO | " | " | |
| 722 | 1-CH$_3$-3-CF$_3$-pyrazol-5-yl | CF$_3$—CH$_2$—O—CO | " | " | |
| 723 | 1-CH$_3$-3-CF$_3$-pyrazol-5-yl | (CH$_3$)$_2$N—CO | " | " | |
| 724 | 1-CH$_3$-3-CF$_3$-pyrazol-5-yl | C$_2$H$_5$—NH—CO | " | " | |
| 725 | 1-CH$_3$-3-CF$_3$-pyrazol-5-yl | 2,4-difluorophenyl-NH—CO | " | " | |
| 726 | 1-CH$_3$-3-CF$_3$-pyrazol-5-yl | 3-fluorophenyl-NH—CO | " | " | |
| 727 | 1-CH$_3$-3-CF$_3$-pyrazol-5-yl | H$_3$C—NH—CO | " | " | |
| 728 | 1-CH$_3$-3-CF$_3$-pyrazol-5-yl | CH$_2$=CH—CH$_2$—NH—CO | " | " | |
| 729 | 1-CH$_3$-3-CF$_3$-pyrazol-5-yl | (CH$_3$)$_2$CH—NH—CO | " | " | |
| 730 | 1-CH$_3$-3-CF$_3$-pyrazol-5-yl | (CH$_3$)$_3$C—NH—CO | " | " | |
| 731 | 1-CH$_3$-3-CF$_3$-pyrazol-5-yl | (CH$_3$)$_2$CH—CH$_2$—NH—CO | " | " | |
| 732 | 1-CH$_3$-3-CF$_3$-pyrazol-5-yl | Cl—(CH$_2$)$_3$—NH—CO | " | " | |
| 733 | 1-CH$_3$-3-CF$_3$-pyrazol-5-yl | cyclohexyl-NH—CO | " | " | |
| 734 | 1-CH$_3$-3-CF$_3$-pyrazol-5-yl | C$_2$H$_5$—O—CO—CH$_2$—NH—CO | " | " | |
| 735 | 1-CH$_3$-3-CF$_3$-pyrazol-5-yl | benzyl-NH—CO | " | " | |
| 736 | 1-CH$_3$-3-CF$_3$-pyrazol-5-yl | C$_2$H$_5$—O—CO—(CH$_2$)$_2$—NH—CO | " | " | |
| 737 | 1-CH$_3$-3-CF$_3$-pyrazol-5-yl | 4-methylbenzyl-NH—CO | " | " | |
| 738 | 1-CH$_3$-3-CF$_3$-pyrazol-5-yl | ∂(CF$_3$)$_2$Cl]C—NH—CO | " | " | |
| 739 | 1-CH$_3$-3-CF$_3$-pyrazol-5-yl | CF$_3$—(CF$_2$)$_5$—NH—CO | " | " | |
| 740 | 1-CH$_3$-3-CF$_3$-pyrazol-5-yl | phenyl-N(CH$_3$)—CO | " | " | |
| 741 | 1-CH$_3$-3-CF$_3$-pyrazol-5-yl | [(CH$_3$)$_2$CH—CH$_2$]$_2$N—CO | " | " | |
| 742 | 1-CH$_3$-3-CF$_3$-pyrazol-5-yl | [(CH$_3$)$_2$CH]$_2$N—CO | " | " | |

TABLE 1-continued (I")

| Example | A | B | R¹ | R⁶ | Melting point [°C.] |
|---|---|---|---|---|---|
| 743 | 1-CH₃-3-CF₃-pyrazol-5-yl | N-pyrrolidinyl-CO | " | " | |
| 744 | 1-CH₃-3-CF₃-pyrazol-5-yl | N-morpholinyl-CO | " | " | |
| 745 | 1-CH₃-3-CF₃-pyrazol-5-yl | cyclopropyl-SO₂ | " | " | |
| 746 | 1-CH₃-3-CF₃-pyrazol-5-yl | H₂C=CH—SO₂ | " | " | |
| 747 | 1-CH₃-3-CF₃-pyrazol-5-yl | CF₃—CH₂—SO₂ | " | " | |
| 748 | 1-CH₃-3-CF₃-pyrazol-5-yl | (CH₃)₂CH—SO₂ | " | " | |
| 749 | 1-CH₃-3-CF₃-pyrazol-5-yl | C₂H₅—SO₂ | " | " | |
| 750 | 1-CH₃-3-CF₃-pyrazol-5-yl | CF₃—SO₂ | " | " | |
| 751 | 1-CH₃-3-CF₃-pyrazol-5-yl | CH₃—SO₂ | " | " | |
| 752 | 1-CH₃-3-CF₃-pyrazol-5-yl | (CH₃)₂N—SO₂ | " | " | |
| 753 | 1-CH₃-3-CF₃-pyrazol-5-yl | Cl₃C—SO₂ | " | " | |
| 754 | 1-CH₃-3-CF₃-pyrazol-5-yl | CH₃—NH—SO₂ | " | " | |
| 755 | 1-CH₃-3-CF₃-pyrazol-5-yl | 2,4,5-trichlorophenyl-SO₂ | " | " | |
| 756 | 1-CH₃-3-CF₃-pyrazol-5-yl | 4-Iodophenyl-SO₂ | " | " | |
| 757 | 1-CH₃-3-CF₃-pyrazol-5-yl | benzyl-SO₂ | " | " | |
| 758 | 1-CH₃-3-CF₃-pyrazol-5-yl | 4-nitrophenyl-SO₂ | " | " | |
| 759 | 1-CH₃-3-CF₃-pyrazol-5-yl | 2-CF₃-phenyl-SO₂ | " | " | |
| 760 | 1-CH₃-3-CF₃-pyrazol-5-yl | 4-tert-butyl-phenyl-SO₂ | " | " | |
| 761 | 1-CH₃-3-CF₃-pyrazol-5-yl | Cl₂CH—SO₂ | " | " | |
| 762 | 1-CH₃-3-CF₃-pyrazol-5-yl | C₃H₇—SO₂ | " | " | |
| 763 | 1-CH₃-3-CF₃-pyrazol-5-yl | 4-chlorophenyl-SO₂ | " | " | |
| 764 | 1-CH₃-3-CF₃-pyrazol-5-yl | 3-nitrophenyl-SO₂ | " | " | |
| 765 | 1-CH₃-3-CF₃-pyrazol-5-yl | phenyl-SO₂ | " | " | |
| 766 | 1-CH₃-3-CF₃-pyrazol-5-yl | CH₃—(CH₂)₃—NH—CS | " | " | |
| 767 | 1-CH₃-3-CF₃-pyrazol-5-yl | C₂H₅—NH—CS | " | " | |
| 768 | 1-CH₃-3-CF₃-pyrazol-5-yl | Phenyl-CH₂—CH₂—NH—CS | " | " | |
| 769 | 1-CH₃-3-CF₃-pyrazol-5-yl | tert-butyl-NH—CS | " | " | |
| 770 | 1-CH₃-3-CF₃-pyrazol-5-yl | 2-CF₃-phenyl-NH—CS | " | " | |
| 771 | 1-CH₃-3-CF₃-pyrazol-5-yl | 4-CF₃-phenyl-NH—CS | " | " | |
| 772 | 1-CH₃-3-CF₃-pyrazol-5-yl | phenyl-NH—CS | " | " | |
| 773 | 1-CH₃-3-CF₃-pyrazol-5-yl | cyclohexyl-NH—CS | " | " | |
| 774 | 1-CH₃-3-CF₃-pyrazol-5-yl | (CH₃)₂CH—NH—CS | " | " | |
| 775 | 1-CH₃-3-CF₃-pyrazol-5-yl | CH₃—(CH₂)₇—NH—CS | " | " | |

TABLE 1-continued (I")

| Example | A | B | R¹ | R⁶ | Melting point [° C.] |
|---|---|---|---|---|---|
| 776 | 1-CH₃-3-CF₃-pyrazol-5-yl | CH₃—O—CH₂—CH₂—NH—CS | " | " | |
| 777 | 1-CH₃-3-CF₃-pyrazol-5-yl | benzyl-NH—CS | " | " | |
| 778 | 3-CF₃-phenyl | CH₃—CHCl—CO | CH₃ | H | |
| 779 | " | structure 1 | " | " | |
| 780 | " | 3-NO₂-4-Cl-benzoyl | " | " | |
| 781 | " | 4-tert-butylbenzoyl | " | " | |
| 782 | " | 2,4,6-trifluorobenzoyl | " | " | |
| 783 | " | 3,4-difluorobenzoyl | " | " | |
| 784 | " | 3-trifluoromethylbenzoyl | " | " | |
| 785 | " | 3,4-dichlorobenzoyl | " | " | |
| 786 | " | C₂H₅—O—CO—(CH₂)₃—CO | " | " | |
| 787 | " | CH₃—(CH₂)₇—CO | " | " | |
| 788 | " | phenyl-CH=CH—CO | " | " | |
| 789 | " | Cl—(CH₂)₄—CO | " | " | |
| 790 | " | Cl—(CH₂)₃—CO | " | " | |
| 791 | " | CH₃—CH₂CH—CO | " | " | |
| 792 | " | CH₃—CH₂—CO | " | " | |
| 793 | " | (CH₃)₂C=CH—CO | " | " | |
| 794 | " | CH₂=CH—CO | " | " | |
| 795 | " | H—CO | " | " | |
| 796 | " | ClH₂C—CO | " | " | |
| 797 | " | CH₃—CO | " | " | |
| 798 | " | (CH₃)₂CH—CO | " | " | |
| 799 | " | CH₃—O—CH₂—CO | " | " | |
| 800 | " | (CH₃)₂CF—CO | " | " | |
| 801 | " | Cl₂HC—CO | " | " | |
| 802 | " | CH₃—CHF—CO | " | " | |
| 803 | " | CF₃—CO | " | " | |
| 804 | " | cyclopropyl-CO | " | " | |
| 805 | " | cyclobutyl-CO | " | " | |
| 806 | " | 2-furan-CO | " | " | |
| 807 | " | 2-thienyl-CO | " | " | |
| 808 | " | CF₃—CH₂—CO | " | " | |
| 809 | " | (CF₃)₂CH—CO | " | " | |
| 810 | " | tert-butyl-CO | " | " | |
| 811 | " | 3-cyanobenzoyl | " | " | |
| 812 | " | (CH₃)₂CH—CH₂—CO | " | " | |
| 813 | " | tert-butyl-CH₂—CO | " | " | |
| 814 | " | (C₂H₅)₂CH—CO | " | " | |
| 815 | " | CH₃—CO—O—CH₂—CO | " | " | |
| 816 | " | CH₃—O—CO—CH₂—CO | " | " | |
| 817 | " | benzyl-CO | " | " | |
| 818 | " | CL—CH₂—(CH₃)₂C—CO | " | " | |
| 819 | " | 4-fluorobenzoyl | " | " | |
| 820 | " | 2-methoxybenzoyl | " | " | |
| 821 | " | 4-methoxybenzoyl | " | " | |
| 822 | " | 4-fluorobenzoyl-CO | " | " | |
| 823 | " | 6-Cl-pyridine-3-CO | " | " | |
| 824 | " | pyridine-4-CO | " | " | |
| 825 | " | CH₃—O—CO—(CH₂)₄—CO | " | " | |
| 826 | " | 2,4,6-trimethylbenzoyl | " | " | |
| 827 | " | 4-nitrobenzoyl | " | " | |
| 828 | " | 2,2-dichlorocyclopropyl-CO | " | " | |
| 829 | " | 2,2-difluorocyclopropyl-CO | " | " | |
| 830 | " | 2-methylcyclopropyl-CO | " | " | |
| 831 | " | 1-methylcyclopropyl-CO | " | " | |
| 832 | " | 3-(CF₃—O)-benzoyl | " | " | |
| 833 | " | 2,5-DiCF₃-benzoyl | " | " | |
| 834 | " | 2-Br-5-methoxybenzoyl | " | " | |
| 835 | " | 1-CH₃-2,2-dichlorocyclopropyl-CO | " | " | |
| 836 | " | 2,2,3,3-tetramethyl-cyclopropyl-CO | " | " | |
| 837 | " | 2,3,4,5,6-pentafluorobenzoyl | " | " | |
| 838 | " | structure 2 | " | " | |

TABLE 1-continued

Structure (I''): A—O—[pyridine with R¹ at 4-position, N at ring position 1]—CH₂—N(R⁶)—B

| Example | A | B | R¹ | R⁶ | Melting point [° C.] |
|---|---|---|---|---|---|
| 839 | " | C₂H₅—O—CO—CO | " | " | |
| 840 | " | CH₃—O—CO | " | " | |
| 841 | " | CH₃—CH₂—O—CO | " | " | |
| 842 | " | benzoyl-O—CO | " | " | |
| 843 | " | C₄H₉—O—CO | " | " | |
| 844 | " | (CH₃)₂CH—CH₂—O—CO | " | " | |
| 845 | " | (CH₃)₂CH—O—CO | " | " | |
| 846 | " | (CH₃)₃C—O—CO | " | " | |
| 847 | " | C₃H₇—O—CO | " | " | |
| 848 | " | 4-NO₂-benzyl-O—CO | " | " | |
| 849 | " | CH₂=CH—CH₂—O—CO | " | " | |
| 850 | " | cyclopentyl-O—CO | " | " | |
| 851 | " | CF₃CH₂—O—CO | " | " | |
| 852 | " | (CH₃)₂N—CO | " | " | |
| 853 | " | C₂H₅—NH—CO | " | " | |
| 854 | " | 2,4-difluorophenyl-NH—CO | " | " | |
| 855 | " | 3-fluorophenyl-NH—CO | " | " | |
| 856 | " | H₃C—NH—CO | " | " | |
| 857 | " | CH₂=CH—CH₂—NH—CO | " | " | |
| 858 | " | (CH₃)₂CH—NH—CO | " | " | |
| 859 | " | (CH₃)₃C—NH—CO | " | " | |
| 860 | " | (CH₃)₂CH—CH₂—NH—CO | " | " | |
| 861 | " | Cl—(CH₂)₃—NH—CO | " | " | |
| 862 | " | cyclohexyl-NH—CO | " | " | |
| 863 | " | C₂H₅—O—CO—CH₂—NH—CO | " | " | |
| 864 | " | benzyl-NH—CO | " | " | |
| 865 | " | C₂H₅—O—CO—(CH₂)₂—NH—CO | " | " | |
| 866 | " | 4-methylbenzyl-NH—CO | " | " | |
| 867 | " | [(CF₃)₂Cl]C—NH—CO | " | " | |
| 868 | " | CF₃—(CF₂)₅—NH—CO | " | " | |
| 869 | " | phenyl-N(CH₃)—CO | " | " | |
| 870 | " | [(CH₃)₂CH—CH₂]₂N—CO | " | " | |
| 871 | " | [(CH₃)₂CH]₂N—CO | " | " | |
| 872 | " | N-pyrrolidinyl-CO | " | " | |
| 873 | " | N-morpholinyl-CO | " | " | |
| 874 | " | cyclopropyl-SO₂ | " | " | |
| 875 | " | H₂C=CH—SO₂ | " | " | |
| 876 | " | CF₃—CH₂—SO₂ | " | " | |
| 877 | " | (CH₃)₂CH—SO₂ | " | " | |
| 878 | " | C₂H₅—SO₂ | " | " | |
| 879 | " | CF₃—SO₂ | " | " | |
| 880 | " | CH₃—SO₂ | " | " | |
| 881 | " | CF₃—SO₂ | " | CF₃—SO₂ | |
| 882 | " | (CH₃)₂N—SO₂ | " | H | |
| 883 | " | Cl₃C—SO₂ | " | " | |
| 884 | " | CH₃—NH—SO₂ | " | " | |
| 885 | " | 2,4,5-trichlorophenyl-SO₂ | " | " | |
| 886 | " | 4-iodophenyl-SO₂ | " | " | |
| 887 | " | benzyl-SO₂ | " | " | |
| 888 | " | 4-nitrophenyl-SO₂ | " | " | |
| 889 | " | 2-CF₃-phenyl-SO₂ | " | " | |
| 890 | " | 4-tert-butylphenyl-SO₂ | " | " | |
| 891 | " | Cl₂CH—SO₂ | " | " | |
| 892 | " | C₃H₇—SO₂ | " | " | |
| 893 | " | 4-chlorophenyl-SO₂ | " | " | |
| 894 | " | 3-nitrophenyl-SO₂ | " | " | |
| 895 | " | phenyl-SO₂ | " | " | |
| 896 | " | CH₃—(CH₂)₃—NH—CS | " | " | |
| 897 | " | C₂H₅—NH—CS | " | " | |
| 898 | " | Phenyl-CH₂—CH₂—NH—CS | " | " | |
| 899 | " | tert-butyl-NH—CS | " | " | |
| 900 | " | 2-CF₃-phenyl-NH—CS | " | " | |
| 901 | " | 4-CF₃-phenyl-NH—CS | " | " | |
| 902 | " | phenyl-NH—CS | " | " | |
| 903 | " | cyclohexyl-NH—CS | " | " | |
| 904 | " | (CH₃)₂CH—NH—CS | " | " | |

TABLE 1-continued (I")

| Example | A | B | $R^1$ | $R^6$ | Melting point [°C.] |
|---|---|---|---|---|---|
| 905 | " | $CH_3-(CH_2)_7-NH-CS$ | " | " | |
| 906 | " | $CH_3-O-CH_2-CH_2-NH-CS$ | " | " | |
| 907 | " | benzyl-NH-CS | " | " | |
| 908 | 3-$CF_3$-phenyl | $CH_3-CHCl-CO$ | $CH_3$ | $CH_3$ | |
| 909 | " | structure 1 | " | " | |
| 910 | " | 3-$NO_2$-4-Cl-benzoyl | " | " | |
| 911 | " | 4-tert-butylbenzoyl | " | " | |
| 912 | " | 2,4,6-trifluorobenzoyl | " | " | |
| 913 | " | 3,4-difluorobenzoyl | " | " | |
| 914 | " | 3-trifluoromethylbenzoyl | " | " | |
| 915 | " | 3,4-dichlorobenzoyl | " | " | |
| 916 | " | $C_2H_5-O-CO-(CH_2)_3-CO$ | " | " | |
| 917 | " | $CH_3-(CH_2)_7-CO$ | " | " | |
| 918 | " | phenyl-CH=CH-CO | " | " | |
| 919 | " | $Cl-(CH_2)_4-CO$ | " | " | |
| 920 | " | $Cl-(CH_2)_3-CO$ | " | " | |
| 921 | " | $CH_3-CH=CH-CO$ | " | " | |
| 922 | " | $CH_3-CH_2-CO$ | " | " | |
| 923 | " | $(CH_3)_2C=CH-CO$ | " | " | |
| 924 | " | $CH_2=CH-CO$ | " | " | |
| 925 | " | H-CO | " | " | |
| 926 | " | $ClH_2C-CO$ | " | " | |
| 927 | " | $CH_3-CO$ | " | " | |
| 928 | " | $(CH_3)_2CH-CO$ | " | " | |
| 929 | " | $CH_3-O-CH_2-CO$ | " | " | |
| 930 | " | $(CH_3)_2CF-CO$ | " | " | |
| 931 | " | $Cl_2HC-CO$ | " | " | |
| 932 | " | $CH_3-CHF-CO$ | " | " | |
| 933 | " | $CF_3-CO$ | " | " | |
| 934 | " | cyclopropyl-CO | " | " | |
| 935 | " | cyclobutyl-CO | " | " | |
| 936 | " | 2-furan-CO | " | " | |
| 937 | " | 2-thienyl-CO | " | " | |
| 938 | " | $CF_3-CH_2-CO$ | " | " | |
| 939 | " | $(CF_3)_2CH-CO$ | " | " | |
| 940 | " | tert-butyl-CO | " | " | |
| 941 | " | 3-cyanobenzoyl | " | " | |
| 942 | " | $(CH_3)_2CH-CH_2-CO$ | " | " | |
| 943 | " | tert-butyl-$CH_2$-CO | " | " | |
| 944 | " | $(C_2H_5)_2CH-CO$ | " | " | |
| 945 | " | $CH_3-CO-O-CH_2-CO$ | " | " | |
| 946 | " | $CH_3-O-CO-CH_2-CO$ | " | " | |
| 947 | " | benzyl-CO | " | " | |
| 948 | " | $CL-CH_2-(CH_3)_2C-CO$ | " | " | |
| 949 | " | 4-fluorobenzoyl | " | " | |
| 950 | " | 2-methoxybenzoyl | " | " | |
| 951 | " | 4-methoxybenzoyl | " | " | |
| 952 | " | 4-fluorobenzyl-CO | " | " | |
| 953 | " | 6-Cl-pyridine-3-CO | " | " | |
| 954 | " | pyridine-4-CO | " | " | |
| 955 | " | $CH_3-O-CO-(CH_2)_4-CO$ | " | " | |
| 956 | " | 2,4,6-trimethylbenzoyl | " | " | |
| 957 | " | 4-nitrobenzoyl | " | " | |
| 958 | " | 2,2-dichlorocyclopropyl-CO | " | " | |
| 959 | " | 2,2-difluorocyclopropyl-CO | " | " | |
| 960 | " | 2-methylcyclopropyl-CO | " | " | |
| 961 | " | 1-methylcyclopropyl-CO | " | " | |
| 962 | " | 3-($CF_3$-O)-benzoyl | " | " | |
| 963 | " | 2,5-Di$CF_3$-benzoyl | " | " | |
| 964 | " | 2-Br-5-methoxybenzoyl | " | " | |
| 965 | " | 1-$CH_3$-2,2-dichlorocyclopropyl-CO | " | " | |
| 966 | " | 2,2,3,3-tetramethyl-cyclopropyl-CO | " | " | |
| 967 | " | 2,3,4,5,6-pentafluorobenzoyl | " | " | |
| 968 | " | structure 2 | " | " | |
| 969 | " | $C_2H_5-O-CO-CO$ | " | " | |

TABLE 1-continued

Structure (I"): pyridine with R¹ at 4-position, A-O- at 2-position, and -CH₂-N(R⁶)-B at 6-position.

| Example | A | B | R¹ | R⁶ | Melting point [° C.] |
|---|---|---|---|---|---|
| 970 | " | CH₃—O—CO | " | " | |
| 971 | " | CH₃—CH₂—O—CO | " | " | |
| 972 | " | benzyl-O—CO | " | " | |
| 973 | " | C₄H₉—O—CO | " | " | |
| 974 | " | (CH₃)₂CH—CH₂—O—CO | " | " | |
| 975 | " | (CH₃)₂CH—O—CO | " | " | |
| 976 | " | (CH₃)₃C—O—CO | " | " | |
| 977 | " | C₃H₇—O—CO | " | " | |
| 978 | " | 4-NO₂-benzyl-O—CO | " | " | |
| 979 | " | CH₂=CH—CH₂—O—CO | " | " | |
| 980 | " | cyclopentyl-O—CO | " | " | |
| 981 | " | CF₃—CH₂—O—CO | " | " | |
| 982 | " | (CH₃)₂N—CO | " | " | |
| 983 | " | C₂H₅—NH—CO | " | " | |
| 984 | " | 2,4-difluorophenyl-NH—CO | " | " | |
| 985 | " | 3-fluorophenyl-NH—CO | " | " | |
| 986 | " | H₃C—NH—CO | " | " | |
| 987 | " | CH₂=CH—CH₂—NH—CO | " | " | |
| 988 | " | (CH₃)₂CH—NH—CO | " | " | |
| 989 | " | (CH₃)₃C—NH—CO | " | " | |
| 990 | " | (CH₃)₂CH—CH₂—NH—CO | " | " | |
| 991 | " | Cl—(CH₂)₃—NH—CO | " | " | |
| 992 | " | cyclohexyl-NH—CO | " | " | |
| 993 | " | C₂H₅—O—CO—CH₂—NH—CO | " | " | |
| 994 | " | benzyl-NH—CO | " | " | |
| 995 | " | C₂H₅—O—CO—(CH₂)₂—NH—CO | " | " | |
| 996 | " | 4-methylbenzyl-NH—CO | " | " | |
| 997 | " | [(CF₃)₂Cl]C—NH—CO | " | " | |
| 998 | " | CF₃—(CF₂)₅—NH—CO | " | " | |
| 999 | " | phenyl-N(CH₃)—CO | " | " | |
| 1000 | " | [(CH₃)₂CH—CH₂]₂N—CO | " | " | |
| 1001 | " | [(CH₃)₂CH]₂N—CO | " | " | |
| 1002 | " | N-pyrrolidinyl-CO | " | " | |
| 1003 | " | N-morpholinyl-CO | " | " | |
| 1004 | " | cyclopropyl-SO₂ | " | " | |
| 1005 | " | H₂C=CH—SO₂ | " | " | |
| 1006 | " | CF₃—CH₂—SO₂ | " | " | |
| 1007 | " | (CH₃)₂CH—SO₂ | " | " | |
| 1008 | " | C₂H₅—SO₂ | " | " | |
| 1009 | " | CF₃—SO₂ | " | " | |
| 1010 | " | CH₃—SO₂ | " | " | |
| 1011 | " | (CH₃)₂N—SO₂ | " | " | |
| 1012 | " | Cl₃C—SO₂ | " | " | |
| 1013 | " | CH₃—NH—SO₂ | " | " | |
| 1014 | " | 2,4,5-trichlorophenyl-SO₂ | " | " | |
| 1015 | " | 4-iodophenyl-SO₂ | " | " | |
| 1016 | " | benzyl-SO₂ | " | " | |
| 1017 | " | 4-nitrophenyl-SO₂ | " | " | |
| 1018 | " | 2-CF₃-phenyl-SO₂ | " | " | |
| 1019 | " | 4-tert-butyl-phenyl-SO₂ | " | " | |
| 1020 | " | Cl₂CH—SO₂ | " | " | |
| 1021 | " | C₃H₇—SO₂ | " | " | |
| 1022 | " | 4-chlorophenyl-SO₂ | " | " | |
| 1023 | " | 3-nitrophenyl-SO₂ | " | " | |
| 1024 | " | phenyl-SO₂ | " | " | |
| 1025 | " | CH₃—(CH₂)₃—NH—CS | " | " | |
| 1026 | " | C₂H₅—NH—CS | " | " | |
| 1027 | " | Phenyl-CH₂—CH₂—NH—CS | " | " | |
| 1028 | " | tert-butyl-NH—CS | " | " | |
| 1029 | " | 2-CF₃-phenyl-NH—CS | " | " | |
| 1030 | " | 4-CF₃-phenyl-NH—CS | " | " | |
| 1031 | " | phenyl-NH—CS | " | " | |
| 1032 | " | cyclohexyl-NH—CS | " | " | |
| 1033 | " | (CH₃)₂CH—NH—CS | " | " | |
| 1034 | " | CH₃—(CH₂)₇—NH—CS | " | " | |
| 1035 | " | CH₃—O—CH₂—CH₂—NH—CS | " | " | |

TABLE 1-continued $$\text{(I'')}$$

Structure: A–O–[pyridine with R¹ at 4-position, N in ring]–CH₂–N(R⁶)–B

| Example | A | B | R¹ | R⁶ | Melting point [°C] |
|---|---|---|---|---|---|
| 1036 | " | benzyl-NH—CS | " | " | |
| 1037 | 1-CH₃-3-CF₃-pyrazol-5-yl | CH₃—CHCl—CO | CN | H | |
| 1038 | 1-CH₃-3-CF₃-pyrazol-5-yl | structure 1 | " | " | |
| 1039 | 1-CH₃-3-CF₃-pyrazol-5-yl | 3-NO₂-4-Cl-benzoyl | " | " | |
| 1040 | 1-CH₃-3-CF₃-pyrazol-5-yl | 4-tert-butylbenzoyl | " | " | |
| 1041 | 1-CH₃-3-CF₃-pyrazol-5-yl | 2,4,6-trifluorobenzoyl | " | " | |
| 1042 | 1-CH₃-3-CF₃-pyrazol-5-yl | 3,4-difluorobenzoyl | " | " | |
| 1043 | 1-CH₃-3-CF₃-pyrazol-5-yl | 3-trifluoromethylbenzoyl | " | " | |
| 1044 | 1-CH₃-3-CF₃-pyrazol-5-yl | 3,4-dichlorobenzoyl | " | " | |
| 1045 | 1-CH₃-3-CF₃-pyrazol-5-yl | C₂H₅—O—CO—(CH₂)₃—CO | " | " | |
| 1046 | 1-CH₃-3-CF₃-pyrazol-5-yl | CH₃—(CH₂)₇—CO | " | " | |
| 1047 | 1-CH₃-3-CF₃-pyrazol-5-yl | phenyl-CH=CH—CO | " | " | |
| 1048 | 1-CH₃-3-CF₃-pyrazol-5-yl | Cl—(CH₂)₄—CO | " | " | |
| 1049 | 1-CH₃-3-CF₃-pyrazol-5-yl | Cl—(CH₂)₃—CO | " | " | |
| 1050 | 1-CH₃-3-CF₃-pyrazol-5-yl | CH₃—CH=CH—CO | " | " | |
| 1051 | 1-CH₃-3-CF₃-pyrazol-5-yl | CH₃—CH₂—CO | " | " | |
| 1052 | 1-CH₃-3-CF₃-pyrazol-5-yl | (CH₃)₂C=CH—CO | " | " | |
| 1053 | 1-CH₃-3-CF₃-pyrazol-5-yl | CH₂=CH—CO | " | " | |
| 1054 | 1-CH₃-3-CF₃-pyrazol-5-yl | H—CO | " | " | |
| 1055 | 1-CH₃-3-CF₃-pyrazol-5-yl | ClH₂C—CO | " | " | |
| 1056 | 1-CH₃-3-CF₃-pyrazol-5-yl | CH₃—CO | " | " | |
| 1057 | 1-CH₃-3-CF₃-pyrazol-5-yl | (CH₃)₂CH—CO | " | " | |
| 1058 | 1-CH₃-3-CF₃-pyrazol-5-yl | CH₃—O—CH₂—CO | " | " | |
| 1059 | 1-CH₃-3-CF₃-pyrazol-5-yl | (CH₃)₂CF—CO | " | " | |
| 1060 | 1-CH₃-3-CF₃-pyrazol-5-yl | Cl₂HC—CO | " | " | |
| 1061 | 1-CH₃-3-CF₃-pyrazol-5-yl | CH₃—CHF—CO | " | " | |
| 1062 | 1-CH₃-3-CF₃-pyrazol-5-yl | CF₃—CO | " | " | |
| 1063 | 1-CH₃-3-CF₃-pyrazol-5-yl | cyclopropyl-CO | " | " | |
| 1064 | 1-CH₃-3-CF₃-pyrazol-5-yl | cyclobutyl-CO | " | " | |
| 1065 | 1-CH₃-3-CF₃-pyrazol-5-yl | 2-furan-CO | " | " | |
| 1066 | 1-CH₃-3-CF₃-pyrazol-5-yl | 2-thienyl-CO | " | " | |
| 1067 | 1-CH₃-3-CF₃-pyrazol-5-yl | CF₃—CH₂—CO | " | " | |
| 1068 | 1-CH₃-3-CF₃-pyrazol-5-yl | (CF₃)₂CH—CO | " | " | |

TABLE 1-continued (I")

| Example | A | B | R¹ | R⁶ | Melting point [° C.] |
|---|---|---|---|---|---|
| 1069 | 1-CH₃-3-CF₃-pyrazol-5-yl | tert-butyl-CO | " | " | |
| 1070 | 1-CH₃-3-CF₃-pyrazol-5-yl | 3-cyanobenzoyl | " | " | |
| 1071 | 1-CH₃-3-CF₃-pyrazol-5-yl | (CH₃)₂CH—CH₂—CO | " | " | |
| 1072 | 1-CH₃-3-CF₃-pyrazol-5-yl | tert-butyl-CH₂—CO | " | " | |
| 1073 | 1-CH₃-3-CF₃-pyrazol-5-yl | (C₂H₅)₂CH—CO | " | " | |
| 1074 | 1-CH₃-3-CF₃-pyrazol-5-yl | CH₃—CO—O—CH₂—CO | " | " | |
| 1075 | 1-CH₃-3-CF₃-pyrazol-5-yl | CH₃—O—CO—CH₂—CO | " | " | |
| 1076 | 1-CH₃-3-CF₃-pyrazol-5-yl | benzyl-CO | " | " | |
| 1077 | 1-CH₃-3-CF₃-pyrazol-5-yl | CL—CH₂—(CH₃)₂C—CO | " | " | |
| 1078 | 1-CH₃-3-CF₃-pyrazol-5-yl | 4-fluorobenzoyl | " | " | |
| 1079 | 1-CH₃-3-CF₃-pyrazol-5-yl | 2-methoxybenzoyl | " | " | |
| 1080 | 1-CH₃-3-CF₃-pyrazol-5-yl | 4-methoxybenzoyl | " | " | |
| 1081 | 1-CH₃-3-CF₃-pyrazol-5-yl | 4-fluorobenzoyl-CO | " | " | |
| 1082 | 1-CH₃-3-CF₃-pyrazol-5-yl | 6-Cl-pyridine-3-CO | " | " | |
| 1083 | 1-CH₃-3-CF₃-pyrazol-5-yl | pyridine-4-CO | " | " | |
| 1084 | 1-CH₃-3-CF₃-pyrazol-5-yl | CH₃—O—CO—(CH₂)₄—CO | " | " | |
| 1085 | 1-CH₃-3-CF₃-pyrazol-5-yl | 2,4,6-trimethylbenzoyl | " | " | |
| 1086 | 1-CH₃-3-CF₃-pyrazol-5-yl | 4-nitrobenzoyl | " | " | |
| 1087 | 1-CH₃-3-CF₃-pyrazol-5-yl | 2,2-dichlorocyclopropyl-CO | " | " | |
| 1088 | 1-CH₃-3-CF₃-pyrazol-5-yl | 2,2-difluorocyclopropyl-CO | " | " | |
| 1089 | 1-CH₃-3-CF₃-pyrazol-5-yl | 2-methylcyclopropyl-CO | " | " | |
| 1090 | 1-CH₃-3-CF₃-pyrazol-5-yl | 1-methylcyclopropyl-CO | " | " | |
| 1091 | 1-CH₃-3-CF₃-pyrazol-5-yl | 3-(CF₃—O)-benzoyl | " | " | |
| 1092 | 1-CH₃-3-CF₃-pyrazol-5-yl | 2,5-DiCF₃-benzoyl | " | " | |
| 1093 | 1-CH₃-3-CF₃-pyrazol-5-yl | 2-Br-5-methoxybenzoyl | " | " | |
| 1094 | 1-CH₃-3-CF₃-pyrazol-5-yl | 1-CH₃-2,2-dichlorocyclopropyl-CO | " | " | |
| 1095 | 1-CH₃-3-CF₃-pyrazol-5-yl | 2,2,3,3-tetramethyl-cyclopropyl-CO | " | " | |
| 1096 | 1-CH₃-3-CF₃-pyrazol-5-yl | 2,3,4,5,6-pentafluorobenzoyl | " | " | |
| 1097 | 1-CH₃-3-CF₃-pyrazol-5-yl | structure 2 | " | " | |
| 1098 | 1-CH₃-3-CF₃-pyrazol-5-yl | C₂H₅—O—CO—CO | " | " | |
| 1099 | 1-CH₃-3-CF₃-pyrazol-5-yl | CH₃—O—CO | " | " | |
| 1100 | 1-CH₃-3-CF₃-pyrazol-5-yl | CH₃—CH₂—O—CO | " | " | |
| 1101 | 1-CH₃-3-CF₃-pyrazol-5-yl | benzyl-O—CO | " | " | |

TABLE 1-continued (I")

| Example | A | B | R$^1$ | R$^6$ | Melting point [° C.] |
|---|---|---|---|---|---|
| 1102 | 1-CH$_3$-3-CF$_3$-pyrazol-5-yl | C$_4$H$_9$—O—CO | " | " | |
| 1103 | 1-CH$_3$-3-CF$_3$-pyrazol-5-yl | (CH$_3$)$_2$CH—CH$_2$—O—CO | " | " | |
| 1104 | 1-CH$_3$-3-CF$_3$-pyrazol-5-yl | (CH$_3$)$_2$CH—O—CO | " | " | |
| 1105 | 1-CH$_3$-3-CF$_3$-pyrazol-5-yl | (CH$_3$)$_3$C—O—CO | " | " | |
| 1106 | 1-CH$_3$-3-CF$_3$-pyrazol-5-yl | C$_3$H$_7$—O—CO | " | " | |
| 1107 | 1-CH$_3$-3-CF$_3$-pyrazol-5-yl | 4-NO$_2$-benzyl-O—CO | " | " | |
| 1108 | 1-CH$_3$-3-CF$_3$-pyrazol-5-yl | CH$_2$=CH—CH$_2$—O—CO | " | " | |
| 1109 | 1-CH$_3$-3-CF$_3$-pyrazol-5-yl | cyclopentyl-O—CO | " | " | |
| 1110 | 1-CH$_3$-3-CF$_3$-pyrazol-5-yl | CF$_3$—CH$_2$—O—CO | " | " | |
| 1111 | 1-CH$_3$-3-CF$_3$-pyrazol-5-yl | (CH$_3$)$_2$N—CO | " | " | |
| 1112 | 1-CH$_3$-3-CF$_3$-pyrazol-5-yl | C$_2$H$_5$—NH—CO | " | " | |
| 1113 | 1-CH$_3$-3-CF$_3$-pyrazol-5-yl | 2,4-difluorophenyl-NH—CO | " | " | |
| 1114 | 1-CH$_3$-3-CF$_3$-pyrazol-5-yl | 3-fluorophenyl-NH—CO | " | " | |
| 1115 | 1-CH$_3$-3-CF$_3$-pyrazol-5-yl | H$_3$C—NH—CO | " | " | |
| 1116 | 1-CH$_3$-3-CF$_3$-pyrazol-5-yl | CH$_2$=CH—CH$_2$—NH—CO | " | " | |
| 1117 | 1-CH$_3$-3-CF$_3$-pyrazol-5-yl | (CH$_3$)$_2$CH—NH—CO | " | " | |
| 1118 | 1-CH$_3$-3-CF$_3$-pyrazol-5-yl | (CH$_3$)$_3$C—NH—CO | " | " | |
| 1119 | 1-CH$_3$-3-CF$_3$-pyrazol-5-yl | (CH$_3$)$_2$CH—CH$_2$—NH—CO | " | " | |
| 1120 | 1-CH$_3$-3-CF$_3$-pyrazol-5-yl | Cl—(CH$_2$)$_3$—NH—CO | " | " | |
| 1121 | 1-CH$_3$-3-CF$_3$-pyrazol-5-yl | cyclohexyl-NH—CO | " | " | |
| 1122 | 1-CH$_3$-3-CF$_3$-pyrazol-5-yl | C$_2$H$_5$—O—CO—CH$_2$—NH—CO | " | " | |
| 1123 | 1-CH$_3$-3-CF$_3$-pyrazol-5-yl | benzyl-NH—CO | " | " | |
| 1124 | 1-CH$_3$-3-CF$_3$-pyrazol-5-yl | C$_2$H$_5$—O—CO—(CH$_2$)$_2$—NH—CO | " | " | |
| 1125 | 1-CH$_3$-3-CF$_3$-pyrazol-5-yl | 4-methylbenzyl-NH—CO | " | " | |
| 1126 | 1-CH$_3$-3-CF$_3$-pyrazol-5-yl | [(CF$_3$)$_2$Cl]C—NH—CO | " | " | |
| 1127 | 1-CH$_3$-3-CF$_3$-pyrazol-5-yl | CF$_3$—(CF$_2$)$_6$—NH—CO | " | " | |
| 1128 | 1-CH$_3$-3-CF$_3$-pyrazol-5-yl | phenyl-N(CH$_3$)—CO | " | " | |
| 1129 | 1-CH$_3$-3-CF$_3$-pyrazol-5-yl | [(CH$_3$)$_2$CH—CH$_2$]$_2$N—CO | " | " | |
| 1130 | 1-CH$_3$-3-CF$_3$-pyrazol-5-yl | [(CH$_3$)$_2$CH]$_2$N—CO | " | " | |
| 1131 | 1-CH$_3$-3-CF$_3$-pyrazol-5-yl | N-pyrrolidinyl-CO | " | " | |
| 1132 | 1-CH$_3$-3-CF$_3$-pyrazol-5-yl | N-morpholinyl-CO | " | " | |
| 1133 | 1-CH$_3$-3-CF$_3$-pyrazol-5-yl | cyclopropyl-SO$_2$ | " | " | |
| 1134 | 1-CH$_3$-3-CF$_3$-pyrazol-5-yl | H$_2$C=CH—SO$_2$ | " | " | |

TABLE 1-continued

Structure (I''): A-O-[pyridine with R¹ at 4-position, N in ring]-CH₂-N(R⁶)-B

| Example | A | B | R¹ | R⁶ | Melting point [° C.] |
|---|---|---|---|---|---|
| 1135 | 1-CH₃-3-CF₃-pyrazol-5-yl | CF₃—CH₂—SO₂ | " | " | |
| 1136 | 1-CH₃-3-CF₃-pyrazol-5-yl | (CH₃)₂CH—SO₂ | " | " | |
| 1137 | 1-CH₃-3-CF₃-pyrazol-5-yl | C₂H₅—SO₂ | " | " | |
| 1138 | 1-CH₃-3-CF₃-pyrazol-5-yl | CF₃—SO₂ | " | " | |
| 1139 | 1-CH₃-3-CF₃-pyrazol-5-yl | CH₃—SO₂ | " | " | |
| 1140 | 1-CH₃-3-CF₃-pyrazol-5-yl | CF₃—SO₂ | " | CF₃—SO₂ | |
| 1141 | 1-CH₃-3-CF₃-pyrazol-5-yl | (CH₃)₂N—SO₂ | " | H | |
| 1142 | 1-CH₃-3-CF₃-pyrazol-5-yl | Cl₃C—SO₂ | " | " | |
| 1143 | 1-CH₃-3-CF₃-pyrazol-5-yl | CH₃—NH—SO₂ | " | " | |
| 1144 | 1-CH₃-3-CF₃-pyrazol-5-yl | 2,4,5-trichlorophenyl-SO₂ | " | " | |
| 1145 | 1-CH₃-3-CF₃-pyrazol-5-yl | 4-iodophenyl-SO₂ | " | " | |
| 1146 | 1-CH₃-3-CF₃-pyrazol-5-yl | benzyl-SO₂ | " | " | |
| 1147 | 1-CH₃-3-CF₃-pyrazol-5-yl | 4-nitrophenyl-SO₂ | " | " | |
| 1148 | 1-CH₃-3-CF₃-pyrazol-5-yl | 2-CF₃-phenyp-l-SO₂ | " | " | |
| 1149 | 1-CH₃-3-CF₃-pyrazol-5-yl | 4-tert-butyl-phenyl-SO₂ | " | " | |
| 1150 | 1-CH₃-3-CF₃-pyrazol-5-yl | Cl₂CH—SO₂ | " | " | |
| 1151 | 1-CH₃-3-CF₃-pyrazol-5-yl | C₃H₇—SO₂ | " | " | |
| 1152 | 1-CH₃-3-CF₃-pyrazol-5-yl | 4-chlorophenyl-SO₂ | " | " | |
| 1153 | 1-CH₃-3-CF₃-pyrazol-5-yl | 3-nitrophenyl-SO₂ | " | " | |
| 1154 | 1-CH₃-3-CF₃-pyrazol-5-yl | phenyl-SO₂ | " | " | |
| 1155 | 1-CH₃-3-CF₃-pyrazol-5-yl | CH₃—(CH₂)₃—NH—CS | " | " | |
| 1156 | 1-CH₃-3-CF₃-pyrazol-5-yl | C₂H₅—NH—CS | " | " | |
| 1157 | 1-CH₃-3-CF₃-pyrazol-5-ylo | Phenyl-CH₂—CH₂—NH—CS | " | " | |
| 1158 | 1-CH₃-3-CF₃-pyrazol-5-yl | tert-butyl-NH—CS | " | " | |
| 1159 | 1-CH₃-3-CF₃-pyrazol-5-yl | 2-CF₃-phenyl-NH—CS | " | " | |
| 1160 | 1-CH₃-3-CF₃-pyrazol-5-yl | 4-CF₃-phenyl-NH—CS | " | " | |
| 1161 | 1-CH₃-3-CF₃-pyrazol-5-yl | phenyl-NH—CS | " | " | |
| 1162 | 1-CH₃-3-CF₃-pyrazol-5-yl | cyclohexyl-NH—CS | " | " | |
| 1163 | 1-CH₃-3-CF₃-pyrazol-5-yl | (CH₃)₂CH—NH—CS | " | " | |
| 1164 | 1-CH₃-3-CF₃-pyrazol-5-yl | CH₃—(CH₂)₇—NH—CS | " | " | |
| 1165 | 1-CH₃-3-CF₃-pyrazol-5-yl | CH₃—O—CH₂—CH₂—NH—CS | " | " | |
| 1166 | 1-CH₃-3-CF₃-pyrazol-5-yl | benzyl-NH—CS | " | " | |
| 1167 | 1-CH₃-3-CF₃-pyrazol-5-yl | CH₃—CHCl—CO | CN | CH₃ | |

TABLE 1-continued $$\text{Structure (I''): A-O-[pyridine with R}^1\text{ at 4-position, N in ring]-CH}_2\text{-N(R}^6\text{)-B}$$

| Example | A | B | R$^1$ | R$^6$ | Melting point [° C.] |
|---|---|---|---|---|---|
| 1168 | 1-CH$_3$-3-CF$_3$-pyrazol-5-yl | structure 1 | " | " | |
| 1169 | 1-CH$_3$-3-CF$_3$-pyrazol-5-yl | 3-NO$_2$-4-Cl-benzoyl | " | " | |
| 1170 | 1-CH$_3$-3-CF$_3$-pyrazol-5-yl | 4-tert-butylbenzoyl | " | " | |
| 1171 | 1-CH$_3$-3-CF$_3$-pyrazol-5-yl | 2,4,6-trifluorobenzoyl | " | " | |
| 1172 | 1-CH$_3$-3-CF$_3$-pyrazol-5-yl | 3,4-difluorobenzoyl | " | " | |
| 1173 | 1-CH$_3$-3-CF$_3$-pyrazol-5-yl | 3-trifluoromethylbenzoyl | " | " | |
| 1174 | 1-CH$_3$-3-CF$_3$-pyrazol-5-yl | 3,4-dichlorobenzoyl | " | " | |
| 1175 | 1-CH$_3$-3-CF$_3$-pyrazol-5-yl | C$_2$H$_5$—O—CO—(CH$_2$)$_3$—CO | " | " | |
| 1176 | 1-CH$_3$-3-CF$_3$-pyrazol-5-yl | CH$_3$—(CH$_2$)$_7$—CO | " | " | |
| 1177 | 1-CH$_3$-3-CF$_3$-pyrazol-5-yl | phenyl-CH=CH—CO | " | " | |
| 1178 | 1-CH$_3$-3-CF$_3$-pyrazol-5-yl | Cl—(CH$_2$)$_4$—CO | " | " | |
| 1179 | 1-CH$_3$-3-CF$_3$-pyrazol-5-yl | Cl—(CH$_2$)$_3$—CO | " | " | |
| 1180 | 1-CH$_3$-3-CF$_3$-pyrazol-5-yl | CH$_3$—CH=CH—CO | " | " | |
| 1181 | 1-CH$_3$-3-CF$_3$-pyrazol-5-yl | CH$_3$—CH$_2$—CO | " | " | |
| 1182 | 1-CH$_3$-3-CF$_3$-pyrazol-5-yl | (CH$_3$)$_2$C=CH—CO | " | " | |
| 1183 | 1-CH$_3$-3-CF$_3$-pyrazol-5-yl | CH$_2$=CH—CO | " | " | |
| 1184 | 1-CH$_3$-3-CF$_3$-pyrazol-5-yl | H—CO | " | " | |
| 1185 | 1-CH$_3$-3-CF$_3$-pyrazol-5-yl | ClH$_2$C—CO | " | " | |
| 1186 | 1-CH$_3$-3-CF$_3$-pyrazol-5-yl | CH$_3$—CO | " | " | |
| 1187 | 1-CH$_3$-3-CF$_3$-pyrazol-5-yl | (CH$_3$)$_2$CH—CO | " | " | |
| 1188 | 1-CH$_3$-3-CF$_3$-pyrazol-5-yl | CH$_3$—O—CH$_2$—CO | " | " | |
| 1189 | 1-CH$_3$-3-CF$_3$-pyrazol-5-yl | (CH$_3$)$_2$CF—CO | " | " | |
| 1190 | 1-CH$_3$-3-CF$_3$-pyrazol-5-yl | Cl$_2$HC—CO | " | " | |
| 1191 | 1-CH$_3$-3-CF$_3$-pyrazol-5-yl | CH$_3$—CHF—CO | " | " | |
| 1192 | 1-CH$_3$-3-CF$_3$-pyrazol-5-yl | CF$_3$—CO | " | " | |
| 1193 | 1-CH$_3$-3-CF$_3$-pyrazol-5-yl | cyclopropyl-CO | " | " | |
| 1194 | 1-CH$_3$-3-CF$_3$-pyrazol-5-yl | cyclobutyl-CO | " | " | |
| 1195 | 1-CH$_3$-3-CF$_3$-pyrazol-5-yl | 2-furan-CO | " | " | |
| 1196 | 1-CH$_3$-3-CF$_3$-pyrazol-5-yl | 2-thienyl-CO | " | " | |
| 1197 | 1-CH$_3$-3-CF$_3$-pyrazol-5-yl | CF$_3$—CH$_2$—CO | " | " | |
| 1198 | 1-CH$_3$-3-CF$_3$-pyrazol-5-yl | (CF$_3$)$_2$CH—CO | " | " | |
| 1199 | 1-CH$_3$-3-CF$_3$-pyrazol-5-yl | tert-butyl-CO | " | " | |
| 1200 | 1-CH$_3$-3-CF$_3$-pyrazol-5-yl | 3-cyanobenzoyl | " | " | |

TABLE 1-continued

Structure (I''): A–O–[pyridine with R¹ at 4-position, N in ring]–CH₂–N(R⁶)–B

| Example | A | B | R¹ | R⁶ | Melting point [° C.] |
|---|---|---|---|---|---|
| 1201 | 1-CH₃-3-CF₃-pyrazol-5-yl | (CH₃)₂CH—CH₂—CO | " | " | |
| 1202 | 1-CH₃-3-CF₃-pyrazol-5-yl | tert-butyl-CH₂—CO | " | " | |
| 1203 | 1-CH₃-3-CF₃-pyrazol-5-yl | (C₂H₅)₂CH—CO | " | " | |
| 1204 | 1-CH₃-3-CF₃-pyrazol-5-yl | CH₃—CO—O—CH₂—CO | " | " | |
| 1205 | 1-CH₃-3-CF₃-pyrazol-5-yl | CH₃—O—CO—CH₂—CO | " | " | |
| 1206 | 1-CH₃-3-CF₃-pyrazol-5-yl | benzyl-CO | " | " | |
| 1207 | 1-CH₃-3-CF₃-pyrazol-5-yl | CL—CH₂—(CH₃)₂C—CO | " | " | |
| 1208 | 1-CH₃-3-CF₃-pyrazol-5-yl | 4-fluorobenzoyl | " | " | |
| 1209 | 1-CH₃-3-CF₃-pyrazol-5-yl | 2-methoxybenzoyl | " | " | |
| 1210 | 1-CH₃-3-CF₃-pyrazol-5-yl | 4-methoxybenzoyl | " | " | |
| 1211 | 1-CH₃-3-CF₃-pyrazol-5-yl | 4-fluorobenzyl-CO | " | " | |
| 1212 | 1-CH₃-3-CF₃-pyrazol-5-yl | 6-Cl-pyridine-3-CO | " | " | |
| 1213 | 1-CH₃-3-CF₃-pyrazol-5-yl | pyridine-4-CO | " | " | |
| 1214 | 1-CH₃-3-CF₃-pyrazol-5-yl | CH₃—O—CO—(CH₂)₄—CO | " | " | |
| 1215 | 1-CH₃-3-CF₃-pyrazol-5-yl | 2,4,6-trimethylbenzoyl | " | " | |
| 1216 | 1-CH₃-3-CF₃-pyrazol-5-yl | 4-nitrobenzoyl | " | " | |
| 1217 | 1-CH₃-3-CF₃-pyrazol-5-yl | 2,2-dichlorocyclopropyl-CO | " | " | |
| 1218 | 1-CH₃-3-CF₃-pyrazol-5-yl | 2,2-difluorocyclopropyl-CO | " | " | |
| 1219 | 1-CH₃-3-CF₃-pyrazol-5-yl | 2-methylcyclopropyl-CO | " | " | |
| 1220 | 1-CH₃-3-CF₃-pyrazol-5-yl | 1-methylcyclopropyl-CO | " | " | |
| 1221 | 1-CH₃-3-CF₃-pyrazol-5-yl | 3-(CF₃—O)-benzoyl | " | " | |
| 1222 | 1-CH₃-3-CF₃-pyrazol-5-yl | 2,5-DiCF₃-benzoyl | " | " | |
| 1223 | 1-CH₃-3-CF₃-pyrazol-5-yl | 2-Br-5-methoxybenzoyl | " | " | |
| 1224 | 1-CH₃-3-CF₃-pyrazol-5-yl | 1-CH₃-2,2-dichlorocyclopropyl-CO | " | " | |
| 1225 | 1-CH₃-3-CF₃-pyrazol-5-yl | 2,2,3,3-tetramethyl-cyclopropyl-CO | " | " | |
| 1226 | 1-CH₃-3-CF₃-pyrazol-5-yl | 2,3,4,5,6-pentafluorobenzoyl | " | " | |
| 1227 | 1-CH₃-3-CF₃-pyrazol-5-yl | structure 2 | " | " | |
| 1228 | 1-CH₃-3-CF₃-pyrazol-5-yl | C₂H₅—O—CO—CO | " | " | |
| 1229 | 1-CH₃-3-CF₃-pyrazol-5-yl | CH₃—O—CO | " | " | |
| 1230 | 1-CH₃-3-CF₃-pyrazol-5-yl | CH₃—CH₂—O—CO | " | " | |
| 1231 | 1-CH₃-3-CF₃-pyrazol-5-yl | benzyl-O—CO | " | " | |
| 1232 | 1-CH₃-3-CF₃-pyrazol-5-yl | C₄H₉—O—CO | " | " | |
| 1233 | 1-CH₃-3-CF₃-pyrazol-5-yl | (CH₃)₂CH—CH₂—O—CO | " | " | |

TABLE 1-continued (I")

| Example | A | B | R¹ | R⁶ | Melting point [° C.] |
|---|---|---|---|---|---|
| 1234 | 1-CH₃-3-CF₃-pyrazol-5-yl | (CH₃)₂CH—O—CO | " | " | |
| 1235 | 1-CH₃-3-CF₃-pyrazol-5-yl | (CH₃)₃C—O—CO | " | " | |
| 1236 | 1-CH₃-3-CF₃-pyrazol-5-yl | C₃H₇—O—CO | " | " | |
| 1237 | 1-CH₃-3-CF₃-pyrazol-5-yl | 4-NO₂-benzyl-O—CO | " | " | |
| 1238 | 1-CH₃-3-CF₃-pyrazol-5-yl | CH₂=CH—CH₂—O—CO | " | " | |
| 1239 | 1-CH₃-3-CF₃-pyrazol-5-yl | cyclopentyl-O—CO | " | " | |
| 1240 | 1-CH₃-3-CF₃-pyrazol-5-yl | CF₃—CH₂—O—CO | " | " | |
| 1241 | 1-CH₃-3-CF₃-pyrazol-5-yl | (CH₃)₂N—CO | " | " | |
| 1242 | 1-CH₃-3-CF₃-pyrazol-5-yl | C₂H₅—NH—CO | " | " | |
| 1243 | 1-CH₃-3-CF₃-pyrazol-5-yl | 2,4-difluorophenyl-NH—CO | " | " | |
| 1244 | 1-CH₃-3-CF₃-pyrazol-5-yl | 3-fluorophenyl-NH—CO | " | " | |
| 1245 | 1-CH₃-3-CF₃-pyrazol-5-yl | H₃C—NH—CO | " | " | |
| 1246 | 1-CH₃-3-CF₃-pyrazol-5-yl | CH₂=CH—CH₂—NH—CO | " | " | |
| 1247 | 1-CH₃-3-CF₃-pyrazol-5-yl | (CH₃)₂CH—NH—CO | " | " | |
| 1248 | 1-CH₃-3-CF₃-pyrazol-5-yl | (CH₃)₃C—NH—CO | " | " | |
| 1249 | 1-CH₃-3-CF₃-pyrazol-5-yl | (CH₃)₂CH—CH₂—NH—CO | " | " | |
| 1250 | 1-CH₃-3-CF₃-pyrazol-5-yl | Cl—(CH₂)₃—NH—CO | " | " | |
| 1251 | 1-CH₃-3-CF₃-pyrazol-5-yl | cyclohexyl-NH—CO | " | " | |
| 1252 | 1-CH₃-3-CF₃-pyrazol-5-yl | C₂H₅—O—CO—CH₂—NH—CO | " | " | |
| 1253 | 1-CH₃-3-CF₃-pyrazol-5-yl | benzyl-NH—CO | " | " | |
| 1254 | 1-CH₃-3-CF₃-pyrazol-5-yl | C₂H₅—O—CO—(CH₂)₂—NH—CO | " | " | |
| 1255 | 1-CH₃-3-CF₃-pyrazol-5-yl | 4-methylbenzyl-NH—CO | " | " | |
| 1256 | 1-CH₃-3-CF₃-pyrazol-5-yl | [(CF₃)₂Cl]C—NH—CO | " | " | |
| 1257 | 1-CH₃-3-CF₃-pyrazol-5-yl | CF₃—(CF₂)₅—NH—CO | " | " | |
| 1258 | 1-CH₃-3-CF₃-pyrazol-5-yl | phenyl-N(CH₃)—CO | " | " | |
| 1259 | 1-CH₃-3-CF₃-pyrazol-5-yl | [(CH₃)₂CH—CH₂]₂N—CO | " | " | |
| 1260 | 1-CH₃-3-CF₃-pyrazol-5-yl | [(CH₃)₂CH]₂N—CO | " | " | |
| 1261 | 1-CH₃-3-CF₃-pyrazol-5-yl | N-pyrrolidinyl-CO | " | " | |
| 1262 | 1-CH₃-3-CF₃-pyrazol-5-yl | N-morpholinyl-CO | " | " | |
| 1263 | 1-CH₃-3-CF₃-pyrazol-5-yl | cyclopropyl-SO₂ | " | " | |
| 1264 | 1-CH₃-3-CF₃-pyrazol-5-yl | H₂C=CH—SO₂ | " | " | |
| 1265 | 1-CH₃-3-CF₃-pyrazol-5-yl | CF₃—CH₂—SO₂ | " | " | |
| 1266 | 1-CH₃-3-CF₃-pyrazol-5-yl | (CH₃)₂CH—SO₂ | " | " | |

TABLE 1-continued

Structure (I"): A-O-[pyridine with R¹ at 4-position, N in ring]-CH₂-N(R⁶)-B

| Example | A | B | R¹ | R⁶ | Melting point [° C.] |
|---|---|---|---|---|---|
| 1267 | 1-CH₃-3-CF₃-pyrazol-5-yl | C₂H₅—SO₂ | " | " | |
| 1268 | 1-CH₃-3-CF₃-pyrazol-5-yl | CF₃—SO₂ | " | " | |
| 1269 | 1-CH₃-3-CF₃-pyrazol-5-yl | CH₃—SO₂ | " | " | |
| 1270 | 1-CH₃-3-CF₃-pyrazol-5-yl | (CH₃)₂N—SO₂ | " | " | |
| 1271 | 1-CH₃-3-CF₃-pyrazol-5-yl | Cl₃C—SO₂ | " | " | |
| 1272 | 1-CH₃-3-CF₃-pyrazol-5-yl | CH₃—NH—SO₂ | " | " | |
| 1273 | 1-CH₃-3-CF₃-pyrazol-5-yl | 2,4,56-trichlorophenyl-SO₂ | " | " | |
| 1274 | 1-CH₃-3-CF₃-pyrazol-5-yl | 4-iodophenyl-SO₂ | " | " | |
| 1275 | 1-CH₃-3-CF₃-pyrazol-5-yl | benzyl-SO₂ | " | " | |
| 1276 | 1-CH₃-3-CF₃-pyrazol-5-yl | 4-nitrophenyl-SO₂ | " | " | |
| 1277 | 1-CH₃-3-CF₃-pyrazol-5-yl | 2-CF₃-phenyl-SO₂ | " | " | |
| 1278 | 1-CH₃-3-CF₃-pyrazol-5-yl | 4-tert-butyl-phenyl-SO₂ | " | " | |
| 1279 | 1-CH₃-3-CF₃-pyrazol-5-yl | Cl₂CH—SO₂ | " | " | |
| 1280 | 1-CH₃-3-CF₃-pyrazol-5-yl | C₃H₇—SO₂ | " | " | |
| 1281 | 1-CH₃-3-CF₃-pyrazol-5-yl | 4-chlorophenyl-SO₂ | " | " | |
| 1282 | 1-CH₃-3-CF₃-pyrazol-5-yl | 3-nitrophenyl-SO₂ | " | " | |
| 1283 | 1-CH₃-3-CF₃-pyrazol-5-yl | phenyl-SO₂ | " | " | |
| 1284 | 1-CH₃-3-CF₃-pyrazol-5-yl | CH₃—(CH₂)₃—NH—CS | " | " | |
| 1285 | 1-CH₃-3-CF₃-pyrazol-5-yl | C₂H₅—NH—CS | " | " | |
| 1286 | 1-CH₃-3-CF₃-pyrazol-5-yl | Phenyl-CH₂—CH₂—NH—CS | " | " | |
| 1287 | 1-CH₃-3-CF₃-pyrazol-5-yl | tert-butyl-NH—CS | " | " | |
| 1288 | 1-CH₃-3-CF₃-pyrazol-5-yl | 2-CF₃-phenyl-NH—CS | " | " | |
| 1289 | 1-CH₃-3-CF₃-pyrazol-5-yl | 4-CF₃-phenyl-NH—CS | " | " | |
| 1290 | 1-CH₃-3-CF₃-pyrazol-5-yl | phenyl-NH—CS | " | " | |
| 1291 | 1-CH₃-3-CF₃-pyrazol-5-yl | cyclohexyl-NH—CS | " | " | |
| 1292 | 1-CH₃-3-CF₃-pyrazol-5-yl | (CH₃)₂CH—NH—CS | " | " | |
| 1293 | 1-CH₃-3-CF₃-pyrazol-5-yl | CH₃—(CH₂)₇—NH—CS | " | " | |
| 1294 | 1-CH₃-3-CF₃-pyrazol-5-yl | CH₃—O—CH₂—CH₂—NH—CS | " | " | |
| 1295 | 1-CH₃-3-CF₃-pyrazol-5-yl | benzyl-NH—CS | " | " | |
| 1296 | 3-CF₃-phenyl | CH₃—CHCl—CO | CN | H | |
| 1297 | " | structure 1 | " | " | |
| 1298 | " | 3-NO₂-4-Cl-benzoyl | " | " | |
| 1299 | " | 4-tert-butylbenzoyl | " | " | |
| 1300 | " | 2,4,6-trifluorobenzoyl | " | " | |
| 1301 | " | 3,4-difluorobenzoyl | " | " | |
| 1302 | " | 3-trifluoromethylbenzoyl | " | " | |
| 1303 | " | 3,4-dichlorobenzoyl | " | " | |

TABLE 1-continued (I")

| Example | A | B | R¹ | R⁶ | Melting point [°C.] |
|---|---|---|---|---|---|
| 1304 | " | $C_2H_5$—O—CO—$(CH_2)_3$—CO | " | " | |
| 1305 | " | $CH_3$—$(CH_2)_7$—CO | " | " | |
| 1306 | " | phenyl-CH=CH—CO | " | " | |
| 1307 | " | Cl—$(CH_2)_4$—CO | " | " | |
| 1308 | " | Cl—$(CH_2)_3$—CO | " | " | |
| 1309 | " | $CH_3$—CH=CH—CO | " | " | |
| 1310 | " | $CH_3$—$CH_2$—CO | " | " | |
| 1311 | " | $(CH_3)_2$C=CH—CO | " | " | |
| 1312 | " | $CH_2$=CH—CO | " | " | |
| 1313 | " | H—CO | " | " | |
| 1314 | " | $ClH_2C$—CO | " | " | |
| 1315 | " | $CH_3$—CO | " | " | |
| 1316 | " | $(CH_3)_2CH$—CO | " | " | |
| 1317 | " | $CH_3$—O—$CH_2$—CO | " | " | |
| 1318 | " | $(CH_3)_2CF$—CO | " | " | |
| 1319 | " | $Cl_2HC$—CO | " | " | |
| 1320 | " | $CH_3$—CHF—CO | " | " | |
| 1321 | " | $CF_3$—CO | " | " | |
| 1322 | " | cyclopropyl-CO | " | " | |
| 1323 | " | cyclobutyl-CO | " | " | |
| 1324 | " | 2-furan-CO | " | " | |
| 1325 | " | 2-thienyl-CO | " | " | |
| 1326 | " | $CF_3$—$CH_2$—CO | " | " | |
| 1327 | " | $(CF_3)_2CH$—CO | " | " | |
| 1328 | " | tert-butyl-CO | " | " | |
| 1329 | " | 3-cyanobenzoyl | " | " | |
| 1330 | " | $(CH_3)_2CH$—$CH_2$—CO | " | " | |
| 1331 | " | tert-butyl-$CH_2$—CO | " | " | |
| 1332 | " | $(C_2H_5)_2CH$—CO | " | " | |
| 1333 | " | $CH_3$—CO—O—$CH_2$—CO | " | " | |
| 1334 | " | $CH_3$—O—CO—$CH_2$—CO | " | " | |
| 1335 | " | benzyl-CO | " | " | |
| 1336 | " | CL—$CH_2$—$(CH_3)_2C$—CO | " | " | |
| 1337 | " | 4-fluorobenzoyl | " | " | |
| 1338 | " | 2-methoxybenzoyl | " | " | |
| 1339 | " | 4-methoxybenzoyl | " | " | |
| 1340 | " | 4-fluorobenzoyl-CO | " | " | |
| 1341 | " | 6-Cl-pyridine-3-CO | " | " | |
| 1342 | " | pyridine-4-CO | " | " | |
| 1434 | " | $CH_3$—O—CO—$(CH_2)_4$—CO | " | " | |
| 1344 | " | 2,4,6-trimethoxybenzoyl | " | " | |
| 1345 | " | 4-nitrobenzoyl | " | " | |
| 1346 | " | 2,2-dichlorocyclopropyl-CO | " | " | |
| 1347 | " | 2,2-difluorocyclopropyl-CO | " | " | |
| 1348 | " | 2-methylcyclopropyl-CO | " | " | |
| 1349 | " | 1-methylcyclopropyl-CO | " | " | |
| 1350 | " | 3-($CF_3$—O)-benzoyl | " | " | |
| 1351 | " | 2,5-Di$CF_3$-benzoyl | " | " | |
| 1352 | " | 2-Br-5-methoxybenzoyl | " | " | |
| 1353 | " | 1-$CH_3$-2,2-dichlorocyclopropyl-CO | " | " | |
| 1354 | " | 2,2,3,3-tetramethyl-cyclo-propyl-CO | " | " | |
| 1355 | " | 2,3,4,5,6-pentafluorobenzoyl | " | " | |
| 1356 | " | structure 2 | " | " | |
| 1357 | " | $C_2H_5$—O—CO | " | " | |
| 1358 | " | $CH_3$—O—CO | " | " | |
| 1359 | " | $CH_3$—$CH_2$—O—CO | " | " | |
| 1360 | " | benzyl-O—CO | " | " | |
| 1361 | " | $C_4H_9$—O—CO | " | " | |
| 1362 | " | $(CH_3)_2CH$—$CH_2$—O—CO | " | " | |
| 1363 | " | $(CH_3)_2CH$—O—CO | " | " | |
| 1364 | " | $(CH_3)_3C$—O—CO | " | " | |
| 1365 | " | $C_3H_7$—O—CO | " | " | |
| 1366 | " | 4-$NO_2$-benzyl-O—CO | " | " | |
| 1367 | " | $CH_2$=CH—$CH_2$—O—CO | " | " | |
| 1368 | " | cyclopentyl-O—CO | " | " | |

TABLE 1-continued (I″)

| Example | A | B | R¹ | R⁶ | Melting point [° C.] |
|---|---|---|---|---|---|
| 1369 | " | CF₃—CH₂—O—CO | " | " | |
| 1370 | " | (CH₃)₂N—CO | " | " | |
| 1371 | " | C₂H₅—NH—CO | " | " | |
| 1372 | " | 2,4-difluorophenyl-NH—CO | " | " | |
| 1373 | " | 3-fluorophenyl-NH—CO | " | " | |
| 1374 | " | H₃C—NH—CO | " | " | |
| 1375 | " | CH₂=CH—CH₂—NH—CO | " | " | |
| 1376 | " | (CH₃)₂CH—NH—CO | " | " | |
| 1377 | " | (CH₃)₃C—NH—CO | " | " | |
| 1378 | " | (CH₃)₂CH—CH₂—NH—CO | " | " | |
| 1379 | " | Cl—(CH₂)₃—NH—CO | " | " | |
| 1380 | " | cyclohexyl-NH—CO | " | " | |
| 1381 | " | C₂H₅—O—CO—CH₂—NH—CO | " | " | |
| 1382 | " | benzyl-NH—CO | " | " | |
| 1383 | " | C₂H₅—O—CO—(CH₂)₂—NH—CO | " | " | |
| 1384 | " | 4-methylbenzyl-NH—CO | " | " | |
| 1385 | " | [(CF₃)₂Cl]C—NH—CO | " | " | |
| 1386 | " | CF₃—(CF₂)₅—NH—CO | " | " | |
| 1387 | " | phenyl-N(CH₃)—CO | " | " | |
| 1388 | " | [(CH₃)₂CH—CH₂]₂N—CO | " | " | |
| 1389 | " | [(CH₃)₂CH]₂N—CO | " | " | |
| 1390 | " | N-pyrrolidinyl-CO | " | " | |
| 1391 | " | N-morpholinyl-CO | " | " | |
| 1392 | " | cyclopropyl-SO₂ | " | " | |
| 1393 | " | H₂C=CH—SO₂ | " | " | |
| 1394 | " | CF₃—CH₂—SO₂ | " | " | |
| 1395 | " | (CH₃)₂CH—SO₂ | " | " | |
| 1396 | " | C₂H₅—SO₂ | " | " | |
| 1397 | " | CF₃—SO₂ | " | " | |
| 1398 | " | CH₃—SO₂ | " | " | |
| 1399 | " | CF₃—SO₂ | " | CF₃—SO₂ | |
| 1400 | " | (CH₃)₂N—SO₂ | " | H | |
| 1401 | " | Cl₃C—SO₂ | " | " | |
| 1402 | " | CH₃—NH—SO₂ | " | " | |
| 1403 | " | 2,4,5-trichlorophenyl-SO₂ | " | " | |
| 1404 | " | 4-iodophenyl-SO₂ | " | " | |
| 1405 | " | benzyl-SO₂ | " | " | |
| 1406 | " | 4-nitrophenyl-SO₂ | " | " | |
| 1407 | " | 2-CF₃-phenyl-SO₂ | " | " | |
| 1408 | " | 4-tert-butyl-phenyl-SO₂ | " | " | |
| 1409 | " | Cl₂CH—SO₂ | " | " | |
| 1410 | " | C₃H₇—SO₂ | " | " | |
| 1411 | " | 4-chlorophenyl-SO₂ | " | " | |
| 1412 | " | 3-nitrophenyl-SO₂ | " | " | |
| 1413 | " | phenyl-SO₂ | " | " | |
| 1414 | " | CH₃—(CH₂)₃—NH—CS | " | " | |
| 1415 | " | C₂H₅—NH—CS | " | " | |
| 1416 | " | Phenyl-CH₂—CH₂—NH—CS | " | " | |
| 1417 | " | tert-butyl-NH—CS | " | " | |
| 1418 | " | 2-CF₃-phenyl-NH—CS | " | " | |
| 1419 | " | 4-CF₃-phenyl-NH—CS | " | " | |
| 1420 | " | phenyl-NH—CS | " | " | |
| 1421 | " | cyclohexyl-NH—CS | " | " | |
| 1422 | " | (CH₃)₂CH—NH—CS | " | " | |
| 1423 | " | CH₃—(CH₂)₇—NH—CS | " | " | |
| 1424 | " | CH₃—O—CH₂—CH₂—NH—CS | " | " | |
| 1425 | " | benzyl-NH—CS | " | " | |
| 1426 | " | CH₃—CHCl—CO | CN | CH₃ | |
| 1427 | " | structure 1 | " | " | |
| 1428 | " | 3-NO₂-4-Cl-benzoyl | " | " | |
| 1429 | " | 4-tert-butylbenzoyl | " | " | |
| 1430 | " | 2,4,6-trifluorobenzoyl | " | " | |
| 1431 | " | 3,4-difluorobenzoyl | " | " | |
| 1432 | " | 3-trifluoromethylbenzoyl | " | " | |
| 1433 | " | 3,4-dichlorobenzoyl | " | " | |
| 1434 | " | C₂H₅—O—CO—(CH₂)₃—CO | " | " | |

TABLE 1-continued (I″)

| Example | A | B | R¹ | R⁶ | Melting point [° C.] |
|---|---|---|---|---|---|
| 1435 | " | $CH_3-(CH_2)_7-CO$ | " | " | |
| 1436 | " | phenyl-CH=CH—CO | " | " | |
| 1437 | " | $Cl-(CH_2)_4-CO$ | " | " | |
| 1438 | " | $Cl-(CH_2)_3-CO$ | " | " | |
| 1439 | " | $CH_3-CH=CH-CO$ | " | " | |
| 1440 | " | $CH_3-CH_2-CO$ | " | " | |
| 1441 | " | $(CH_3)_2C=CH-CO$ | " | " | |
| 1442 | " | $CH_2=CH-CO$ | " | " | |
| 1443 | " | H—CO | " | " | |
| 1444 | " | $ClH_2C-CO$ | " | " | |
| 1445 | " | $CH_3-CO$ | " | " | |
| 1446 | " | $(CH_3)_2CH-CO$ | " | " | |
| 1447 | " | $CH_3-O-CH_2-CO$ | " | " | |
| 1448 | " | $(CH_3)_2CF-CO$ | " | " | |
| 1449 | " | $Cl_2HC-CO$ | " | " | |
| 1450 | " | $CH_3-CHF-CO$ | " | " | |
| 1451 | " | $CF_3-CO$ | " | " | |
| 1452 | " | cyclopropyl-CO | " | " | |
| 1453 | " | cyclobutyl-CO | " | " | |
| 1454 | " | 2-furan-CO | " | " | |
| 1455 | " | 2-thienyl-CO | " | " | |
| 1456 | " | $CF_3-CH_2-CO$ | " | " | |
| 1457 | " | $(CF_3)_2CH-CO$ | " | " | |
| 1458 | " | tert-butyl-CO | " | " | |
| 1459 | " | 3-cyanobenzoyl | " | " | |
| 1460 | " | $(CH_3)_2CH-CH_2-CO$ | " | " | |
| 1461 | " | tert-butyl-$CH_2$—CO | " | " | |
| 1462 | " | $(C_2H_5)_2CH-CO$ | " | " | |
| 1463 | " | $CH_3-CO-O-CH_2-CO$ | " | " | |
| 1464 | " | $CH_3-O-CO-CH_2-CO$ | " | " | |
| 1465 | " | benzyl-CO | " | " | |
| 1466 | " | $CL-CH_2-(CH_3)_2C-CO$ | " | " | |
| 1467 | " | 4-fluorobenzoyl | " | " | |
| 1468 | " | 2-methoxybenzoyl | " | " | |
| 1469 | " | 4-methoxybenzoyl | " | " | |
| 1470 | " | 4-fluorobenzyl-CO | " | " | |
| 1471 | " | 6-Cl-pyridine-3-CO | " | " | |
| 1472 | " | pyridine-4-CO | " | " | |
| 1473 | " | $CH_3-O-CO-(CH_2)_4-CO$ | " | " | |
| 1474 | " | 2,4,6-trimethoxybenzoyl | " | " | |
| 1475 | " | 4-nitrobenzoyl | " | " | |
| 1476 | " | 2,2-dichlorocyclopropyl-CO | " | " | |
| 1477 | " | 2,2-difluorocyclopropyl-CO | " | " | |
| 1478 | " | 2-methylcyclopropyl-CO | " | " | |
| 1479 | " | 1-methylcyclopropyl-CO | " | " | |
| 1480 | " | 3-($CF_3$—O)-benzoyl | " | " | |
| 1481 | " | 2,5-Di$CF_3$-benzoyl | " | " | |
| 1482 | " | 2-Br-5-methoxybenzoyl | " | " | |
| 1483 | " | 1-$CH_3$-2,2-dichlorocyclopropyl-CO | " | " | |
| 1484 | " | 2,2,3,3-tetramethyl-cyclopropyl-CO | " | " | |
| 1485 | " | 2,3,4,5,6-pentafluorobenzoyl | " | " | |
| 1486 | " | structure 2 | " | " | |
| 1487 | " | $C_2H_5-O-CO-CO$ | " | " | |
| 1488 | " | $CH_3-O-CO$ | " | " | |
| 1489 | " | $CH_3-CH_2-O-CO$ | " | " | |
| 1490 | " | benzyl-O—CO | " | " | |
| 1491 | " | $C_4H_9-O-CO$ | " | " | |
| 1492 | " | $(CH_3)_2CH-CH_2-O-CO$ | " | " | |
| 1493 | " | $(CH_3)_2CH-O-CO$ | " | " | |
| 1494 | " | $(CH_3)_3C-O-CO$ | " | " | |
| 1495 | " | $C_3H_7-O-CO$ | " | " | |
| 1496 | " | 4-$NO_2$-benzyl-O—CO | " | " | |
| 1497 | " | $CH_2=CH-CH_2-O-CO$ | " | " | |
| 1498 | " | cyclopentyl-O—CO | " | " | |
| 1499 | " | $CF_3-CH_2-O-CO$ | " | " | |

TABLE 1-continued (I'')

| Example | A | B | R$^1$ | R$^6$ | Melting point [° C.] |
|---|---|---|---|---|---|
| 1500 | " | (CH$_3$)$_2$N—CO | " | " | |
| 1501 | " | C$_2$H$_5$—NH—CO | " | " | |
| 1502 | " | 2,4-difluorophenyl-NH—CO | " | " | |
| 1503 | " | 3-fluorophenyl-NH—CO | " | " | |
| 1504 | " | H$_3$C—NH—CO | " | " | |
| 1505 | " | CH$_2$=CH—CH$_2$—NH—CO | " | " | |
| 1506 | " | (CH$_3$)$_2$CH—NH—CO | " | " | |
| 1507 | " | (CH$_3$)$_3$C—NH—CO | " | " | |
| 1508 | " | (CH$_3$)$_2$CH—CH$_2$—NH—CO | " | " | |
| 1509 | " | Cl—(CH$_3$)—NH—CO | " | " | |
| 1510 | " | cyclohexyl—NH—CO | " | " | |
| 1511 | " | C$_2$H$_5$—O—CO—CH$_2$—NH—CO | " | " | |
| 1512 | " | benzyl-NH—CO | " | " | |
| 1513 | " | C$_2$H$_5$—O—CO—(CH$_2$)$_2$—NH—CO | " | " | |
| 1514 | " | 4-methylbenzyl-NH—CO | " | " | |
| 1515 | " | [(CF$_3$)$_2$Cl]C—NH—CO | " | " | |
| 1516 | " | CF$_3$—(CF$_2$)$_5$—NH—CO | " | " | |
| 1517 | " | phenyl-N(CH$_3$)—CO | " | " | |
| 1518 | " | [(CH$_3$)$_2$CH—CH$_2$]$_2$N—CO | " | " | |
| 1519 | " | [(CH$_3$)$_2$CH]$_2$N—CO | " | " | |
| 1520 | " | N-pyrrolidinyl-CO | " | " | |
| 1521 | " | N-morpholinyl-CO | " | " | |
| 1522 | " | cyclopropyl-SO$_2$ | " | " | |
| 1523 | " | H$_2$C=CH—SO$_2$ | " | " | |
| 1524 | " | CF$_3$—CH$_2$—SO$_2$ | " | " | |
| 1525 | " | (CH$_3$)$_2$CH—SO$_2$ | " | " | |
| 1526 | " | C$_2$H$_5$—SO$_2$ | " | " | |
| 1527 | " | CF$_3$—SO$_2$ | " | " | |
| 1528 | " | CH$_3$—SO$_2$ | " | " | |
| 1529 | " | (CH$_3$)$_2$N—SO$_2$ | " | " | |
| 1530 | " | Cl$_3$C—SO$_2$ | " | " | |
| 1531 | " | CH$_3$—NH—SO$_2$ | " | " | |
| 1532 | " | 2,4,5-trichlorophenyl-SO$_2$ | " | " | |
| 1533 | " | 4-iodophenyl-SO$_2$ | " | " | |
| 1534 | " | benzyl-SO$_2$ | " | " | |
| 1535 | " | 4-nitrophenyl-SO$_2$ | " | " | |
| 1536 | " | 2-CF$_3$-phenyl-SO$_2$ | " | " | |
| 1537 | " | 4-tert-butyl-phenyl-SO$_2$ | " | " | |
| 1538 | " | Cl$_2$CH—SO$_2$ | " | " | |
| 1539 | " | C$_3$H$_7$—SO$_2$ | " | " | |
| 1540 | " | 4-chlorophenyl-SO$_2$ | " | " | |
| 1541 | " | 3-nitrophenyl-SO$_2$ | " | " | |
| 1542 | " | phenyl-SO$_2$ | " | " | |
| 1543 | " | CH$_3$—(CH$_2$)$_3$—NH—CS | " | " | |
| 1544 | " | C$_2$H$_5$—NH—CS | " | " | |
| 1545 | " | Phenyl-CH$_2$—CH$_2$—NH—CS | " | " | |
| 1546 | " | tert-butyl-NH—CS | " | " | |
| 1547 | " | 2-CF$_3$-phenyl-NH—CS | " | " | |
| 1548 | " | 4-CF$_3$-phenyl-NH—CS | " | " | |
| 1549 | " | phenyl-NH—CS | " | " | |
| 1550 | " | cyclohexyl-NH—CS | " | " | |
| 1551 | " | (CH$_3$)$_2$CH—NH—CS | " | " | |
| 1552 | " | CH$_3$—(CH$_2$)$_7$—NH—CS | " | " | |
| 1553 | " | CH$_3$—O—CH$_2$—CH$_2$—NH—CS | " | " | |
| 1554 | " | benzyl-NH—CS | " | " | |
| 1555 | 1-CH$_3$-3-CF$_3$-pyrazol-5-yl | CH$_3$—CHCl—CO | OCH$_3$ | H | |
| 1556 | 1-CH$_3$-3-CF$_3$-pyrazol-5-yl | structure 1 | " | " | |
| 1557 | 1-CH$_3$-3-CF$_3$-pyrazol-5-yl | 3-NO$_2$-4-Cl-benzoyl | " | " | |
| 1558 | 1-CH$_3$-3-CF$_3$-pyrazol-5-yl | 4-tert-butylbenzoyl | " | " | |
| 1559 | 1-CH$_3$-3-CF$_3$-pyrazol-5-yl | 2,4,6-trifluorobenzoyl | " | " | |

TABLE 1-continued (I″)

| Example | A | B | R¹ | R⁶ | Melting point [°C.] |
|---|---|---|---|---|---|
| 1560 | 1-CH₃-3-CF₃-pyrazol-5-yl | 3,4-difluorobenzoyl | " | " | |
| 1561 | 1-CH₃-3-CF₃-pyrazol-5-yl | 3-trifluoromethylbenzoyl | " | " | |
| 1562 | 1-CH₃-3-CF₃-pyrazol-5-yl | 3,4-dichlorobenzoyl | " | " | |
| 1563 | 1-CH₃-3-CF₃-pyrazol-5-yl | $C_2H_5-O-CO-(CH_2)_3-CO$ | " | " | |
| 1564 | 1-CH₃-3-CF₃-pyrazol-5-yl | $CH_3-(CH_2)_7-CO$ | " | " | |
| 1565 | 1-CH₃-3-CF₃-pyrazol-5-yl | phenyl-CH=CH—CO | " | " | |
| 1566 | 1-CH₃-3-CF₃-pyrazol-5-yl | $Cl-(CH_2)_4-CO$ | " | " | |
| 1567 | 1-CH₃-3-CF₃-pyrazol-5-yl | $Cl-(CH_2)_3-CO$ | " | " | |
| 1568 | 1-CH₃-3-CF₃-pyrazol-5-yl | CH₃—CH=CH—CO | " | " | |
| 1569 | 1-CH₃-3-CF₃-pyrazol-5-yl | CH₃—CH₂—CO | " | " | |
| 1570 | 1-CH₃-3-CF₃-pyrazol-5-yl | (CH₃)₂C=CH—CO | " | " | |
| 1571 | 1-CH₃-3-CF₃-pyrazol-5-yl | CH₂=CH—CO | " | " | |
| 1572 | 1-CH₃-3-CF₃-pyrazol-5-yl | H—CO | " | " | |
| 1573 | 1-CH₃-3-CF₃-pyrazol-5-yl | ClH₂C—CO | " | " | |
| 1574 | 1-CH₃-3-CF₃-pyrazol-5-yl | CH₃—CO | " | " | |
| 1575 | 1-CH₃-3-CF₃-pyrazol-5-yl | (CH₃)₂CH—CO | " | " | |
| 1576 | 1-CH₃-3-CF₃-pyrazol-5-yl | CH₃—O—CH₂—CO | " | " | |
| 1577 | 1-CH₃-3-CF₃-pyrazol-5-yl | (CH₃)₂CF—CO | " | " | |
| 1578 | 1-CH₃-3-CF₃-pyrazol-5-yl | Cl₂HC—CO | " | " | |
| 1579 | 1-CH₃-3-CF₃-pyrazol-5-yl | CH₃—CHF—CO | " | " | |
| 1580 | 1-CH₃-3-CF₃-pyrazol-5-yl | CF₃—CO | " | " | |
| 1581 | 1-CH₃-3-CF₃-pyrazol-5-yl | cyclopropyl-CO | " | " | |
| 1582 | 1-CH₃-3-CF₃-pyrazol-5-yl | cyclobutyl-CO | " | " | |
| 1583 | 1-CH₃-3-CF₃-pyrazol-5-yl | 2-furan-CO | " | " | |
| 1584 | 1-CH₃-3-CF₃-pyrazol-5-yl | 2-thienyl-CO | " | " | |
| 1585 | 1-CH₃-3-CF₃-pyrazol-5-yl | CF₃—CH₂—CO | " | " | |
| 1586 | 1-CH₃-3-CF₃-pyrazol-5-yl | (CF₃)₂CH—CO | " | " | |
| 1587 | 1-CH₃-3-CF₃-pyrazol-5-yl | tert-butyl-CO | " | " | |
| 1588 | 1-CH₃-3-CF₃-pyrazol-5-yl | 3-cyanobenzoyl | " | " | |
| 1589 | 1-CH₃-3-CF₃-pyrazol-5-yl | (CH₃)₂CH—CH₂—CO | " | " | |
| 1590 | 1-CH₃-3-CF₃-pyrazol-5-yl | tert-butyl-CH₂—CO | " | " | |
| 1591 | 1-CH₃-3-CF₃-pyrazol-5-yl | (C₂H₅)₂CH—CO | " | " | |
| 1592 | 1-CH₃-3-CF₃-pyrazol-5-yl | CH₃—CO—O—CH₂—CO | " | " | |

TABLE 1-continued

Structure (I''): A−O−[pyridine with R¹ at 4-position, N at 1-position]−CH₂−N(R⁶)−B

| Example | A | B | R¹ | R⁶ | Melting point [°C.] |
|---|---|---|---|---|---|
| 1593 | 1-CH₃-3-CF₃-pyrazol-5-yl | CH₃—O—CO—CH₂—CO | " | " | |
| 1594 | 1-CH₃-3-CF₃-pyrazol-5-yl | benzyl-CO | " | " | |
| 1595 | 1-CH₃-3-CF₃-pyrazol-5-yl | CL—CH₂—(CH₃)₂C—CO | " | " | |
| 1596 | 1-CH₃-3-CF₃-pyrazol-5-yl | 4-fluorobenzoyl | " | " | |
| 1597 | 1-CH₃-3-CF₃-pyrazol-5-yl | 2-methoxybenzoyl | " | " | |
| 1598 | 1-CH₃-3-CF₃-pyrazol-5-yl | 4-methoxybenzoyl | " | " | |
| 1599 | 1-CH₃-3-CF₃-pyrazol-5-yl | 4-fluorobenzyl-CO | " | " | |
| 1600 | 1-CH₃-3-CF₃-pyrazol-5-yl | 6-Cl-pyridine-3-CO | " | " | |
| 1601 | 1-CH₃-3-CF₃-pyrazol-5-yl | pyridine-4-CO | " | " | |
| 1602 | 1-CH₃-3-CF₃-pyrazol-5-ylo | CH₃—O—CO—(CH₂)₄—CO | " | " | |
| 1603 | 1-CH₃-3-CF₃-pyrazol-5-yl | 2,4,6-trimethylbenzoyl | " | " | |
| 1604 | 1-CH₃-3-CF₃-pyrazol-5-yl | 4-nitrobenzoyl | " | " | |
| 1605 | 1-CH₃-3-CF₃-pyrazol-5-yl | 2,2-dichlorocyclopropyl-CO | " | " | |
| 1606 | 1-CH₃-3-CF₃-pyrazol-5-yl | 2,2-difluorocyclopropyl-CO | " | " | |
| 1607 | 1-CH₃-3-CF₃-pyrazol-5-yl | 2-methylcyclopropyl-CO | " | " | |
| 1608 | 1-CH₃-3-CF₃-pyrazol-5-yl | 1-methylcyclopropyl-CO | " | " | |
| 1609 | 1-CH₃-3-CF₃-pyrazol-5-yl | 3-(CF₃—O)-benzoyl | " | " | |
| 1610 | 1-CH₃-3-CF₃-pyrazol-5-yl | 2,5-DiCF₃-benzoyl | " | " | |
| 1611 | 1-CH₃-3-CF₃-pyrazol-5-yl | 2-Br-5-methoxybenzoyl | " | " | |
| 1612 | 1-CH₃-3-CF₃-pyrazol-5-yl | 1-CH₃-2,2-dichlorocyclopropyl-CO | " | " | |
| 1613 | 1-CH₃-3-CF₃-pyrazol-5-yl | 2,2,3,3-tetramethyl-cyclopropyl-CO | " | " | |
| 1614 | 1-CH₃-3-CF₃-pyrazol-5-yl | 2,3,4,5,6-pentafluorobenzoyl | " | " | |
| 1615 | 1-CH₃-3-CF₃-pyrazol-5-yl | structure 2 | " | " | |
| 1616 | 1-CH₃-3-CF₃-pyrazol-5-yl | C₂H₅—O—CO—CO | " | " | |
| 1617 | 1-CH₃-3-CF₃-pyrazol-5-yl | CH₃—O—CO | " | " | |
| 1618 | 1-CH₃-3-CF₃-pyrazol-5-yl | CH₃—CH₂—O—CO | " | " | |
| 1619 | 1-CH₃-3-CF₃-pyrazol-5-yl | benzyl-O—CO | " | " | |
| 1620 | 1-CH₃-3-CF₃-pyrazol-5-yl | C₄H₉—O—CO | " | " | |
| 1621 | 1-CH₃-3-CF₃-pyrazol-5-yl | (CH₃)₂CH—CH₂—O—CO | " | " | |
| 1622 | 1-CH₃-3-CF₃-pyrazol-5-yl | (CH₃)₂CH—O—CO | " | " | |
| 1623 | 1-CH₃-3-CF₃-pyrazol-5-yl | (CH₃)₃C—O—CO | " | " | |
| 1624 | 1-CH₃-3-CF₃-pyrazol-5-yl | C₃H₇—O—CO | " | " | |
| 1625 | 1-CH₃-3-CF₃-pyrazol-5-yl | 4-NO₂-benzyl-O—CO | " | " | |

TABLE 1-continued (I")

| Example | A | B | R¹ | R⁶ | Melting point [° C.] |
|---|---|---|---|---|---|
| 1626 | 1-CH₃-3-CF₃-pyrazol-5-yl | CH₂=CH—CH₂—O—CO | " | " | |
| 1627 | 1-CH₃-3-CF₃-pyrazol-5-yl | cyclopentyl-O—CO | " | " | |
| 1628 | 1-CH₃-3-CF₃-pyrazol-5-yl | CF₃—CH₂—O—CO | " | " | |
| 1629 | 1-CH₃-3-CF₃-pyrazol-5-yl | (CH₃)₂N—CO | " | " | |
| 1630 | 1-CH₃-3-CF₃-pyrazol-5-yl | C₂H₅—NH—CO | " | " | |
| 1631 | 1-CH₃-3-CF₃-pyrazol-5-yl | 2,4-difluorophenyl-NH—CO | " | " | |
| 1632 | 1-CH₃-3-CF₃-pyrazol-5-yl | 3-fluorophenyl-NH—CO | " | " | |
| 1633 | 1-CH₃-3-CF₃-pyrazol-5-yl | H₃C—NH—CO | " | " | |
| 1634 | 1-CH₃-3-CF₃-pyrazol-5-yl | CH₂=CH—CH₂—NH—CO | " | " | |
| 1635 | 1-CH₃-3-CF₃-pyrazol-5-yl | (CH₃)₂CH—NH—CO | " | " | |
| 1636 | 1-CH₃-3-CF₃-pyrazol-5-yl | (CH₃)₂C—NH—CO | " | " | |
| 1637 | 1-CH₃-3-CF₃-pyrazol-5-yl | (CH₃)₂CH—CH₂—NH—CO | " | " | |
| 1638 | 1-CH₃-3-CF₃-pyrazol-5-yl | Cl—(CH₂)₃—NH—CO | " | " | |
| 1639 | 1-CH₃-3-CF₃-pyrazol-5-yl | cyclohexyl-NH—CO | " | " | |
| 1640 | 1-CH₃-3-CF₃-pyrazol-5-yl | C₂H₅—O—CO—CH₂—NH—CO | " | " | |
| 1641 | 1-CH₃-3-CF₃-pyrazol-5-yl | benzyl-NH—CO | " | " | |
| 1642 | 1-CH₃-3-CF₃-pyrazol-5-yl | C₂H₅—O—CO—(CH₂)₂—NH—CO | " | " | |
| 1643 | 1-CH₃-3-CF₃-pyrazol-5-yl | 4-methylbenzyl-NH—CO | " | " | |
| 1644 | 1-CH₃-3-CF₃-pyrazol-5-yl | [(CF₃)₂Cl]C—NH—CO | " | " | |
| 1645 | 1-CH₃-3-CF₃-pyrazol-5-yl | CF₃—(CF₂)₅—NH—CO | " | " | |
| 1646 | 1-CH₃-3-CF₃-pyrazol-5-yl | phenyl-N(CH₃)—CO | " | " | |
| 1647 | 1-CH₃-3-CF₃-pyrazol-5-yl | [(CH₃)₂CH—CH₂]₂N—CO | " | " | |
| 1648 | 1-CH₃-3-CF₃-pyrazol-5-yl | [(CH₃)₂CH]₂N—CO | " | " | |
| 1649 | 1-CH₃-3-CF₃-pyrazol-5-yl | N-pyrrolidinyl-CO | " | " | |
| 1650 | 1-CH₃-3-CF₃-pyrazol-5-yl | N-morpholinyl-CO | " | " | |
| 1651 | 1-CH₃-3-CF₃-pyrazol-5-yl | cyclopropyl-SO₂ | " | " | |
| 1652 | 1-CH₃-3-CF₃-pyrazol-5-yl | H₂C=CH—SO₂ | " | " | |
| 1653 | 1-CH₃-3-CF₃-pyrazol-5-yl | CF₃—CH₂—SO₂ | " | " | |
| 1654 | 1-CH₃-3-CF₃-pyrazol-5-yl | (CH₃)₂CH—SO₂ | " | " | |
| 1655 | 1-CH₃-3-CF₃-pyrazol-5-yl | C₂H₅—SO₂ | " | " | |
| 1656 | 1-CH₃-3-CF₃-pyrazol-5-yl | CF₃—SO₂ | " | " | |
| 1657 | 1-CH₃-3-CF₃-pyrazol-5-yl | CH₃—SO₂ | " | " | |
| 1658 | 1-CH₃-3-CF₃-pyrazol-5-yl | CF₃—SO₂ | " | CF₃—SO₂ | |

TABLE 1-continued (I")

| Example | A | B | R¹ | R⁶ | Melting point [° C.] |
|---|---|---|---|---|---|
| 1659 | 1-CH₃-3-CF₃-pyrazol-5-yl | (CH₃)₂N—SO₂ | " | H | |
| 1660 | 1-CH₃-3-CF₃-pyrazol-6-yl | Cl₃C—SO₂ | " | " | |
| 1661 | 1-CH₃-3-CF₃-pyrazol-5-yl | CH₃—NH—SO₂ | " | " | |
| 1662 | 1-CH₃-3-CF₃-pyrazol-5-yl | 2,4,5-trichlorophenyl-SO₂ | " | " | |
| 1663 | 1-CH₃-3-CF₃-pyrazol-5-yl | 4-iodophenyl-SO₂ | " | " | |
| 1664 | 1-CH₃-3-CF₃-pyrazol-5-yl | benzyl-SO₂ | " | " | |
| 1665 | 1-CH₃-3-CF₃-pyrazol-5-yl | 4-nitrophenyl-SO₂ | " | " | |
| 1666 | 1-CH₃-3-CF₃-pyrazol-5-yl | 2-CF₃-phenyl-SO₂ | " | " | |
| 1667 | 1-CH₃-3-CF₃-pyrazol-5-yl | 4-tert-butyl-phenyl-SO₂ | " | " | |
| 1668 | 1-CH₃-3-CF₃-pyrazol-5-yl | Cl₂CH—SO₂ | " | " | |
| 1669 | 1-CH₃-3-CF₃-pyrazol-5-yl | C₃H₇—SO₂ | " | " | |
| 1670 | 1-CH₃-3-CF₃-pyrazol-5-yl | 4-chlorophenyl-SO₂ | " | " | |
| 1671 | 1-CH₃-3-CF₃-pyrazol-5-yl | 3-nitrophenyl-SO₂ | " | " | |
| 1672 | 1-CH₃-3-CF₃-pyrazol-5-yl | phenyl-SO₂ | " | " | |
| 1673 | 1-CH₃-3-CF₃-pyrazol-5-yl | CH₃—(CH₂)₃—NH—CS | " | " | |
| 1674 | 1-CH₃-3-CF₃-pyrazol-5-yl | C₂H₅—NH—CS | " | " | |
| 1675 | 1-CH₃-3-CF₃-pyrazol-5-yl | Phenyl-CH₂—CH₂—NH—CS | " | " | |
| 1676 | 1-CH₃-3-CF₃-pyrazol-5-yl | tert-butyl-NH—CS | " | " | |
| 1677 | 1-CH₃-3-CF₃-pyrazol-5-yl | 2-CF₃-phenyl-NH—CS | " | " | |
| 1678 | 1-CH₃-3-CF₃-pyrazol-5-yl | 4-CF₃-phenyl-NH—CS | " | " | |
| 1679 | 1-CH₃-3-CF₃-pyrazol-5-yl | phenyl-NH—CS | " | " | |
| 1680 | 1-CH₃-3-CF₃-pyrazol-5-yl | cyclohexyl-NH—CS | " | " | |
| 1681 | 1-CH₃-3-CF₃-pyrazol-5-yl | (CH₃)₂CH—NH—CS | " | " | |
| 1682 | 1-CH₃-3-CF₃-pyrazol-5-yl | CH₃—(CH₂)₇—NH—CS | " | " | |
| 1683 | 1-CH₃-3-CF₃-pyrazol-5-yl | CH₃—O—CH₂—CH₂—NH—CS | " | " | |
| 1684 | 1-CH₃-3-CF₃-pyrazol-5-yl | benzyl-NH—CS | " | " | |
| 1685 | 1-CH₃-3-CF₃-pyrazol-5-yl | CH₃—CHCl—CO | OCH₃ | CH₃ | |
| 1686 | 1-CH₃-3-CF₃-pyrazol-5-yl | structure 1 | " | " | |
| 1687 | 1-CH₃-3-CF₃-pyrazol-5-yl | 3-NO₂-4-Cl-benzoyl | " | " | |
| 1688 | 1-CH₃-3-CF₃-pyrazol-5-yl | 4-tert-butylbenzoyl | " | " | |
| 1689 | 1-CH₃-3-CF₃-pyrazol-5-yl | 2,4,6-trifluorobenzoyl | " | " | |
| 1690 | 1-CH₃-3-CF₃-pyrazol-5-yl | 3,4-difluorobenzoyl | " | " | |
| 1691 | 1-CH₃-3-CF₃-pyrazol-5-yl | 3-trifluoromethylbenzoyl | " | " | |

TABLE 1-continued

Structure (I"): A-O-[pyridine with R¹ at 4-position, N at 1-position]-CH₂-N(R⁶)-B

| Example | A | B | R¹ | R⁶ | Melting point [° C.] |
|---|---|---|---|---|---|
| 1692 | 1-CH₃-3-CF₃-pyrazol-5-yl | 3,4-dichlorobenzoyl | " | " | |
| 1693 | 1-CH₃-3-CF₃-pyrazol-5-yl | C₂H₅—O—CO—(CH₂)₃—CO | " | " | |
| 1694 | 1-CH₃-3-CF₃-pyrazol-5-yl | CH₃—(CH₂)₇—CO | " | " | |
| 1695 | 1-CH₃-3-CF₃-pyrazol-5-yl | phenyl-CH=CH—CO | " | " | |
| 1696 | 1-CH₃-3-CF₃-pyrazol-5-yl | Cl—(CH₂)₄—CO | " | " | |
| 1697 | 1-CH₃-3-CF₃-pyrazol-5-yl | Cl—(CH₂)₃—CO | " | " | |
| 1698 | 1-CH₃-3-CF₃-pyrazol-5-yl | CH₃—CH=CH—CO | " | " | |
| 1699 | 1-CH₃-3-CF₃-pyrazol-5-yl | CH₃—CH₂—CO | " | " | |
| 1700 | 1-CH₃-3-CF₃-pyrazol-5-yl | (CH₃)₂C=CH—CO | " | " | |
| 1701 | 1-CH₃-3-CF₃-pyrazol-5-yl | CH₂=CH—CO | " | " | |
| 1702 | 1-CH₃-3-CF₃-pyrazol-5-yl | H—CO | " | " | |
| 1703 | 1-CH₃-3-CF₃-pyrazol-5-yl | ClH₂C—CO | " | " | |
| 1704 | 1-CH₃-3-CF₃-pyrazol-5-yl | CH₃—CO | " | " | |
| 1705 | 1-CH₃-3-CF₃-pyrazol-5-yl | (CH₃)₂CH—CO | " | " | |
| 1706 | 1-CH₃-3-CF₃-pyrazol-5-yl | CH₃—O—CH₂—CO | " | " | |
| 1707 | 1-CH₃-3-CF₃-pyrazol-5-yl | (CH₃)₂CF—CO | " | " | |
| 1708 | 1-CH₃-3-CF₃-pyrazol-5-yl | Cl₂HC—CO | " | " | |
| 1709 | 1-CH₃-3-CF₃-pyrazol-5-yl | CH₃CHF—CO | " | " | |
| 1710 | 1-CH₃-3-CF₃-pyrazol-5-yl | CF₃—CO | " | " | |
| 1711 | 1-CH₃-3-CF₃-pyrazol-5-yl | cyclopropyl-CO | " | " | |
| 1712 | 1-CH₃-3-CF₃-pyrazol-5-yl | cyclobutyl-CO | " | " | |
| 1713 | 1-CH₃-3-CF₃-pyrazol-5-yl | 2-furan-CO | " | " | |
| 1714 | 1-CH₃-3-CF₃-pyrazol-5-yl | 2-thienyl-CO | " | " | |
| 1715 | 1-CH₃-3-CF₃-pyrazol-5-yl | CF₃—CH₂—CO | " | " | |
| 1716 | 1-CH₃-3-CF₃-pyrazol-5-yl | (CF₃)₂CH—CO | " | " | |
| 1717 | 1-CH₃-3-CF₃-pyrazol-5-yl | tert-butyl-CO | " | " | |
| 1718 | 1-CH₃-3-CF₃-pyrazol-5-yl | 3-cyanobenzoyl | " | " | |
| 1719 | 1-CH₃-3-CF₃-pyrazol-5-yl | (CH₃)₂CH—CH₂—CO | " | " | |
| 1720 | 1-CH₃-3-CF₃-pyrazol-5-yl | tert-butyl-CH₂—CO | " | " | |
| 1721 | 1-CH₃-3-CF₃-pyrazol-5-yl | (C₂H₅)₂CH—CO | " | " | |
| 1722 | 1-CH₃-3-CF₃-pyrazol-5-yl | CH₃—CO—O—CH₂—CO | " | " | |
| 1723 | 1-CH₃-3-CF₃-pyrazol-5-yl | CH₃—O—CO—CH₂—CO | " | " | |
| 1724 | 1-CH₃-3-CF₃-pyrazol-5-yl | benzyl-CO | " | " | |

TABLE 1-continued

Structure (I"): A-O-[pyridine with R¹ at 4-position, N at 1-position]-CH₂-N(R⁶)-B

| Example | A | B | R¹ | R⁶ | Melting point [° C.] |
|---|---|---|---|---|---|
| 1725 | 1-CH₃-3-CF₃-pyrazol-5-yl | CL—CH₂—(CH₃)₂C—CO | " | " | |
| 1726 | 1-CH₃-3-CF₃-pyrazol-5-yl | 4-fluorobenzoyl | " | " | |
| 1727 | 1-CH₃-3-CF₃-pyrazol-5-yl | 2-methoxybenzoyl | " | " | |
| 1728 | 1-CH₃-3-CF₃-pyrazol-5-yl | 4-methoxybenzoyl | " | " | |
| 1729 | 1-CH₃-3-CF₃-pyrazol-5-yl | 4-fluorobenzoyl-CO | " | " | |
| 1730 | 1-CH₃-3-CF₃-pyrazol-5-yl | 6-Cl-pyridin-3-CO | " | " | |
| 1731 | 1-CH₃-3-CF₃-pyrazol-5-yl | pyridine-4-CO | " | " | |
| 1732 | 1-CH₃-3-CF₃-pyrazol-5-yl | CH₃—O—CO—(CH₂)₄—CO | " | " | |
| 1733 | 1-CH₃-3-CF₃-pyrazol-5-ylo | 2,4,6-trimethylbenzoyl | " | " | |
| 1734 | 1-CH₃-3-CF₃-pyrazol-5-yl | 4-nitrobenzoyl | " | " | |
| 1735 | 1-CH₃-3-CF₃-pyrazol-5-yl | 2,2-dichlorocyclopropyl-CO | " | " | |
| 1736 | 1-CH₃-3-CF₃-pyrazol-5-yl | 2,2-difluorocyclopropyl-CO | " | " | |
| 1737 | 1-CH₃-3-CF₃-pyrazol-5-yl | 2-methylcyclopropyl-CO | " | " | |
| 1738 | 1-CH₃-3-CF₃-pyrazol-5-yl | 1-methylcyclopropyl-CO | " | " | |
| 1739 | 1-CH₃-3-CF₃-pyrazol-5-yl | 3-(CF₃—O)-benzoyl | " | " | |
| 1740 | 1-CH₃-3-CF₃-pyrazol-5-yl | 2,5-DiCF₃-benzoyl | " | " | |
| 1741 | 1-CH₃-3-CF₃-pyrazol-5-yl | 2-Br-5-methoxybenzoyl | " | " | |
| 1742 | 1-CH₃-3-CF₃-pyrazol-5-yl | 1-CH₃-2,2-dichlorocyclopropyl-CO | " | " | |
| 1743 | 1-CH₃-3-CF₃-pyrazol-5-yl | 2,2,3,3-tetramethyl-cyclopropyl-CO | " | " | |
| 1744 | 1-CH₃-3-CF₃-pyrazol-5-yl | 2,3,4,5,6-pentafluorobenzoyl | " | " | |
| 1745 | 1-CH₃-3-CF₃-pyrazol-5-yl | structure 2 | " | " | |
| 1746 | 1-CH₃-3-CF₃-pyrazol-5-yl | C₂H₅—O—CO—CO | " | " | |
| 1747 | 1-CH₃-3-CF₃-pyrazol-5-yl | CH₃—O—CO | " | " | |
| 1748 | 1-CH₃-3-CF₃-pyrazol-5-yl | CH₃—CH₂—O—CO | " | " | |
| 1749 | 1-CH₃-3-CF₃-pyrazol-5-yl | benzyl-O—CO | " | " | |
| 1750 | 1-CH₃-3-CF₃-pyrazol-5-yl | C₄H₉—O—CO | " | " | |
| 1751 | 1-CH₃-3-CF₃-pyrazol-5-yl | (CH₃)₂CH—CH₂—O—CO | " | " | |
| 1752 | 1-CH₃-3-CF₃-pyrazol-5-yl | (CH₃)₂CH—O—CO | " | " | |
| 1753 | 1-CH₃-3-CF₃-pyrazol-5-yl | (CH₃)₃C—O—CO | " | " | |
| 1754 | 1-CH₃-3-CF₃-pyrazol-5-yl | C₃H₇—O—CO | " | " | |
| 1755 | 1-CH₃-3-CF₃-pyrazol-5-yl | 4-NO₂-benzyl-O—CO | " | " | |
| 1756 | 1-CH₃-3-CF₃-pyrazol-5-yl | CH₂=CH—CH₂—O—CO | " | " | |
| 1757 | 1-CH₃-3-CF₃-pyrazol-5-yl | cyclopentyl-O—CO | " | " | |

TABLE 1-continued (I″)

| Example | A | B | R¹ | R⁶ |
|---|---|---|---|---|
| 1758 | 1-CH₃-3-CF₃-pyrazol-5-ylo | CF₃—CH₂—O—CO | ″ | ″ |
| 1759 | 1-CH₃-3-CF₃-pyrazol-5-ylo | (CH₃)₂N—CO | ″ | ″ |
| 1760 | 1-CH₃-3-CF₃-pyrazol-5-yl | C₂H₅—NH—CO | ″ | ″ |
| 1761 | 1-CH₃-3-CF₃-pyrazol-5-yl | 2,4-difluorophenyl-NH—CO | ″ | ″ |
| 1762 | 1-CH₃-3-CF₃-pyrazol-5-yl | 3-fluorophenyl-NH—CO | ″ | ″ |
| 1763 | 1-CH₃-3-CF₃-pyrazol-5-yl | H₃C—NH—CO | ″ | ″ |
| 1764 | 1-CH₃-3-CF₃-pyrazol-5-yl | CH₂=CH—CH₂—NH—CO | ″ | ″ |
| 1765 | 1-CH₃-3-CF₃-pyrazol-5-yl | (CH₃)₂CH—NH—CO | ″ | ″ |
| 1766 | 1-CH₃-3-CF₃-pyrazol-5-yl | (CH₃)₃C—NH—CO | ″ | ″ |
| 1767 | 1-CH₃-3-CF₃-pyrazol-5-yl | (CH₃)₂CH—CH₂—NH—CO | ″ | ″ |
| 1768 | 1-CH₃-3-CF₃-pyrazol-5-yl | Cl—(CH₂)₃—NH—CO | ″ | ″ |
| 1769 | 1-CH₃-3-CF₃-pyrazol-5-yl | cyclohexyl-NH—CO | ″ | ″ |
| 1770 | 1-CH₃-3-CF₃-pyrazol-5-yl | C₂H₅—O—CO—CH₂—NH—CO | ″ | ″ |
| 1771 | 1-CH₃-3-CF₃-pyrazol-5-yl | benzyl-NH—CO | ″ | ″ |
| 1772 | 1-CH₃-3-CF₃-pyrazol-5-yl | C₂H₅—O—CO—(CH₂)₂—NH—CO | ″ | ″ |
| 1773 | 1-CH₃-3-CF₃-pyrazol-5-yl | 4-mehylbenzyl-NH—CO | ″ | ″ |
| 1774 | 1-CH₃-3-CF₃-pyrazol-5-yl | [(CF₃)₂Cl]C—NH—CO | ″ | ″ |
| 1775 | 1-CH₃-3-CF₃-pyrazol-5-yl | CF₃—(CF₂)₅—NH—CO | ″ | ″ |
| 1776 | 1-CH₃-3-CF₃-pyrazol-5-yl | phenyl-N(CH₃)—CO | ″ | ″ |
| 1777 | 1-CH₃-3-CF₃-pyrazol-5-yl | [(CH₃)₂CH—CH₂]₂N—CO | ″ | ″ |
| 1778 | 1-CH₃-3-CF₃-pyrazol-5-yl | [(CH₃)₂CH]₂N—CO | ″ | ″ |
| 1779 | 1-CH₃-3-CF₃-pyrazol-5-yl | N-pyrrolidinyl-CO | ″ | ″ |
| 1780 | 1-CH₃-3-CF₃-pyrazol-5-yl | N-morpholinyl-CO | ″ | ″ |
| 1781 | 1-CH₃-3-CF₃-pyrazol-5-yl | cyclopropyl-SO₂ | ″ | ″ |
| 1782 | 1-CH₃-3-CF₃-pyrazol-5-yl | H₂C=CH—SO₂ | ″ | ″ |
| 1783 | 1-CH₃-3-CF₃-pyrazol-5-yl | CF₃—CH₂—SO₂ | ″ | ″ |
| 1784 | 1-CH₃-3-CF₃-pyrazol-5-yl | (CH₃)₂CH—SO₂ | ″ | ″ |
| 1785 | 1-CH₃-3-CF₃-pyrazol-5-yl | C₂H₅—SO₂ | ″ | ″ |
| 1786 | 1-CH₃-3-CF₃-pyrazol-5-yl | CF₃—SO₂ | ″ | ″ |
| 1787 | 1-CH₃-3-CF₃-pyrazol-5-yl | CH₃—SO₂ | ″ | ″ |
| 1788 | 1-CH₃-3-CF₃-pyrazol-5-yl | (CH₃)₂N—SO₂ | ″ | ″ |
| 1789 | 1-CH₃-3-CF₃-pyrazol-5-yl | Cl₃C—SO₂ | ″ | ″ |
| 1790 | 1-CH₃-3-CF₃-pyrazol-5-yl | CH₃—NH—SO₂ | ″ | ″ |

TABLE 1-continued

Structure (I''): A-O-[pyridine with R¹ at 4-position, N at 1-position]-CH₂-N(R⁶)-B

| Example | A | B | R¹ | R⁶ | Melting point [° C.] |
|---|---|---|---|---|---|
| 1791 | 1-CH₃-3-CF₃-pyrazol-5-yl | 2,4,5-trichlorophenyl-SO₂ | " | " | |
| 1792 | 1-CH₃-3-CF₃-pyrazol-5-yl | 4-iodophenyl-SO₂ | " | " | |
| 1793 | 1-CH₃-3-CF₃-pyrazol-5-yl | benzyl-SO₂ | " | " | |
| 1794 | 1-CH₃-3-CF₃-pyrazol-5-yl | 4-nitrophenyl-SO₂ | " | " | |
| 1795 | 1-CH₃-3-CF₃-pyrazol-5-yl | 2-CF₃-phenyl-SO₂ | " | " | |
| 1796 | 1-CH₃-3-CF₃-pyrazol-5-yl | 4-tert-butyl-phenyl-SO₂ | " | " | |
| 1797 | 1-CH₃-3-CF₃-pyrazol-5-yl | Cl₂CH—SO₂ | " | " | |
| 1798 | 1-CH₃-3-CF₃-pyrazol-5-yl | C₃H₇—SO₂ | " | " | |
| 1799 | 1-CH₃-3-CF₃-pyrazol-5-yl | 4-chlorophenyl-SO₂ | " | " | |
| 1800 | 1-CH₃-3-CF₃-pyrazol-5-yl | 3-nitrophenyl-SO₂ | " | " | |
| 1801 | 1-CH₃-3-CF₃-pyrazol-5-yl | phenyl-SO₂ | " | " | |
| 1802 | 1-CH₃-3-CF₃-pyrazol-5-yl | CH₃—(CH₂)₃—NH—CS | " | " | |
| 1803 | 1-CH₃-3-CF₃-pyrazol-5-yl | C₂H₅—NH—CS | " | " | |
| 1804 | 1-CH₃-3-CF₃-pyrazol-5-yl | Phenyl-CH₂—CH₂—NH—CS | " | " | |
| 1805 | 1-CH₃-3-CF₃-pyrazol-5-yl | tert-butyl-NH—CS | " | " | |
| 1806 | 1-CH₃-3-CF₃-pyrazol-5-yl | 2-CF₃-phenyl-NH—CS | " | " | |
| 1807 | 1-CH₃-3-CF₃-pyrazol-5-yl | 4-CF₃-phenyl-NH—CS | " | " | |
| 1808 | 1-CH₃-3-CF₃-pyrazol-5-yl | phenyl-NH—CS | " | " | |
| 1809 | 1-CH₃-3-CF₃-pyrazol-5-yl | cyclohexyl-NH—CS | " | " | |
| 1810 | 1-CH₃-3-CF₃-pyrazol-5-yl | (CH₃)₂CH—NH—CS | " | " | |
| 1811 | 1-CH₃-3-CF₃-pyrazol-5-yl | CH₃—(CH₂)₇—NH—CS | " | " | |
| 1812 | 1-CH₃-3-CF₃-pyrazol-5-yl | CH₃—O—CH₂—CH₂—NH—CS | " | " | |
| 1813 | 1-CH₃-3-CF₃-pyrazol-5-yl | benzyl-NH—CS | " | " | |
| 1814 | 3-CF₃-phenyl | CH₃—CHCl—CO | OCH₃ | H | |
| 1815 | " | structure 1 | " | " | |
| 1816 | " | 3-NO₂-4-Cl-benzoyl | " | " | |
| 1817 | " | 4-tert-butylbenzoyl | " | " | |
| 1818 | " | 2,4,6-trifluorobenzoyl | " | " | |
| 1819 | " | 3,4-difluorobenzoyl | " | " | |
| 1820 | " | 3-trifluoromethylbenzoyl | " | " | |
| 1821 | " | 3,4-dichlorobenzoyl | " | " | |
| 1822 | " | C₂H₅—O—CO—(CH₂)₃—CO | " | " | |
| 1823 | " | CH₃—(CH₂)₇—CO | " | " | |
| 1824 | " | phenyl-CH=CH—CO | " | " | |
| 1825 | " | Cl—(CH₂)₄—CO | " | " | |
| 1826 | " | Cl—(CH₂)₃—CO | " | " | |
| 1827 | " | CH₃—CH=CH—CO | " | " | |
| 1828 | " | CH₃—CH₂—CO | " | " | |
| 1829 | " | (CH₃)₂C=CH—CO | " | " | |
| 1830 | " | CH₂=CH—CO | " | " | |
| 1831 | " | H—CO | " | " | |
| 1832 | " | ClH₂C—CO | " | " | |
| 1833 | " | CH₃—CO | " | " | |

TABLE 1-continued (I″)

| Example | A | B | R¹ | R⁶ |
|---|---|---|---|---|
| 1834 | " | (CH₃)₂CH—CO | " | " |
| 1835 | " | CH₃—O—CH₂—CO | " | " |
| 1836 | " | (CH₃)₂CF—CO | " | " |
| 1837 | " | Cl₂HC—CO | " | " |
| 1838 | " | CH₃—CHF—CO | " | " |
| 1839 | " | CF₃—CO | " | " |
| 1840 | " | cyclopropyl-CO | " | " |
| 1841 | " | cyclobutyl-CO | " | " |
| 1842 | " | 2-furan-CO | " | " |
| 1843 | " | 2-thienyl-CO | " | " |
| 1844 | " | CF₃—CH₂—CO | " | " |
| 1845 | " | (CF₃)₂CH—CO | " | " |
| 1846 | " | tert-butyl-CO | " | " |
| 1847 | " | 3-cyanobenzoyl | " | " |
| 1848 | " | (CH₃)₂CH—CH₂—CO | " | " |
| 1849 | " | tert-butyl-CH₂—CO | " | " |
| 1850 | " | (C₂H₅)₂CH—CO | " | " |
| 1851 | " | CH₃—CO—O—CH₂—CO | " | " |
| 1852 | " | CH₃—O—CO—CH₂—CO | " | " |
| 1853 | " | benzyl-CO | " | " |
| 1854 | " | CL—CH₂—(CH₃)₂C—CO | " | " |
| 1855 | " | 4-fluorobenzoyl | " | " |
| 1856 | " | 2-methoxybenzoyl | " | " |
| 1857 | " | 4-methoxybenzoyl | " | " |
| 1858 | " | 4-fluorobenzoyl-CO | " | " |
| 1859 | " | 6-Cl-pyridin-3-CO | " | " |
| 1860 | " | pyridine-4-CO | " | " |
| 1861 | " | CH₃—O—CO—(CH₂)₄—CO | " | " |
| 1862 | " | 2,4,6-trimethoxybenzoyl | " | " |
| 1863 | " | 4-nitrobenzoyl | " | " |
| 1864 | " | 2,3-dichlorocyclopropyl-CO | " | " |
| 1865 | " | 2,2-difluorocyclopropyl-CO | " | " |
| 1866 | " | 2-methylcyclopropyl-CO | " | " |
| 1867 | " | 1-methylcyclopropyl-CO | " | " |
| 1868 | " | 3-(CF₃—O)-benzoyl | " | " |
| 1869 | " | 2,5-DiCF₃-benzoyl | " | " |
| 1870 | " | 2-Br-5-methoxybenzoyl | " | " |
| 1871 | " | 1-CH₃-2,2-dichlorocyclopropyl-CO | " | " |
| 1872 | " | 2,2,3,3-tetramethyl-cyclo-propyl-CO | " | " |
| 1873 | " | 2,3,4,5,6-pentafluorobenzoyl | " | " |
| 1874 | " | structure 2 | " | " |
| 1875 | " | C₂H₅—O—CO—CO | " | " |
| 1876 | " | CH₃—O—CO | " | " |
| 1877 | " | CH₃—CH₂—O—CO | " | " |
| 1878 | " | benzyl-O—CO | " | " |
| 1879 | " | C₄H₉—O—CO | " | " |
| 1880 | " | (CH₃)₂CH—CH₂—O—CO | " | " |
| 1881 | " | (CH₃)₂CH—O—CO | " | " |
| 1882 | " | (CH₃)₂C—O—CO | " | " |
| 1883 | " | C₃H₇—O—CO | " | " |
| 1884 | " | 4-NO₂-benzyl-O—CO | " | " |
| 1885 | " | CH₂=CH—CH₂—O—CO | " | " |
| 1886 | " | cyclopentyl-O—CO | " | " |
| 1887 | " | CF₃—CH₂—O—CO | " | " |
| 1888 | " | (CH₃)₂N—CO | " | " |
| 1889 | " | C₂H₅—NH—CO | " | " |
| 1890 | " | 2,4-difluorophenyl-NH—CO | " | " |
| 1891 | " | 3-fluorophenyl-NH—CO | " | " |
| 1892 | " | H₃C—NH—CO | " | " |
| 1893 | " | CH₂=CH—CH₂—NH—CO | " | " |
| 1894 | " | (CH₃)₂CH—NH—CO | " | " |
| 1895 | " | (CH₃)₃C—NH—CO | " | " |
| 1896 | " | (CH₃)₂CH—CH₂—NH—CO | " | " |
| 1897 | " | Cl—(CH₂)₃—NH—CO | " | " |
| 1898 | " | cyclohexyl-NH—CO | " | " |

TABLE 1-continued

Structure (I''): pyridine with R¹ at 4-position, A-O- at 2-position, and -CH₂-N(R⁶)-B at 6-position.

| Example | A | B | R¹ | R⁶ | Melting point [° C.] |
|---|---|---|---|---|---|
| 1899 | " | C₂H₅—O—CO—CH₂—NH—CO | " | " | |
| 1900 | " | benzyl-NH—CO | " | " | |
| 1901 | " | C₂H₅—O—CO—(CH₂)₂—NH—CO | " | " | |
| 1902 | " | 4-methylbenzyl-NH—CO | " | " | |
| 1903 | " | [(CF₃)₂Cl]C—NH—CO | " | " | |
| 1904 | " | CF₃—(CF₂)₅—NH—CO | " | " | |
| 1905 | " | phenyl-N(CH₃)—CO | " | " | |
| 1906 | " | [(CH₃)₂CH—CH₂]₂N—CO | " | " | |
| 1907 | " | [(CH₃)₂CH]₂N—CO | " | " | |
| 1908 | " | N-pyrrolidinyl-CO | " | " | |
| 1909 | " | N-morpholinyl-CO | " | " | |
| 1910 | " | cyclopropyl-SO₂ | " | " | |
| 1911 | " | H₂C=CH—SO₂ | " | " | |
| 1912 | " | CF₃—CH₂—SO₂ | " | " | |
| 1913 | " | (CH₃)₂CH—SO₂ | " | " | |
| 1914 | " | C₂H₅—SO₂ | " | " | |
| 1915 | " | CF₃—SO₂ | " | " | |
| 1916 | " | CH₃—SO₂ | " | " | |
| 1917 | " | CF₃—SO₂ | " | CF₃—SO₂ | |
| 1918 | " | (CH₃)₂N—SO₂ | " | H | |
| 1919 | " | Cl₃C—SO₂ | " | " | |
| 1920 | " | CH₃—NH—SO₂ | " | " | |
| 1921 | " | 2,4,5-trichlorophenyl-SO₂ | " | " | |
| 1922 | " | 4-iodophenyl-SO₂ | " | " | |
| 1923 | " | benzyl-SO₂ | " | " | |
| 1924 | " | 4-nitrophenyl-SO₂ | " | " | |
| 1925 | " | 2-CF₃-phenyl-SO₂ | " | " | |
| 1926 | " | 4-tert-butyl-phenyl-SO₂ | " | " | |
| 1927 | " | Cl₂CH—SO₂ | " | " | |
| 1928 | " | C₃H₇—SO₂ | " | " | |
| 1929 | " | 4-chlorophenyl-SO₂ | " | " | |
| 1930 | " | 3-nitrophenyl-SO₂ | " | " | |
| 1931 | " | phenyl-SO₂ | " | " | |
| 1932 | " | CH₃—(CH₂)₃—NH—CS | " | " | |
| 1933 | " | C₂H₅—NH—CS | " | " | |
| 1934 | " | Phenyl-CH₂—CH₂—NH—CS | " | " | |
| 1935 | " | tert-butyl-NH—CS | " | " | |
| 1936 | " | 2-CF₃-phenyl-NH—CS | " | " | |
| 1937 | " | 4-CF₃-phenyl-NH—CS | " | " | |
| 1938 | " | phenyl-NH—CS | " | " | |
| 1939 | " | cyclohexyl-NH—CS | " | " | |
| 1940 | " | (CH₃)₂CH—NH—CS | " | " | |
| 1941 | " | CH₃—(CH₂)₇—NH—CS | " | " | |
| 1942 | " | CH₃—O—CH₂—CH₂—NH—CS | " | " | |
| 1943 | " | benzyl-NH—CS | " | " | |
| 1944 | " | CH₃—CHCl—CO | OCH₃ | CH₃ | |
| 1945 | " | structure 1 | " | " | |
| 1946 | " | 3-NO₂-4-Cl-benzoyl | " | " | |
| 1947 | " | 4-tert-butylbenzoyl | " | " | |
| 1948 | " | 2,4,6-trifluorobenzoyl | " | " | |
| 1949 | " | 3,4-difluorobenzoyl | " | " | |
| 1950 | " | 3-trifluoromethylbenzoyl | " | " | |
| 1951 | " | 3,4-dichlorobenzoyl | " | " | |
| 1952 | " | C₂H₅—O—CO—(CH₂)₃—CO | " | " | |
| 1953 | " | CH₃—(CH₂)₇—CO | " | " | |
| 1954 | " | phenyl-CH=CH—CO | " | " | |
| 1955 | " | Cl—(CH₂)₄—CO | " | " | |
| 1956 | " | Cl—(CH₂)₃—CO | " | " | |
| 1957 | " | CH₃—CH=CH—CO | " | " | |
| 1958 | " | CH₃—CH₂—CO | " | " | |
| 1959 | " | (CH₃)₂C=CH—CO | " | " | |
| 1960 | " | CH₂=CH—CO | " | " | |
| 1961 | " | H—CO | " | " | |
| 1962 | " | ClH₂C—CO | " | " | |
| 1963 | " | CH₃—CO | " | " | |
| 1964 | " | (CH₃)₂CH—CO | " | " | |

TABLE 1-continued (I″)

| Example | A | B | R$^1$ | R$^6$ | Melting point [° C.] |
|---|---|---|---|---|---|
| 1965 | " | CH$_3$—O—CH$_2$—CO | " | " | |
| 1966 | " | (CH$_3$)$_2$CF—CO | " | " | |
| 1967 | " | Cl$_2$HC—CO | " | " | |
| 1968 | " | CH$_3$—CHF—CO | " | " | |
| 1969 | " | CF$_3$—CO | " | " | |
| 1970 | " | cyclopropyl-CO | " | " | |
| 1971 | " | cyclobutyl-CO | " | " | |
| 1972 | " | 2-furan-CO | " | " | |
| 1973 | " | 2-thienyl-CO | " | " | |
| 1974 | " | CF$_3$—CH$_2$—CO | " | " | |
| 1975 | " | (CF$_3$)$_2$CH—CO | " | " | |
| 1976 | " | tert-butyl-CO | " | " | |
| 1977 | " | 3-cyanobenzoyl | " | " | |
| 1978 | " | (CH$_3$)$_2$CH—CH$_2$—CO | " | " | |
| 1979 | " | tert-butyl-CH$_2$—CO | " | " | |
| 1980 | " | (C$_2$H$_5$)$_2$CH—CO | " | " | |
| 1981 | " | CH$_3$—CO—O—CH$_2$—CO | " | " | |
| 1982 | " | CH$_3$—O—CO—CH$_2$—CO | " | " | |
| 1983 | " | benzyl-CO | " | " | |
| 1984 | " | CL—CH$_2$—(CH$_3$)$_2$C—CO | " | " | |
| 1985 | " | 4-fluorobenzoyl | " | " | |
| 1986 | " | 2-methoxybenzoyl | " | " | |
| 1987 | " | 4-methoxybenzoyl | " | " | |
| 1988 | " | 4-fluorobenzyl-CO | " | " | |
| 1989 | " | 6-Cl-pyridin-3-CO | " | " | |
| 1990 | " | pyridine-4-CO | " | " | |
| 1991 | " | CH$_3$—O—CO—(CH$_2$)$_4$—CO | " | " | |
| 1992 | " | 2,4,6-trimethylbenzoyl | " | " | |
| 1993 | " | 4-nitrobenzoyl | " | " | |
| 1994 | " | 2,2-difluorocyclopropyl-CO | " | " | |
| 1995 | " | 2,2-difluorocyclopropyl-CO | " | " | |
| 1996 | " | 2-methylcyclopropyl-CO | " | " | |
| 1997 | " | 1-methylcyclopropyl-CO | " | " | |
| 1998 | " | 3-(CF$_3$—O)-benzoyl | " | " | |
| 1999 | " | 2,5-DiCF$_3$-benzoyl | " | " | |
| 2000 | " | 2-Br-5-methoxybenzoyl | " | " | |
| 2001 | " | 1-CH$_3$-2,2-dichlorocyclopropyl-CO | " | " | |
| 2002 | " | 2,2,3,3-tetramethyl-cyclopropyl-CO | " | " | |
| 2003 | " | 2,3,4,5,6-pentafluorobenzoyl | " | " | |
| 2004 | " | structure 2 | " | " | |
| 2005 | " | C$_2$H$_5$—O—CO—CO | " | " | |
| 2006 | " | CH$_3$—O—CO | " | " | |
| 2007 | " | CH$_3$—CH$_2$—O—CO | " | " | |
| 2008 | " | benzyl-O—CO | " | " | |
| 2009 | " | C$_4$H$_9$—O—CO | " | " | |
| 2010 | " | (CH$_3$)$_2$CH—CH$_2$—O—CO | " | " | |
| 2011 | " | (CH$_3$)$_2$CH—O—CO | " | " | |
| 2012 | " | (CH$_3$)$_3$C—O—CO | " | " | |
| 2013 | " | C$_3$H$_7$—O—CO | " | " | |
| 2014 | " | 4-NO$_2$-benzyl-O—CO | " | " | |
| 2015 | " | CH$_2$=CH—CH$_2$—O—CO | " | " | |
| 2016 | " | cyclopentyl-O—CO | " | " | |
| 2017 | " | CF$_3$—CH$_2$—O—CO | " | " | |
| 2018 | " | (CH$_3$)$_2$N—CO | " | " | |
| 2019 | " | C$_2$H$_5$—NH—CO | " | " | |
| 2020 | " | 2,4-difluorophenyl-NH—CO | " | " | |
| 2021 | " | 3-fluorophenyl-NH—CO | " | " | |
| 2022 | " | H$_3$C—NH—CO | " | " | |
| 2023 | " | CH$_2$=CH—CH$_2$—NH—CO | " | " | |
| 2024 | " | (CH$_3$)$_2$CH—NH—CO | " | " | |
| 2025 | " | (CH$_3$)$_2$C—NH—CO | " | " | |
| 2026 | " | (CH$_3$)$_2$CH—CH$_2$—NH—CO | " | " | |
| 2027 | " | Cl—(CH$_2$)$_3$—NH—CO | " | " | |
| 2028 | " | cyclohexyl-NH—CO | " | " | |
| 2029 | " | C$_2$H$_5$—O—CO—CH$_2$—NH—CO | " | " | |

TABLE 1-continued (I'')

| Example | A | B | R¹ | R⁶ | Melting point [° C.] |
|---|---|---|---|---|---|
| 2030 | " | benzyl-NH—CO | " | " | |
| 2031 | " | $C_2H_5$—O—CO—$(CH_2)_2$—NH—CO | " | " | |
| 2032 | " | 4-methylbenzyl-NH—CO | " | " | |
| 2033 | " | [$(CF_3)_2Cl$]C—NH—CO | " | " | |
| 2034 | " | $CF_3$—$(CF_2)_5$—NH—CO | " | " | |
| 2035 | " | phenyl-N($CH_3$)—CO | " | " | |
| 2036 | " | [$(CH_3)_2CH$—$CH_2$]$_2$N—CO | " | " | |
| 2037 | " | [$(CH_3)_2CH$]$_2$N—CO | " | " | |
| 2038 | " | N-pyrrolidinyl-CO | " | " | |
| 2039 | " | N-morpholinyl-CO | " | " | |
| 2040 | " | cyclopropyl-$SO_2$ | " | " | |
| 2041 | " | $H_2C$=CH—$SO_2$ | " | " | |
| 2042 | " | $CF_3$—$CH_2$—$SO_2$ | " | " | |
| 2043 | " | $(CH_3)_2CH$—$SO_2$ | " | " | |
| 2044 | " | $C_2H_5$—$SO_2$ | " | " | |
| 2045 | " | $CF_3$—$SO_2$ | " | " | |
| 2046 | " | $CH_3$—$SO_2$ | " | " | |
| 2047 | " | $(CH_3)_2N$—$SO_2$ | " | " | |
| 2048 | " | $Cl_3C$—$SO_2$ | " | " | |
| 2049 | " | $CH_3$—NH—$SO_2$ | " | " | |
| 2050 | " | 2,4,5-trichlorophenyl-$SO_2$ | " | " | |
| 2051 | " | 4-iodophenyl-$SO_2$ | " | " | |
| 2052 | " | benzyl-$SO_2$ | " | " | |
| 2053 | " | 4-nitrophenyl-$SO_2$ | " | " | |
| 2054 | " | 2-$CF_3$-phenyl-$SO_2$ | " | " | |
| 2055 | " | 4-tert-butyl-phenyl-$SO_2$ | " | " | |
| 2056 | " | $Cl_2CH$—$SO_2$ | " | " | |
| 2057 | " | $C_3H_7$—$SO_2$ | " | " | |
| 2058 | " | 4-chlorophenyl-$SO_2$ | " | " | |
| 2059 | " | 3-nitrophenyl-$SO_2$ | " | " | |
| 2060 | " | phenyl-$SO_2$ | " | " | |
| 2061 | " | $CH_3$—$(CH_2)_3$—NH—CS | " | " | |
| 2062 | " | $C_2H_5$—NH—CS | " | " | |
| 2063 | " | Phenyl-$CH_2$—$CH_2$—NH—CS | " | " | |
| 2064 | " | tert-butyl-NH—CS | " | " | |
| 2065 | " | 2-$CF_3$-phenyl-NH—CS | " | " | |
| 2066 | " | 4-$CF_3$-phenyl-NH—CS | " | " | |
| 2067 | " | phenyl-NH—CS | " | " | |
| 2068 | " | cyclohexyl-NH—CS | " | " | |
| 2069 | " | $(CH_3)_2CH$—NH—CS | " | " | |
| 2070 | " | $CH_3$—$(CH_2)_7$—NH—CS | " | " | |
| 2071 | " | $CH_3$—O—$CH_2$—$CH_2$—NH—CS | " | " | |
| 2072 | " | benzyl-NH—CS | " | " | |

TABLE 2

(I''')

| Example | A | B | R¹ | R² | R⁶ | Melting point [° C.] |
|---|---|---|---|---|---|---|
| 2073 | 1-$CH_3$-3-$CF_3$-pyrazol-5-yl | $CH_3$—CHCl—CO | H | $CH_3$ | H | |
| 2074 | " | structure 1 | " | $CH_3$ | " | |
| 2075 | " | 3-$NO_2$-4-Cl-benzoyl | " | $CH_3$ | " | |
| 2076 | " | 4-tert-butylbenzoyl | " | $CH_3$ | " | |

TABLE 2-continued (I''')

![Structure of formula I''']

| Example | A | B | R¹ | R² | R⁶ | Melting point [° C.] |
|---------|---|---|----|----|----|---------------------|
| 2077 | " | 2,4,6-trifluorobenzoyl | " | $CH_3$ | " | |
| 2078 | " | 3,4-difluorobenzoyl | " | $CH_3$ | " | |
| 2079 | " | 3-trifluoromethylbenzoyl | " | $CH_3$ | " | |
| 2080 | " | 3,4-dichlorobenzoyl | " | $CH_3$ | " | |
| 2081 | " | $C_2H_5$—O—CO—$(CH_2)_3$—CO | " | $CH_3$ | " | |
| 2082 | " | $CH_3$—$(CH_2)_7$—CO | " | $CH_3$ | " | |
| 2083 | " | Phenyl-CH═CH—CO | " | $CH_3$ | " | |
| 2084 | " | Cl—$(CH_2)_4$—CO | " | $CH_3$ | " | |
| 2085 | " | Cl—$(CH_2)_3$—CO | " | $CH_3$ | " | |
| 2086 | " | $CH_3$—$CH_2$—CO | " | $CH_3$ | " | |
| 2087 | " | $(CH_3)_2C$═CH—CO | " | $CH_3$ | " | |
| 2088 | " | $CH_2$═CH—CO | " | $CH_3$ | " | |
| 2089 | " | $ClH_2C$—CO | " | $CH_3$ | " | |
| 2090 | " | $CH_3$—CO | " | $CH_3$ | " | |
| 2091 | " | $(CH_3)_2CH$—CO | " | $CH_3$ | " | 117.5 |
| 2092 | " | $CH_3$—O—$CH_2$—CO | " | $CH_3$ | " | |
| 2093 | " | $(CH_3)_2CF$—CO | " | $CH_3$ | " | |
| 2094 | " | $Cl_2HC$—CO | " | $CH_3$ | " | |
| 2095 | " | $CH_3$—CHF—CO | " | $CH_3$ | " | |
| 2096 | " | $CF_3$—CO | " | $CH_3$ | " | |

Elucidations relating to tables 1 and 2:

structure 1:

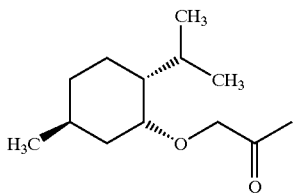

structure 2:

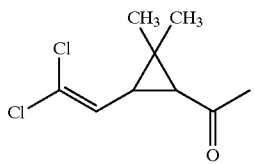

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of ethoxylated nonylphenol as emulsifier.

e) Water-dispersible granules are obtained by mixing

| 75 parts by weight | of a compound of the formula (I), |
| 10 " | of calcium lignosulfonate, |
| 5 " | of sodium lauryl sulfate, |
| 3 " | of polyvinyl alcohol and |
| 7 " | of kaolin, | grinding the mixture in a pinned-disk mill and granulating the powder in a fluidized bed by spraying on water as granulation liquid.

f) Water-dispersible granules are also obtained by homogenizing and precomminuting, on a colloid mill,

| 25 parts by weight | of a compound of the formula (I), |
| 5 " | of sodium 2,2'-dinaphthylmethane-6,6'-disulfonate, |
| 2 " | of sodium oleoylmethyltaurinate, |
| 1 part by weight | of polyvinyl alcohol, |
| 17 parts by weight | of calcium carbonate and |
| 50 " | of water, | subsequently grinding the mixture in a bead mill and atomizing and drying the resulting suspension in a spray tower by means of a single-substance nozzle.

C. Biological Examples

1. Pre-emergence Effect on Weeds

Seeds or rhizome pieces of mono- and dicotyledonous weed plants were placed in sandy loam soil in plastic pots and covered with soil. The compounds according to the invention, formulated in the form of wettable powders or emulsion concentrates, were then applied to the soil cover in the form of aqueous suspensions or emulsions at an application rate of 600 to 800 l of water/ha (converted), in various dosages. After the treatment, the pots were placed in a greenhouse and kept under good growth conditions for the weeds. After the test plants had emerged, the damage to the plants or the negative effect on the emergence was visually scored after a test period of 3 to 4 weeks by comparison with untreated controls. As shown by the test results, the compounds according to the invention have good herbicidal pre-emergence activity against a broad spectrum of week grasses and broad-leaved weeds. For example, the compounds of examples Nos. 4, 5, 10, 18, 19, 20, 21, 22, 24, 25, 26, 27, 28, 29, 30, 31, 34, 66, 78, 79, 134, 147, 148, 149, 150, 153, 155, 157, 159, 261, 275, 276, 279, 281, 283, 284, 285, 286, 287, 533, 539, 541, 542, 543, 544, 545, 546, 549 and other compounds from table 1 have very good herbicidal activity pre-emergence against weed plants such as *Sinapis alba, Chrysanthemum segetum, Avena sativa, Stellaria media, Echinochloa crus-galli, Lolium multiflorum*, Setaria spp., *Abutilon theophrasti, Amaranthus retroflexus* and *Panicum maliaceum* at an application rate of 1 kg or less of active substance per hectare.

2. Post-emergence Effect on Weeds

Seeds or rhizome pieces of mono- and dicotyledonous weeds were placed in sandy loam soil in plastic pots, covered with soil and grown in a greenhouse under good growth conditions. Three weeks after sowing, the test plants were treated at the three-leaf stage. The compounds according to the invention, formulated as wettable powders or emulsion concentrates, were sprayed, at various dosages, onto the green parts of the plants at an application rate of 600 to 800 l of water/ha (converted). After the test plants had remained in the greenhouse for about 3 to 4 weeks under optimum growth conditions, the effect of the preparations was scored visually by comparison with untreated controls. The agents according to the invention also have good herbicidal activity post-emergence against a broad spectrum of economically important weed grasses and broad-leaved weeds. For example, the compounds of Example Nos. 4, 5, 10, 18, 19, 20, 21, 22, 24, 25, 26, 27, 28, 29, 30, 31, 34, 66, 78, 79, 134, 147, 148, 149, 150, 153, 155, 157, 159, 261, 275, 276, 279, 281, 283, 284, 285, 286, 287, 533, 539, 541, 542, 543, 544, 545, 546, 549 and other compounds from table 1 have very good herbicidal activity post-emergence against weed plants such as *Sinapis alba, Echinochloa crus-galli, Lolium multiflorum, Chrysanthemum segetum,* Setaria spp., *Abutilon theophrasti, Amaranthus retroflexus, Panicum miliaceum* and *Avena sativa* at an application rate of 1 kg or less of active substance per hectare.

3. Tolerance by Crop Plants

In further greenhouse experiments, seeds of a substantial number of crop plants and weeds were placed in sandy loam soil and covered with soil. Some of the pots were treated immediately as described under section 1, and the remaining pots were placed in the greenhouse until the plants have developed two to three true leaves and then sprayed with various dosages of the substances of the formula (I) according to the invention, as described under section 2. Visual scoring four to five weeks after the application and after the plants had been in the greenhouse revealed that the compounds according to the invention leave dicotyledonous crops such as soy, cotton, oilseed rape, sugar beet and potatoes unharmed even when high dosages of active ingredient were used pre- and post-emergence. Moreover, some substances also spared gramineous crops such as barley, wheat, rye, sorghum, corn or rice. Some of the compounds of the formula (I) have high selectivity, and they are therefore suitable for controlling unwanted plant growth in agricultural crops.

What is claimed is:

1. A compound of the formula (I) or salt thereof

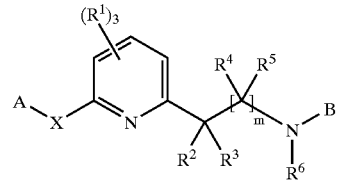

formula (I)

in which $R^1$ is identical or different at each occurrence and is H, halogen, CN, nitro, $SF_5$, $(C_1-C_8)$alkyl, which is unsubstituted or substituted by at least one radical selected from the group consisting of halogen, CN, $(C_1-C_8)$alkoxy, $(C_1-C_8)$alkylthio, $(C_1-C_8)$alkylsulfinyl, $(C_1-C_8)$alkylsulfonyl and $[(C_1-C_8)$alkoxy]-carbonyl, or $R^1$ is $(C_2-C_8)$alkenyl or $(C_2-C_8)$alkynyl, which radicals are unsubstituted or substituted by at least one radical selected from the group consisting of halogen, CN, $(C_1-C_8)$alkoxy and $(C_1-C_8)$alkylthio, or $R^1$ is $(C_1-C_8)$alkoxy, $[(C_1-C_8)$alkyl]-carbonyl, or $(C_1-C_8)$alkylsulfonyl, which radicals are unsubstituted or substituted by at least one radical selected from the group consisting of halogen, CN, $(C_1-C_8)$alkoxy and $(C_1-C_8)$alkylthio, or $R^1$ is $S(O)_p$—$R^7$, where p=0, 1 or 2 and $R^7$ is $(C_1-C_8)$alkyl, $(C_1-C_8)$haloalkyl or $NR^8R^9$, where $R^8$ and $R^9$ independently of one another are identical or different and are H, $(C_1-C_8)$alkyl, $(C_2-C_8)$alkenyl, $(C_7-C_{10})$arylalkyl, $(C_7-C_{10})$alkylaryl or $(C_6-C_{10})$aryl, each of the last-mentioned five radicals being unsubstituted or substituted by one or more radicals from the group consisting of halogen, CN, $(C_1-C_8)$alkoxy, and $(C_1-C_8)$-alkylthio, or $R^1$ is a group of the formula

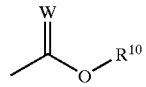

where $R^{10}$ is $(C_1-C_8)$alkyl which is unsubstituted or substituted by one or more radicals from the group consisting of halogen, CN, $(C_1-C_8)$alkoxy, and $(C_1-C_8)$alkylthio, and W=O or S, A is an aryl radical selected from the group consisting of phenyl, naphthyl, tetrahydronaphthyl, indenyl, indanyl, pentalenyl and fluorenyl, said aryl radical being unsubstituted or substituted by one or more radicals selected from the group consisting of halogen, CN, $(C_1-C_8)$ alkyl, $(C_1-C_8)$alkoxy, halo$(C_1-C_8)$alkyl, halo$(C_1-C_8)$ alkyloxy, halo(C₁–C₈)alkylthio, and (C₁–C₈)alkoxy-(C₁–C₈)alkoxy, or a heterocyclic radical selected from the group consisting of pyrrolidyl, piperidyl, pyrazolyl, morpholinyl, indolyl, quinolinyl, pyrimidinyl, triazolyl, oxazolyl, pyridyl, pyrimidinyl, pyridazinyl, pyrazinyl, thiazolyl, thienyl, pyrrolyl, oxazolinyl, isoxazolinyl, isoxazolyl, imidazolyl, and benzoxazolyl, said heterocyclic radical being unsubstituted or substituted by one or more radicals selected from the group consisting of halogen, CN, (C₁–C₈)alkyl, (C₁–C₈)alkoxy, halo(C₁–C₈)alkyl, halo(C₁–C₈)alkyloxy, halo(C₁–C₈)alkylthio, and (C₁–C₈)alkoxy-(C₁–C₈)alkoxy, X is O or S, $R^2$, $R^3$, $R^4$, and $R^5$ are identical or different and are H, halogen, CN, (C₁–C₈)alkoxy or (C₁–C₈)alkyl, each of the two last-mentioned radicals being unsubstituted or substituted by one or more radicals selected from the group consisting of halogen, CN, (C₁–C₈)alkoxy, and (C₁–C₈)alkylthio, m is 0 or 1, $R^6$ is H, (C₁–C₈)alkyl or (C₁–C₈)alkoxy, each of the two last-mentioned radicals being unsubstituted or substituted by one or more radicals selected from the group consisting of halogen, CN, (C₁–C₈)alkoxy, (C₁–C₈)alkylthio, (C₁–C₈)alkylsulfinyl, (C₁–C₈)alkylsulfonyl and [(C₁–C₈)alkoxy]-carbonyl, or $R^6$ is (C₂–C₈)alkenyl or (C₂–C₈)alkynyl, each of the two last-mentioned radicals being unsubstituted or substituted by one or more radicals selected from the group consisting of halogen, CN, (C₁–C₈)alkoxy and (C₁–C₈)alkylthio, or $R^6$ is hydroxyl or an acyl radical selected from the group consisting of formyl, [(C₁–C₈)alkyl]-carbonyl, [(C₂–C₈)alkenyl]-carbonyl, [(C₂–C₈)alkynyl]-carbonyl, (C₁–C₈)alkylsulfonyl, (C₂–C₈)alkenylsulfonyl or (C₂–C₈)alkynylsulfonyl, each of the last-mentioned six radicals being unsubstituted or substituted by one or more radicals selected from the group consisting of halogen, CN, (C₁–C₈)alkoxy and (C₁–C₈)alkylthio, and B is an acyl radical selected from the group consisting of linear or branched [(C₁–C₈)alkyl]-carbonyl and [(C₃–C₆)cycloalkyl]-carbonyl, each of the radicals being unsubstituted or substituted by one or more radicals selected from the group consisting of halogen, (C₁–C₈) alkoxy, (C₁–C₈)alkylthio, (C₁–C₈)alkylsulfinyl, (C₁–C₈)alkylsulfonyl, [(C₁–C₈)alkyl]-carbonyl, [(C₁–C₈)alkoxy]-carbonyl, and CN, or B is [(C₂–C₈)alkenyl]-carbonyl or [(C₂–C₈)alkynyl]-carbonyl, each of the radicals being unsubstituted or substituted by one or more radicals selected from the group consisting of halogen, CN, (C₁–C₈)alkoxy, and (C₁–C₈)alkylthio, or B is a linear or branched C₁–C₈-alkylsulfonyl or (C₃–C₈)cycloalkylsulfonyl, or B is (C₂–C₈)alkenylsulfonyl or (C₂–C₈)alkynylsulfonyl, each of the radicals being unsubstituted or substituted by one or more radicals selected from the group consisting of halogen, CN, (C₁–C₈)alkoxy, and (C₁–C₈)alkylthio, or B and $R^6$ together form a 4- or 5-membered chain, of the formula —(CH₂)ₘ—D— or —D¹—(CH₂)ₘ₁—D—, the chain being unsubstituted or substituted by one or more (C₁–C₄)alkyl radicals, D and D¹ independently of one another being SO₂ or CO, and m=3 or 4 and m¹=2 or 3, with the exception of N-hydroxy-N-[(6-phenoxy-2-pyridyl)methyl]-acetamide and its salts.

2. A compound of the formula (I) or salt thereof formula (I)

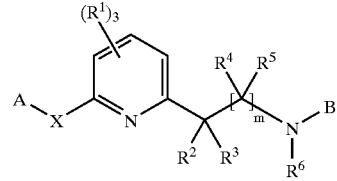

in which $R^1$ is identical or different at each occurrence and is H, halogen, CN, nitro, SF₅, or (C₁–C₈)alkyl which is unsubstituted or substituted by one or more radicals from the group consisting of halogen, CN, (C₁–C₈)alkoxy, (C₁–C₈)alkylthio, (C₁–C₈)alkylsulfinyl, (C₁–C₈)alkylsulfonyl, and [(C₁–C₈)alkoxy]-carbonyl, or $R^1$ is (C₂–C₈)alkenyl or (C₂–C₈)alkynyl which radicals are unsubstituted or substituted by one or more radicals from the group consisting of halogen, CN, (C₁–C₈)alkoxy and (C₁–C₈)alkylthio, or $R^1$ is (C₁–C₈)alkoxy, [(C₁–C₈)alkyl]-carbonyl or (C₁–C₈)alkylsulfonyl, each of the radicals being unsubstituted or substituted by one or more radicals selected from the group consisting of halogen, CN, (C₁–C₈)alkoxy, and (C₁–C₈)alkylthio, or $R^1$ is S(O)$_p$—R⁷, where p=0, 1 or 2 and $R^7$ is (C₁–C₈)alkyl, (C₁–C₈)haloalkyl or NR⁸R⁹, where $R^8$ and $R^9$ independently of one another are identical or different and are H, (C₁–C₈)alkyl, (C₂–C₈)alkenyl, (C₇–C₁₀)arylalkyl, (C₇–C₁₀)alkylaryl or (C₆–C₁₀)aryl, each of the last-mentioned five radicals being unsubstituted or substituted by one or more radicals selected from the group consisting of halogen, CN, (C₁–C₈)alkoxy, and (C₁–C₈)alkylthio, or $R^1$ is a group of the formula

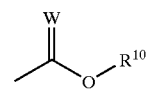

where $R^{10}$ is (C₁–C₈)alkyl which is unsubstituted or substituted by one or more radicals from the group consisting of halogen, CN, (C₁–C₈)alkoxy, and (C₁–C₈)alkylthio, and W=O or S, A is an aryl radical selected from the group consisting of phenyl, naphthyl, tetrahydronaphthyl, indenyl, indanyl, pentalenyl and fluorenyl, said aryl radical being unsubstituted or substituted by one or more radicals selected from the group consisting of halogen, CN, (C₁–C₈)alkyl, (C₁–C₈)alkoxy, halo(C₁–C₈)alkyl, halo(C₁–C₈)alkyloxy, halo(C₁–C₈)alkylthio, and (C₁–C₈)alkoxy-(C₁–C₈)alkoxy, or a heterocyclic radical selected from the group consisting of pyrrolidyl, piperidyl, pyrazolyl, morpholinyl, indolyl, quinolinyl, pyrimidinyl, triazolyl, oxazolyl, pyridyl, pyrimidinyl, pyridazinyl, pyrazinyl, thiazolyl, thienyl, pyrrolyl, oxazolinyl, isoxazolinyl, isoxazolyl, imidazolyl, and benzoxazolyl, said heterocyclic radical being unsubstituted or substituted by one or more radicals selected from the group consisting of halogen, CN, (C₁–C₈)alkyl, (C₁–C₈)alkoxy, halo(C₁–C₈)alkyl, halo(C₁–C₈)alkyloxy, halo(C₁–C₈)alkylthio, and (C₁–C₈)alkoxy-(C₁–C₈)alkoxy, X is O or S, R², R³, R⁴, and R⁵ are identical or different and are H, halogen, CN, (C₁–C₈)alkoxy or (C₁–C₈)alkyl, each of the two last-mentioned radicals being unsubstituted or substituted by one or more radicals selected from the group consisting of halogen, CN, (C₁–C₈)alkoxy, and (C₁–C₈)alkylthio, m is 0 or 1, R⁶ is H, (C₁–C₈)alkyl or (C₁–C₈)alkoxy, each of the two last-mentioned radicals being unsubstituted or substituted by one or more radicals selected from the group consisting of halogen, CN, (C₁–C₈)alkoxy, (C₁–C₈) alkylthio, (C₁–C₈)alkylsulfinyl, (C₁–C₈)alkylsulfonyl and [(C₁–C₈)alkoxy]-carbonyl, or R⁶ is (C₂–C₈)alkenyl or (C₂–C₈)alkynyl, each of the two last-mentioned radicals being unsubstituted or substituted by one or more radicals selected from the group consisting of halogen, CN, (C₁–C₈)alkoxy and (C₁–C₈)alkylthio, or R⁶ is hydroxyl or an acyl radical selected from the group consisting of formyl, [(C₁–C₈) alkyl]-carbonyl, [(C₂–C₈)alkenyl]-carbonyl, [(C₂–C₈)alkynyl]-carbonyl, (C₁–C₈)alkylsulfonyl, (C₂–C₈) alkenylsulfonyl or (C₂–C₈)alkynylsulfonyl, each of the last-mentioned six radicals being unsubstituted or substituted by one or more radicals selected from the group consisting of halogen, CN, (C₁–C₈)alkoxy and (C₁–C₈) alkylthio, or R⁶ is phenylcarbonyl or phenylsulfonyl, the phenyl radical in each of the two last-mentioned radicals being unsubstituted or substituted by one or more radicals selected from the group consisting of halogen, CN, NO₂, (C₁–C₈)alkyl, (C₁–C₈)haloalkyl, and (C₁–C₈) alkoxy, and B is an acyl radical selected from the group consisting of linear or branched [(C₁–C₈)-alkyl]-carbonyl and [(C₃–C₆)cycloalkyl]-carbonyl, each of the radicals being unsubstituted or substituted by one or more radicals selected from the group consisting of halogen, (C₁–C₈)alkoxy, (C₁–C₈)alkylthio, (C₁–C₈) alkylsulfinyl, (C₁–C₈)alkylsulfonyl, [(C₁–C₈)alkyl]-carbonyl, [(C₁–C₈)alkoxy]-carbonyl and CN, or B is [(C₂–C₈)alkenyl]-carbonyl or [(C₂–C₈)alkynyl]-carbonyl, each of the last-mentioned two radicals being unsubstituted or substituted by one or more radicals selected from the group consisting of halogen, CN, (C₁–C₈)alkoxy and (C₁–C₈)alkylthio, or B is a linear or branched (C₁–C₈)-alkylsulfonyl or (C₃–C₈) cycloalkylsulfonyl, or is (C₂–C₈)alkenylsulfonyl or (C₂–C₈)alkynylsulfonyl, each of the radicals being unsubstituted or substituted by one or more radicals selected from the group consisting of halogen, CN, (C₁–C₈)alkoxy and (C₁–C₈)alkylthio, or B is phenylcarbonyl or phenylsulfonyl, the phenyl radical in each of the two last-mentioned radicals being unsubstituted or substituted by one or more radicals selected from the group consisting of halogen, CN, NO₂, (C₁–C₈)alkyl, (C₁–C₈)haloalkyl, and (C₁–C₈)alkoxy, or B is mono- or di-[(C₁–C₈)alkyl]-aminosulfonyl, formyl or a group of the formula —CO—CO—R' in which R'=H, OH, (C₁–C₈)-alkoxy or (C₁–C₈)alkyl, each of the last-mentioned two radicals being unsubstituted or substituted by one or more radicals selected from the group consisting of halogen, CN, (C₁–C₈)alkoxy and (C₁–C₈) alkylthio, or B is a group of the formula

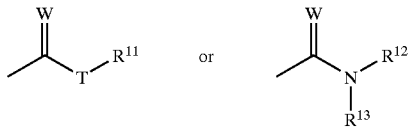

in which

W is O or S,

T is O or S,

R¹¹ is (C₁–C₈)alkyl, (C₂–C₈)alkenyl or (C₂–C₈)alkynyl, each of the three last-mentioned radicals being unsubstituted or substituted by one or more radicals selected from the group consisting of halogen, CN, (C₁–C₈) alkoxy, (C₁–C₈)alkylthio, [(C₁–C₈)alkyl]-carbonyl, and [(C₁–C₈)-alkoxy]-carbonyl, R¹² and R¹³ are identical or different and are H, (C₁–C₈) alkyl, (C₂–C₈)alkenyl or (C₂–C₈)alkynyl, each of the three last-mentioned radicals being unsubstituted or substituted by one or more radicals selected from the group consisting of halogen, CN, (C₁–C₈)alkoxy, (C₁–C₈)alkylthio, [(C₁–C₈)alkyl]-carbonyl, and [(C₁–C₈)-alkoxy]-carbonyl, and the radicals R¹² and R¹³ may together with the nitrogen atom form a heterocyclic radical which has 5 or 6 ring members, may contain further heteroatoms from the group consisting of N, O and S, and is unsubstituted or substituted by (C₁–C₈)alkyl or an oxo group, or B and R⁶ together form a 4- or 5-membered chain, of the formula (—CH₂)ₘ—D— or —D¹—(CH₂)ₘ₁—D—, the chain being unsubstituted or substituted by one or more (C₁–C₄)alkyl radicals, D and D¹ independently of one another being SO₂ or CO, and m=3 or 4 and m¹=2 or 3, with the exception of N-hydroxy-N-[(6-phenoxy-2-pyridyl)methyl]-acetamide and its salts.

3. A compound of the formula (I) or salt thereof as claimed in claim 1, in which R¹ is identical or different at each occurrence and is H, halogen, CN, (C₁–C₈)alkyl or (C₁–C₈)alkoxy, each of the last-mentioned two radicals being unsubstituted or substituted by one or more radicals selected from the group consisting of halogen, CN, (C₁–C₈)alkoxy, and (C₁–C₈)alkylthio, A is a phenyl, pyridyl, pyrazolyl or thienyl radical which is unsubstituted or substituted by one or more radicals from the group consisting of halogen, CN, (C₁–C₈) alkyl, (C₁–C₈)alkoxy, halo(C₁–C₈)alkyl, halo(C₁–C₈) alkyloxy, halo(C₁–C₈)alkylthio, and (C₁–C₈)alkoxy-(C₁–C₈)alkoxy, X is O or S, R² and R³ are identical or different and are H or (C₁–C₈) alkyl, the alkyl radical being unsubstituted or substituted by one or more radicals from the group consisting of halogen, CN, (C₁–C₈)alkoxy, and (C₁–C₈)alkylthio, m is 0, R⁶ is H, formyl, (C₁–C₈)alkyl, (C₃–C₈)alkenyl, (C₃–C₈) alkynyl, (C₁–C₈)-alkoxy or [(C₁–C₈)alkyl]-carbonyl, each of the last-mentioned five radicals being unsubstituted or substituted by one or more radicals from the group consisting of halogen, CN, (C₁–C₈)alkoxy, and (C₁–C₈)alkylthio, and B is linear or branched [(C₁–C₈) alkyl]-carbonyl or [(C₃–C₆)cycloalkyl]-carbonyl, each of the radicals being unsubstituted or substituted by one or more radicals selected from the group consisting of halogen, $(C_1-C_8)$alkoxy, $(C_1-C_8)$alkylthio, $(C_1-C_8)$alkylsulfinyl, $(C_1-C_8)$alkylsulfonyl, $[(C_1-C_8)$alkyl]-carbonyl, $[(C_1-C_8)$alkoxy]-carbonyl, and CN, or B is $[(C_2-C_8)$alkenyl]-carbonyl or $[(C_2-C_8)$alkynyl]-carbonyl, each of the radicals being unsubstituted or substituted by one or more radicals selected from the group consisting of halogen, CN, $(C_1-C_8)$alkoxy, and $(C_1-C_8)$alkylthio, or B is a linear or branched $(C_1-C_8)$-alkylsulfonyl or $(C_3-C_8)$cycloalkylsulfonyl, or B is $(C_2-C_8)$alkenylsulfonyl or $(C_2-C_8)$alkynylsulfonyl, each of the radicals being unsubstituted or substituted by one or more radicals selected from the group consisting of halogen, CN, $(C_1-C_8)$alkoxy, and $(C_1-C_8)$alkylthio.

4. A compound of the formula (I) or salt thereof

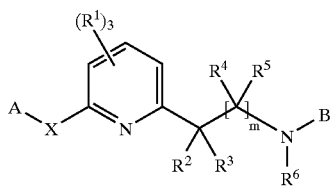

formula (I)

in which $R^1$ in position 3 and in position 5 of the pyridine ring, identical or different at each occurrence, is H or halogen, and $R^1$ in position 4 of the pyridine ring is H, halogen, CN, $(C_1-C_8)$alkyl or $(C_1-C_8)$alkoxy, each of the last-mentioned two radicals being unsubstituted or substituted by one or more radicals selected from the group consisting of halogen, CN, $(C_1-C_8)$alkoxy, and $(C_1-C_8)$alkylthio, A is a group of the formula (A')

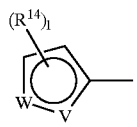

(A')

in which $R^{14}$ is identical or different at each occurrence and is halogen, CN, $(C_1-C_8)$alkyl, $(C_1-C_8)$alkoxy or $(C_1-C_8)$alkylthio, each of the last-mentioned three radicals being unsubstituted or substituted by one or more radicals from the group consisting of halogen, CN, $(C_1-C_8)$alkoxy, and $(C_1-C_8)$alkylthio, l is 1 or 2, V is CH, $C(R^{14})$ or $N(C_1-C_8$-alkyl), W is N, S, N—CH, N—$C(R^{14})$, CH—CH, CH—$C(R^{14})$ or $C(R^{14})$—$C(R^{14})$, $R^2$ and $R^3$ are identical or different and are H or $(C_1-C_8)$ alkyl which is unsubstituted or substituted by one or more radicals from the group consisting of halogen, CN, $(C_1-C_8)$alkoxy, and $(C_1-C_8)$alkylthio, m is 0, $R^6$ is H or $(C_1-C_4)$alkyl which is unsubstituted or substituted by one or more radicals from the group consisting of halogen, CN, $(C_1-C_8)$alkoxy, and $(C_1-C_8)$alkylthio, and B is linear or branched $[(C_1-C_8)$-alkyl]-carbonyl or $[(C_3-C_6)$cycloalkyl]-carbonyl, each of the radicals being unsubstituted or substituted by one or more radicals selected from the group consisting of halogen, $(C_1-C_8)$alkoxy, $(C_1-C_8)$alkylthio, $(C_1-C_8)$alkylsulfinyl, $(C_1-C_8)$alkylsulfonyl, $[(C_1-C_8)$alkyl]-carbonyl, $[(C_1-C_8)$alkoxy]-carbonyl, and CN, or B is $[(C_2-C_8)$alkenyl]-carbonyl or $[(C_2-C_8)$alkynyl]-carbonyl, each of the radicals being unsubstituted or substituted by one or more radicals selected from the group consisting of halogen, CN, $(C_1-C_8)$alkoxy, and $(C_1-C_8)$alkylthio, or B is a linear or branched $(C_1-C_8)$-alkylsulfonyl or $(C_3-C_8)$cycloalkylsulfonyl, or $(C_2-C_8)$ alkenylsulfonyl or $(C_2-C_8)$alkynylsulfonyl, each of the radicals being unsubstituted or substituted by one or more radicals selected from the group consisting of halogen, CN, $(C_1-C_8)$alkoxy, and $(C_1-C_8)$alkylthio.

5. A compound of the formula (I) or salt thereof as claimed in claim 1, in which A is a phenyl, pyridyl, pyrazolyl or thienyl radical which is unsubstituted or substituted by one or more radicals from the group consisting of halogen, CN, $(C_1-C_8)$ alkyl, $(C_1-C_8)$alkoxy, halo$(C_1-C_8)$alkyl, halo$(C_1-C_8)$ alkyloxy, halo$(C_1-C_8)$alkylthio, and $(C_1-C_8)$alkoxy-$(C_1-C_8)$alkyloxy.

6. A compound of the formula (I') or salt thereof

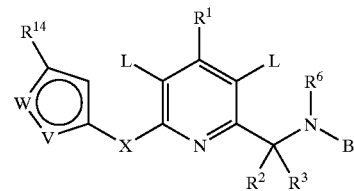

(I')

in which $R^1$ is identical or different at each occurrence and is H, halogen, CN, nitro, $SF_5$, $(C_1-C_8)$alkyl, which is unsubstituted or substituted by at least one radical selected from the group consisting of halogen, CN, $(C_1-C_8)$ alkoxy, $(C_1-C_8)$alkylthio, $(C_1-C_8)$alkylsulfinyl, $(C_1-C_8)$alkylsulfonyl and $[(C_1-C_8)$alkoxy]-carbonyl, or $R^1$ is $(C_2-C_8)$alkenyl or $(C_2-C_8)$alkynyl, which radicals are unsubstituted or substituted by at least one radical selected from the group consisting of halogen, CN, $(C_1-C_8)$alkoxy and $(C_1-C_8)$alkylthio, or $R^1$ is $(C_1-C_8)$ alkoxy, $[(C_1-C_8)$alkyl]-carbonyl, or $(C_1-C_8)$ alkylsulfonyl, which radicals are unsubstituted or substituted by at least one radical selected from the group consisting of halogen, CN, $(C_1-C_8)$alkoxy and $(C_1-C_8)$ alkylthio, or $R^1$ is $S(O)_p$—$R^7$, where p=0, 1 or 2 and $R^7$ is $(C_1-C_8)$alkyl, $(C_1-C_8)$haloalkyl or $NR^8R^9$, where $R^8$ and $R^9$ independently of one another are identical or different and are H, $(C_1-C_8)$alkyl, $(C_2-C_8)$alkenyl, $(C_7-C_{10})$arylalkyl, $(C_7-C_{10})$alkylaryl or $(C_6-C_{10})$aryl, each of the last-mentioned five radicals being unsubstituted or substituted by one or more radicals from the group consisting of halogen, CN, $(C_1-C_8)$alkoxy, and $(C_1-C_8)$-alkylthio, or $R^1$ is a group of the formula

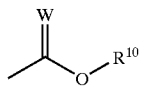

where $R^{10}$ is $(C_1-C_8)$alkyl which is unsubstituted or substituted by one or more radicals from the group consisting of halogen, CN, $(C_1-C_8)$alkoxy, and $(C_1-C_8)$alkylthio, and W=O or S, X is O or S, $R^2$ and $R^3$ are identical or different and are H, halogen, CN, $(C_1-C_8)$alkoxy or $(C_1-C_8)$alkyl, each of the two last-mentioned radicals being unsubstituted or substituted by one or more radicals selected from the group consisting of halogen, CN, $(C_1-C_8)$alkoxy, and $(C_1-C_8)$alkylthio, $R^{14}$ is identical or different at each occurrence and is halogen, CN, $(C_1-C_8)$alkyl, $(C_1-C_8)$alkoxy or $(C_1-C_8)$alkylthio, each of the last-mentioned three radicals being unsubstituted or substituted by one or more radicals selected from the group consisting of halogen, CN, $(C_1-C_8)$alkoxy, and $(C_1-C_8)$alkylthio, $R^6$ is H, $(C_1-C_8)$alkyl, $(C_1-C_8)$alkoxy, $(C_2-C_8)$alkenyl or $(C_2-C_8)$alkynyl, each of the four last-mentioned radicals being unsubstituted or substituted by one or more radicals selected from the group consisting of halogen, CN, $(C_1-C_8)$alkoxy, and $(C_1-C_8)$alkylthio, or $R^6$ is hydroxyl or an acyl radical selected from the group consisting of formyl, $[(C_1-C_8)$alkyl$]$-carbonyl, $[(C_2-C_8)$alkenyl$]$-carbonyl, $[(C_2-C_8)$alkynyl$]$-carbonyl, $(C_1-C_8)$alkylsulfonyl, $(C_2-C_8)$alkenylsulfonyl or $(C_2-C_8)$alkynylsulfonyl, and L is identical or different at each occurrence and is H or halogen, W—V together are N—CH—CH, S—CH, CH—CH—CH or N—N(CH$_3$), and B is $[(C_1-C_8)$alkyl$]$-carbonyl or $(C_1-C_8)$alkylsulfonyl, each of the radicals being unsubstituted or substituted by one or more radicals selected from the group consisting of halogen, CN, $(C_1-C_8)$-alkoxy, and $(C_1-C_8)$alkylthio.

7. A herbicidal or plant-growth-regulating composition comprising a) at least one compound from the formula (I) or salt thereof as claimed in claim 1 and b) formulating auxiliaries customary in crop protection.

8. A method of controlling weed plants comprising the step of applying an effective amount of at least one compound of the formula (I) or salt thereof as claimed in claim 1 to the weed plants, to seeds of the weed plants or to the area where the weed plants are growing.

9. A method of regulating the growth of crop plants comprising the step of applying an effective amount of at least one compound of the formula (I) or salt thereof as claimed in claim 1 to the crop plants, to seeds of the crop plants or to the area where the crop plants are growing.

10. A method of controlling weed plants or regulating the growth of crop plants at a locus comprising the step of applying an effective amount of at least one compound of the formula (I) or salt thereof as claimed in claim 1 to said locus.

11. The method as claimed in claim 9, wherein the crop plants are transgenic crop plants.

12. A process for preparing a compound of the formula (I) or salt thereof as claimed in claim 1, in which a) a compound of the formula (II),

in which each of the radicals $R^1$ is identical or different at each occurrence and is H, halogen, CN, nitro, SF$_5$, $(C_1-C_8)$alkyl, which is unsubstituted or substituted by at least one radical selected from the group consisting of halogen, CN, $(C_1-C_8)$alkoxy, $(C_1-C_8)$alkylthio, $(C_1-C_8)$alkylsulfonyl, $(C_1-C_8)$alkylsulfonyl and $[(C_1-C_8)$alkoxy$]$-carbonyl, or $R^1$ is $(C_2-C_8)$alkenyl or $(C_2-C_8)$alkynyl, which radicals are unsubstituted or substituted by at least one radical selected from the group consisting of halogen, CN, $(C_1-C_8)$alkoxy and $(C_1-C_8)$alkylthio, or $R^1$ is $(C_1-C_8)$alkoxy, $[(C_1-C_8)$alkyl$]$-carbonyl, or $(C_1-C_8)$alkylsulfonyl, which radicals are unsubstituted or substituted by at least one radical selected from the group consisting of halogen, CN, $(C_1-C_8)$alkoxy and $(C_1-C_8)$alkylthio, or $R^1$ is $S(O)_p$—$R^7$, where p=0, 1 or 2 and $R^7$ is $(C_1-C_8)$alkyl, $(C_1-C_8)$haloalkyl or $NR^8R^9$, where $R^8$ and $R^9$ independently of one another are identical or different and are H, $(C_1-C_8)$alkyl, $(C_2-C_8)$alkenyl, $(C_7-C_{10})$arylalkyl, $(C_7-C_{10})$alkylaryl or $(C_6-C_{10})$aryl, each of the last-mentioned five radicals being unsubstituted or substituted by one or more radicals from the group consisting of halogen, CN, $(C_1-C_8)$alkoxy, and $(C_1-C_8)$-alkylthio, or $R^1$ is a group of the formula

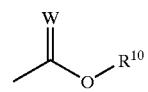

where $R^{10}$ is $(C_1-C_8)$alkyl which is unsubstituted or substituted by one or more radicals from the group consisting of halogen, CN, $(C_1-C_8)$alkoxy, and $(C_1-C_8)$alkylthio, and W=O or S, and L is a leaving group or a group of the formula A—X—, where A is an aryl radical selected from the group consisting of phenyl, naphthyl, tetrahydronaphthyl, indenyl, indanyl, pentalenyl and fluorenyl, said aryl radical being unsubstituted or substituted by one or more radicals selected from the group consisting of halogen, CN, $(C_1-C_8)$alkyl, $(C_1-C_8)$alkoxy, halo$(C_1-C_8)$alkyl, halo$(C_1-C_8)$alkyloxy, halo$(C_1-C_8)$alkylthio, and $(C_1-C_8)$alkoxy-$(C_1-C_8)$alkoxy, or a heterocyclic radical selected from the group consisting of pyrrolidyl, piperidyl, pyrazolyl, morpholinyl, indolyl, quinolinyl, pyrimidinyl, triazolyl, oxazolyl, pyridyl, pyrimidinyl, pyridazinyl, pyrazinyl, thiazolyl, thienyl, pyrrolyl, oxazolinyl, isoxazolinyl, isoxazolyl, imidazolyl, and benzoxazolyl, said heterocyclic radical being unsubstituted or substituted by one or more radicals selected from the group consisting of halogen, CN, (C$_1$–C$_8$)alkyl, (C$_1$–C$_8$)alkoxy, halo (C$_1$–C$_8$)alkyl, halo(C$_1$–C$_8$)alkyloxy, halo(C$_1$–C$_8$) alkylthio, and (C$_1$–C$_8$)alkoxy-(C$_1$–C$_8$)alkyloxy, and X is O or S, is alkylated and then reacted with cyanide to give a nitrile of the formula (III)

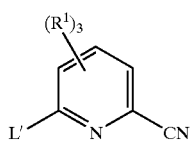
(III)

in which R$^1$ and L are defined as in formula (II);

b) the compound of the formula (III) in which L is a leaving group is reacted with a compound of the formula (IV) or salt thereof

A—X—H (IV)

in which A and X are as defined above, to give a compound of the formula (III) in which L is a group of the formula A—X—; p1 c) the compound of the formula (III) obtained in step a) or b) in which L is a group A—X— and in which A, X, and R$^1$ are as defined above, is converted by reduction into the amino compound of the formula (V)

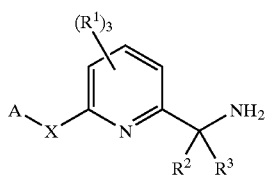
(V)

in which R$^1$, A, and X are as defined above and R$^2$ and R$^3$ are identical or different and are H, halogen, CN, (C$_1$–C$_8$)alkoxy or (C$_1$–C$_8$)alkyl, each of the two last-mentioned radicals being unsubstituted or substituted by one or more radicals selected from the group consisting of halogen, CN, (C$_1$–C$_8$)alkoxy, and (C$_1$–C$_8$) alkylthio; and then d1) the compound of the formula (V) is reacted with acylating reagents to give a compound of the formula (I) in which R$^6$=H, m=0, and A, X, R$^1$, R$^2$ and R$^3$, are as defined above and B is an acyl radical selected from the group consisting of linear or branched [(C$_1$–C$_8$) alkyl]-carbonyl and [(C$_3$–C$_6$)cycloalkyl]-carbonyl, each of the radicals being unsubstituted or substituted by one or more radicals selected from the group consisting of halogen, (C$_1$–C$_8$)alkoxy, (C$_1$–C$_8$)alkylthio, (C$_1$–C$_8$)alkylsulfinyl, (C$_1$–C$_8$)alkylsulfonyl, [(C$_1$–C$_8$)alkyl]-carbonyl, [(C$_1$–C$_8$)alkoxy]-carbonyl, and CN, or B is [(C$_2$–C$_8$)alkenyl]-carbonyl or [(C$_2$–C$_8$)alkynyl]-carbonyl, each of the radicals being unsubstituted or substituted by one or more radicals selected from the group consisting of halogen, CN, (C$_1$–C$_8$)alkoxy, and (C$_1$–C$_8$)alkylthio, or B is a linear or branched C$_1$–C$_8$-alkylsulfonyl or (C$_3$–C$_8$)cycloalkylsulfonyl, or B is (C$_2$–C$_8$)alkenylsulfonyl or (C$_2$–C$_8$)alkynylsulfonyl, each of the radicals being unsubstituted or substituted by one or more radicals selected from the group consisting of halogen, CN, (C$_1$–C$_8$)alkoxy, and (C$_1$–C$_8$) alkylthio; and optionally compounds of the formula (I) in which R$^6$ is H are subsequently acylated; or d2) the compound of the formula (V) is subjected to reductive alkylation with aldehydes and then is acylated.

13. A compound as claimed in claim 4, wherein when R$^1$ in position 3, 4 or 5 is halogen, it is fluorine or chlorine.

14. A compound as claimed in claim 4, wherein R$^{14}$ is identical or different at each occurrence and is (C$_1$–C$_8$) haloalkyl, (C$_1$–C$_8$)haloalkyloxy, (C$_1$–C$_8$)haloalkylthio or (C$_1$–C$_8$)alkoxy (C$_1$–C$_8$)alkyloxy.

15. A compound as claimed in claim 4, wherein V is N(CH$_3$).

16. A compound as claimed in claim 5, wherein X is attached to a carbon atom in group A.

17. A compound as claimed in claim 4, where X is attached to a carbon atom in group A and R$^{14}$ is substituted and is attached to position 3 of group A relative to the carbon atom of group A which is attached to X in the formula (I).

18. A compound as claimed in claim 5, wherein group A is one of the following radicals

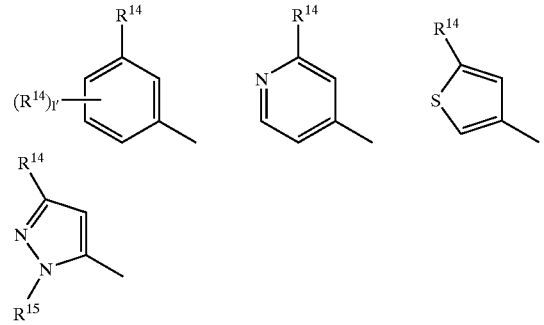

in which

R$^{14}$ is identical or different at each occurrence and is halogen, cyano, (C$_1$–C$_8$)alkyl or (C$_1$–C$_8$)haloalkyl, R$^{15}$ is a (C$_1$–C$_8$)alkyl group, and l' is an integer from 0 to 4.

19. A compound as claimed in claim 18, wherein R$^{14}$ is identical or different at each occurrence and is CF$_3$ or cyano, R$^{15}$ is a methyl group, and l' is either 0 or 1.

20. A compound as claimed in claim 5, wherein group A is one of the following radicals

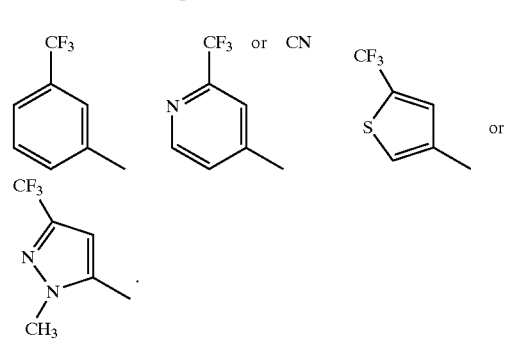

21. A compound as claimed in claim 6, wherein $R^{14}$ is halo($C_1$–$C_8$)alkyl, halo($C_1$–$C_8$)alkyloxy, halo($C_1$–$C_8$)alkylthio, or ($C_1$–$C_8$)alkoxy-($C_1$–$C_8$)alkyloxy.

22. A compound as claimed in claim 6, wherein L is halogen.

23. A compound as claimed in claim 6, wherein B is substituted with one or more halogen atoms.

24. A compound as claimed in claim 4, wherein B is linear or branched [($C_1$–$C_8$)alkyl]-carbonyl or [($C_3$–$C_6$)cycloalkyl]-carbonyl or linear or branched [($C_1$–$C_8$)alkyl]-sulfonyl or [($C_3$–$C_8$)cycloalkyl]-sulfonyl, each of the radicals being unsubstituted or substituted by one or more radicals selected from the group consisting of halogen, CN, ($C_1$–$C_8$)-alkoxy, and ($C_1$–$C_8$)alkylthio.

25. The method of claim 10, wherein the compound of formula (I) or salt thereof is applied to the locus in an amount of from 0.001 to 10 kg/ha.

26. The method of claim 10, wherein the compound of formula (I) or salt thereof is applied to the locus in an amount of from 0.005 to 5 kg/ha.

* * * * *

UNITED STATES PATENT AND TRADEMARK OFFICE
CERTIFICATE OF CORRECTION

PATENT NO. : 6,794,336 B2
DATED : September 21, 2004
INVENTOR(S) : Klaus-Haaf et al.

It is certified that error appears in the above-identified patent and that said Letters Patent is hereby corrected as shown below:

Column 138,
Line 17, "$(C_1-C_8)$alkylsulfonyl, $(C_1-C_8)$alkylsulfonyl," should read
-- $(C_1-C_8)$alkylsulfinyl, $(C_1-C_8)$alkylsulfonyl --.

Column 139,
Line 25, "A-X-p1;" should read -- A-X-; --.

Signed and Sealed this

Tenth Day of May, 2005

JON W. DUDAS
*Director of the United States Patent and Trademark Office*